US008338429B2

(12) United States Patent
Sugasawa et al.

(10) Patent No.: US 8,338,429 B2
(45) Date of Patent: Dec. 25, 2012

(54) 2-ACYLAMINOTHIAZOLE DERIVATIVE OR SALT THEREOF

(75) Inventors: Keizo Sugasawa, Tokyo (JP); Susumu Watanuki, Tokyo (JP); Yuji Koga, Tokyo (JP); Hiroshi Nagata, Tokyo (JP); Ryutaro Wakayama, Tokyo (JP); Fukushi Hirayama, Tokyo (JP); Ken-ichi Suzuki, Tokyo (JP)

(73) Assignee: Astellas Pharma, Inc., Tokyo (JP)

( * ) Notice: Subject to any disclaimer, the term of this patent is extended or adjusted under 35 U.S.C. 154(b) by 166 days.

(21) Appl. No.: 12/615,968

(22) Filed: Nov. 10, 2009

(65) Prior Publication Data
US 2010/0222361 A1 Sep. 2, 2010

Related U.S. Application Data

(63) Continuation of application No. 10/500,964, filed as application No. PCT/JP03/00270 on Jan. 15, 2003, now Pat. No. 7,638,536.

(30) Foreign Application Priority Data

Jan. 18, 2002 (JP) .................................. 2002-10413
Jan. 18, 2002 (JP) .................................. 2002-10447

(51) Int. Cl.
*A61K 31/496* (2006.01)
*C07D 417/14* (2006.01)
(52) U.S. Cl. ................ 514/255; 514/235.1; 514/254.02; 514/316; 514/318; 514/326; 544/360; 544/369; 546/193; 546/212
(58) Field of Classification Search ............... 514/253.1, 514/254.02, 318, 326, 255; 544/360, 369; 546/193, 212
See application file for complete search history.

(56) References Cited

U.S. PATENT DOCUMENTS

| 5,189,049 A | 2/1993 | Frehel et al. |
| 5,256,675 A | 10/1993 | Matsuo et al. |
| 5,314,889 A | 5/1994 | Boigegrain et al. |
| 5,330,998 A | 7/1994 | Clark et al. |
| 5,369,107 A | 11/1994 | Matsuo et al. |
| 5,380,736 A | 1/1995 | Boigegrain et al. |
| 5,384,331 A | 1/1995 | Kogan et al. |
| 5,583,131 A | 12/1996 | Bridger et al. |
| 5,728,709 A | 3/1998 | Ikuina et al. |
| 5,750,540 A | 5/1998 | Tsuchiya et al. |
| 5,932,546 A | 8/1999 | Barrett et al. |
| 5,963,666 A | 10/1999 | Fujisaki et al. |
| 6,040,335 A | 3/2000 | Saitoh et al. |
| 6,083,913 A | 7/2000 | Dower et al. |
| 6,498,155 B1 | 12/2002 | Luengo et al. |
| 6,962,935 B2 | 11/2005 | Pruitt et al. |
| 7,361,658 B2 | 4/2008 | Sugasawa et al. |
| 7,384,967 B2 | 6/2008 | Polisetti et al. |
| 7,638,536 B2 | 12/2009 | Sugasawa et al. |

| 2002/0016471 A1 | 2/2002 | Salituro et al. |
| 2003/0195231 A1 | 10/2003 | Takemoto et al. |
| 2004/0053982 A1 | 3/2004 | Press et al. |
| 2004/0063946 A1 | 4/2004 | Ohkawa et al. |
| 2004/0073029 A1 | 4/2004 | Pruitt et al. |
| 2004/0077697 A1 | 4/2004 | Koshio et al. |
| 2004/0122235 A1 | 6/2004 | Polisetti et al. |
| 2004/0235834 A1 | 11/2004 | Farmer et al. |
| 2005/0153977 A1 | 7/2005 | Sugasawa et al. |
| 2006/0194844 A1 | 8/2006 | Sugasawa et al. |
| 2007/0043087 A1 | 2/2007 | Takayama et al. |
| 2007/0203153 A1* | 8/2007 | Suzuki et al. ............ 514/253.09 |
| 2008/0039475 A1 | 2/2008 | Desjardins et al. |
| 2010/0041668 A1 | 2/2010 | Suzuki et al. |
| 2010/0222329 A1 | 9/2010 | Sugasawa et al. |
| 2011/0224226 A1 | 9/2011 | Desjardins et al. |

FOREIGN PATENT DOCUMENTS

| CA | 2472711 A1 | 7/2003 |
| EP | 0412404 | 1/1996 |
| EP | 747355 | 12/1996 |
| EP | 823423 | 2/1998 |
| EP | 0518731 B1 | 8/1998 |
| EP | 1 207 155 A1 | 5/2002 |
| EP | 1 253 142 | 10/2002 |
| EP | 1466912 A | 10/2004 |
| JP | 3-68567 | 3/1991 |
| JP | 3173876 | 7/1991 |
| JP | 3199451 | 8/1991 |
| JP | AH-05-155871 | 6/1993 |
| JP | 11-152276 | 6/1999 |
| JP | 2002-526482 A | 8/2002 |
| WO | WO 95/06635 | 3/1995 |
| WO | 97/44033 A1 | 11/1997 |
| WO | WO 00/17175 | 3/2000 |
| WO | WO 00/35446 | 6/2000 |
| WO | WO 0107423 | 2/2001 |
| WO | WO 01/53267 | 7/2001 |

(Continued)

OTHER PUBLICATIONS

Nakajima et al. "Synthesis of thiazole . . . " CA143:133362 (2005).*
Thrombocytopenia Wikipedia p. 1-7 (2011).*
Arnold et al. "Current options for . . . " Seminars in Hematology p. 12-23 (2007).*
Cheung et al. "Viral causes . . . " Infect. in Hematology p. 62-64 (2007).*
Cohn et al. "interferon therapy . . . " Am. J. Hematology v.43, p. 246-250 (1993).*
Zondor et al. "Treatment of drug . . . " Exp. opion drug safty abst. (2002).*
Fielder et al. "Regulation of thrombopoietin . . . " Blood v.87(6)p. 2154-2161 (1996).*
Medical Encyclopedia "Idiopathic thrombocytopenic purpura" p. 1-3 (2012).*
Muto et al., CA 137:63257, (2002).
Desjardins et al., "Single and multiple oral doses of AKR501 (YM477) increase the platelet count in healthy volunteers." Blood, vol. 108, No. 11, Part 1, Nov. 2006, p. 145A.

(Continued)

*Primary Examiner* — Celia Chang
(74) *Attorney, Agent, or Firm* — McCarter & English, LLP; Danielle L. Herritt, Esq.; Jin Wang, Esq.

(57) ABSTRACT

A 2-acylaminothiazole derivative or a pharmaceutically acceptable salt thereof having an excellent effect of proliferating human c-mpl-Ba/F3 cells and an activity of increasing platelets based on the effect of promoting the formation of megakaryocytic colonies. A compound or a pharmaceutically acceptable salt thereof useful in treating thrombocytopenia.

8 Claims, No Drawings

FOREIGN PATENT DOCUMENTS

| WO | 02/42298 A1 | 5/2002 |
|---|---|---|
| WO | 02/49632 A1 | 6/2002 |
| WO | WO-02/053160 A1 | 7/2002 |
| WO | WO 02 062775 | 8/2002 |
| WO | WO 02 062792 | 8/2002 |
| WO | 03062233 A1 | 7/2003 |
| WO | WO-03/075921 A2 | 9/2003 |
| WO | WO-03/084544 A2 | 10/2003 |
| WO | WO 03/103657 | 12/2003 |
| WO | WO-2004/002481 A1 | 1/2004 |
| WO | WO-2004/029049 A1 | 4/2004 |
| WO | WO-2004/071447 A3 | 8/2004 |
| WO | WO 2005/007651 | 1/2005 |
| WO | WO 2005/014561 | 2/2005 |

OTHER PUBLICATIONS

Zhou, "Choice of designs and doses for early phase trials." (2004) Fundamental & Clinical Pharmacology 18: 373-378.

Seddon et al., "Pseudopolymorph: A Polemic," (2004) Crystal Growth and Design, vol. 4: 1087.

Van den Ven C, et al., "Sequential treatment with rmIL-3 or simultaneous treatment with rmIL-3 or rhIL-11 with thrombopoietin (TPO) fails to enhance in vivo neonatal rat thrombocytopoiesis." (1997) Exp Hematol 25(9):1005-1012.

Braga, Dario et al., "Making crystals from crystals: a green route to crystal engineering and polymorphism," *Chem. Commun.*, vol. 29:3635-3645 (2005).

Hirai, Kentaro et al., "Syntheses of 2-Disubstituted-amino-4-arylthiazol-5-ylalkanoic acids," *Chem. Pharm. Bull.*, vol. 25:2292-2299 (1977).

Morissette, Sherry et al., "High-throughput crystallization: polymorphs, salts, co-crystals and solvates of pharmaceutical solids," *Advanced Drug Delivery Reviews*, vol. 56:275-300 (2004).

Vippagunta, Sudha et al., "Crystalline solids," *Advanced Drug Delivery Reviews*, vol. 48:3-26 (2001).

Kimura, Tatsuya et al., "A non-peptide compound which can mimic the effect of thrombopoietin via e-mpl", FEBS Letters. 428, 1998, 250-254.

International Search Report for WO 2005/007651, corresponding to U.S. Appl. No. 10/564,520(2005).

International Preliminary Report on Patentability from International Application No. PCT/IB2006/003142 (Corresponding to U.S. Appl. No. 11/593,758). (2007).

Kuter, et al. "Recombinant Human Thrombopoietin: Basic Biology and Evaluation of Clinical Studies," Blood 2002, vol. 100, No. 10.

Vadhan-Raj, et al., "Recom. Hum. Thrombopoietin Attenuates Carboplatin-Indcd. Svre. Thrombocytopenia," Annals of Internal Medicine 2002, vol. 132, No. 5, pp. 364-368.

Vadhan-Raj, et al., "Import. of Predosing of Recomb. Hum. Thrombopoitin to Rdce. Chemotherapy-Indcd. Erly." Journal of Clinical Oncology 2003, vol. 21, No. 16, pp. 3158-3167.

Mutschler et al., "Drug Actions: Basic Principles and Therapeutic Aspects", 1995, CRC Press, pp. 6-8 (1995).

Sugasawa et al. "Preparation of maleic acid . . . " CA 140:321382 (2004).

Katzun, Basic and Clinical Pharmacology, Fourth Edition, pp. 83-92 (1989).

Doods, Drug News & Persepctive, 5(6), pp. 345-362 (1992).

Muto et al. "Preparation of . . . " CA 140:42203 (2003).

Muto et al. "Preparation of phenol . . . " CA 140:422216 (2003).

Takayama et al. "Preparation of thiazole . . . " CA 142:240425 (2005).

Nakajima et al. "Synthesis of thiazole . . . " CA 143:133362 (2005).

Uesaka et al. "Preparation of thiazole . . . " CA 146:229330 (2007).

Cook et al. "Azole series . . . " CA 43:6451 (1949).

\* cited by examiner

2-ACYLAMINOTHIAZOLE DERIVATIVE OR SALT THEREOF

This application is a continuation of U.S. patent application Ser. No. 10/500,964, filed Jul. 8, 2004, which is a 371 application of PCT/JP03/00270, filed Jan. 15, 2003, which claims the benefit of JP Application No. 2002-10413, filed Jan. 18, 2002 and JP Application No. 2002-10447, filed Jan. 18, 2002, the disclosures of which are hereby incorporated by reference in their entireties.

TECHNICAL FIELD

The present invention relates to a novel 2-acylaminothiazole derivative or a salt thereof, which is useful as a medicament particularly in the treatment of thrombocytopenia, and pharmaceutical composition comprising the compound as an active ingredient.

BACKGROUND ART

A platelet is a nuclear blood cell playing an important role in physiological hemostasis and pathological thrombosis, and is continuously produced from megakaryocytes in a living organism. The platelet originates from pluripotent stem cells like other blood cells. Specifically, the pluripotent stem cell becomes a megakaryocytic progenitor cell, from which megakaryoblasts, promegakaryocytes, and megakaryocytes are formed. During the maturation of a megakaryocyte, premature megakaryocytes only carry out DNA synthesis without involving cell division to become a polyploid. Thereafter, cytoplasm begins to mature to form a platelet separation membrane, and a platelet is released by cytoplasm fragmentation.

In addition, since decrease in the number of platelets due to various hematopoietic dysfunctions in aplastic anemia, myelodysplastic syndrome, or chemotherapy or radiotherapy for malignant tumors and the like causes serious symptoms such as hemorrhagic tendencies, there have been many attempts at developing various technologies for increasing the number of platelets for the purpose of treating such dysfunctions. At present, although platelet transfusion is a powerful means for treating thrombocytopenia, a sufficient amount of platelets cannot be provided, and it is difficult to sufficiently improve thrombocytepenia because of a short life span of transfused platelets and the like. Additionally, platelet transfusions involve problems including viral infection, production of alloantibodies, Graft Versus Host Disease (GVHD), and the like. Thus, there is a demand for the development of a medicament for mitigating hematopoietic suppression caused by various conditions or therapies to thereby promote the recovery of platelet number.

Meanwhile, it has been reported that thrombopoietin (hereinafter referred to as "TPO"), which is a c-Mpl ligand playing an important role in differentiation into megakaryocytes, has been cloned, and that it stimulates differentiation and proliferation of megakaryocytes to promote production of platelets (Kaushansky K. et al., Nature, 369, 568-571, 1994: Non-patent Document 1). Clinical tests on TPO as an agent for increasing the number of platelets have been carried out, and its availability and admissibility in humans have been confirmed. However, because a neutralizing antibody was confirmed in a clinic test of PEG-rHuMGDF, a kind of TPO (163 N-terminal amino acids of native TPO modified with polyethyleneglycol) (Li J. et. al., Blood, 98, 3241-3248, 2001: Non-patent Document 2, and Basser R. L. et. al., Blood, 99, 2599-2602, 2002: Non-patent Document 3), there is a concern about immunogenicity of TPO. And, because TPO is a protein, it is decomposed in the digestive tract, and thus is not practical as an agent for oral administration. For the same reason, it is considered that a low molecular peptide is also not practical as an agent for oral administration. Under these circumstances, the development of a nonpeptide c-Mpl ligand, which has low immunogenicity and can be orally administrated, for the purpose of treatment of thrombocytepenia, is under progress.

As such compounds, benzazepine derivatives are disclosed in Japanese Laid-Open Patent Publication No. Hei 11-152276 (Patent Document 1), acylhydrazone derivatives in WO 99/11262 (Patent Document 2), diazonaphthalene derivatives in WO 00/35446 (Patent Document 3), pyrrolocarbazole derivatives in WO 98/09967 (Patent Document 4), pyrrolophenanthridine derivatives in Japanese Laid-Open Patent Publication No. Hei 10-212289, and pyrrolophthalimide derivatives in Japanese Laid-Open Patent Publication No. 2000-44562.

And, it is described in WO 01/07423 (Patent Document 7) that a compound represented by the following general Formula (VII) has an activity of increasing the number of platelets:

(VII)

(wherein symbols are as defined in the above publication).

In addition, the above publication discloses a compound wherein $X^1$ is an optionally substituted thiazole, and $Y^1$ comprises —NHCO—. However, $Ar^1$ or $Ar^2$ of the compound of the present invention is not substituted with a substituent group having an $A^1$ group such as a thiazolyl group as in the above publication. Also, the above publication does not disclose concretely in the Examples and the other parts a compound wherein the 5-position of thiazole is directly substituted with a nitrogen atom.

It is also described in WO 01/53267 (Patent Document 8) that a compound represented by the following general Formula (VIII) has an activity of increasing the number of platelets:

(VIII)

(wherein symbols are as defined in the publication).

The above publication describes a compound wherein $X^1$ is an optionally substituted thiazole, and $Y^1$ comprises —NHCO—. However, $Ar^1$ or $Ar^2$ of the compound of the present invention is not substituted with a substituent group having a $W^1$ group. And, the above publication does not disclose concretely in the Examples and the other parts a compound wherein the 5-position of thiazole is directly substituted with a nitrogen atom.

In addition to the Patent Documents 7 and 8, it is described in Japanese Patent Publication No. 3199451 (Patent Document 9) that a 2-acylaminothiazole compound has the effects of a cholecystokinin and gastrin receptor agonist, and it is described in Chemical and Pharmaceutical Bulletin, 25, 9, 2292-2299, 1977 (Non-patent Document 4) that a 2-acylaminothiazole compound has anti-inflammatory effects. However, there is no description about activity for increasing the number of platelets.

Under these circumstances, there is a demand for the development of a nonpeptide c-Mpl ligand that has low immunogenicity and can be orally administrated, for the purpose of treatment of thrombocytepenia.

[Patent Document 1] Japanese Laid-Open Patent Publication No. Hei 11-152276
[Patent Document 2] WO 99/11262 pamphlet
[Patent Document 3] WO 00/35446 pamphlet
[Patent Document 4] WO 98/09967 pamphlet
[Patent Document 5] Japanese Laid-Open Patent Publication No. Hei 10-212289
[Patent Document 6] Japanese Laid-Open Patent Publication No. 2000-44562
[Patent Document 7] WO 01/07423 pamphlet
[Patent Document 8] WO 01/53267 pamphlet
[Patent Document 9] Japanese Patent Publication No. 3199451
[Non-patent Document 1] Nature, 1994, 369, p. 568-571
[Non-patent Document 2] Blood, 2001, Vol. 98, p. 3241-3248
[Non-patent Document 3] Blood, 2002, Vol. 99, p. 2599-2602
[Non-patent Document 4] Chemical and Pharmaceutical Bulletin, 1977, Vol. 25, 9, p. 2292-2299

DISCLOSURE OF THE INVENTION

The present inventors, as a result of assiduous studies on compounds having platelet increasing activity, discovered that novel 2-acylaminothiazole derivatives have excellent effect of increasing the number of platelets, and completed the present invention.

The present invention relates to the following aspects (1)~(17).

(1) A pharmaceutical composition for increasing the number of platelets comprising a 2-acylaminothiazole derivative represented by the following general Formula (I) or a pharmaceutically acceptable salt thereof as an active ingredient:

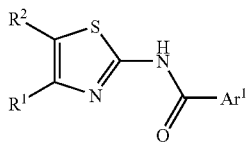
(I)

wherein symbols have the following meanings:

$Ar^1$: aryl, monocyclic aromatic heterocycle, or bicyclic condensed heterocycle, each of which may be substituted (with the proviso that when $R^1$ is aryl or pyridyl, each of which may be substituted with one or more groups selected from the group consisting of lower alkyl, —CO-lower alkyl, —COO-lower alkyl, —OH, —O-lower alkyl, —OCO-lower alkyl, and halogen atom, and $R^2$ is a group represented by the following general Formula (II); $Ar^1$ is not phenyl or pyridyl, each of which may be substituted with one or more groups selected from the group consisting of lower alkyl, —CO-lower alkyl, —COO-lower alkyl, —OH, —O-lower alkyl, —OCO-lower alkyl, and halogen atom.), $R^1$: aryl or monocyclic aromatic heterocycle, each of which may be substituted, $R^2$: a group represented by the following general Formula (II), (III) or (IV):

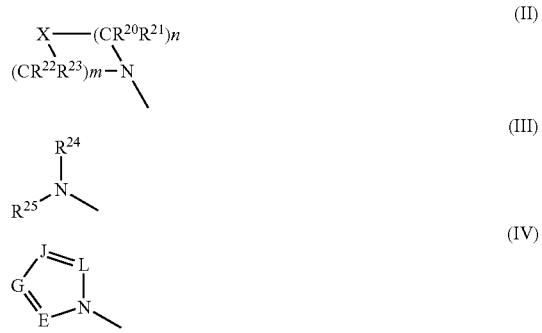

wherein symbols have the following meanings:
n: an integer of 1 to 3,
m: an integer of 1 to 3,
(when n or m is an integer of 2 or more, $CR^{20}R^{21}$ and $CR^{22}R^{23}$ may be identical or different.)
X: O, S, or a group represented by N—$R^{26}$ or C(—$R^{27}$)—$R^{28}$,
E, G, J, L: independently N or a group represented by C—$R^{29}$, with the proviso that at least one of them is C—$R^{29}$,
$R^{20}$, $R^{21}$, $R^{22}$, $R^{23}$, $R^{26}$, $R^{27}$, $R^{28}$, $R^{29}$: which may be identical or different —H; —OH; —O-lower alkyl; optionally substituted lower alkyl; optionally substituted cycloalkyl; optionally substituted aryl; optionally substituted arylalkyl; optionally substituted aromatic heterocycle; optionally substituted aromatic heterocyclic alkyl; optionally substituted nonaromatic heterocycle; optionally substituted lower alkenyl; optionally substituted lower alkylidene; —COOH; —COO-lower alkyl; —COO-lower alkenyl; —COO-lower alkylene-aryl; —COO-lower alkylene-aromatic heterocycle; carbamoyl or amino, each of which may be substituted with one or more groups selected from the group consisting of lower alkyl and cycloalkyl, each of which may be substituted with halogen, —OH, —O-lower alkyl, or —O-aryl; —NHCO-lower alkyl; or oxo.
$R^{24}$, $R^{25}$: which may be identical or different, —H, optionally substituted lower alkyl, optionally substituted cycloalkyl, or optionally substituted nonaromatic heterocycle.

$Ar^1$ in the compound represented by the general Formula (I) is preferably phenyl or monocyclic aromatic heterocycle, each of which may be substituted;
more preferably, phenyl or pyridyl, each of which may be substituted;
still more preferably, phenyl which is unsubstituted at 2- and 6-positions, substituted with —H, —F, —Cl or —Br at 3-position, substituted with —F, —Cl— or —Br at 5-position, and substituted at 4-position, or pyridin-3-yl which is unsubstituted at 2- and 4-positions, substituted with —F, —Cl, or —Br at 5 position, and substituted at 6-position;
most preferably, phenyl which is substituted at 4 position with a group consisting of —O—$R^Y$; optionally substituted piperidin-1-yl and optionally substituted piperazin-1-yl, or pyridin-3-yl which is substituted at 6-position with a group consisting of —O—$R^Y$, —NH—$R^Y$, optionally substituted piperidin-1-yl, and optionally substituted piperazin-1-yl.

The "$R^Y$" is lower alkyl which may be substituted with one or more groups selected from the group consisting of —OH, —O-lower alkyl, amino which may be substituted with one or two lower alkyl, —$CO_2H$, —$CO_2$-lower alkyl, carbamoyl which may be substituted with one or two lower alkyl, cyano, aryl, aromatic heterocycle, nonaromatic heterocycle, and halogen atom.

$R^1$ in the compound of the general Formula (I) is preferably phenyl or thienyl, each of which may be substituted; more preferably, phenyl or thienyl, each of which may be substituted with one or more groups selected from the group consisting of halogen atom and trifluoromethyl; still more preferably, phenyl or thienyl, each of which is substituted with 1 to 3 halogen atoms (when substituted with 2 or 3 halogen atoms, the halogen atoms may be identical or different.).

$R^2$ in the compound of the general Formula (I) is preferably a group represented by the general Formula (II); more preferably, a group represented by the general Formula (II) wherein n is 2, m is 2, and X is a group represented by N—$R^{26}$ or C(—$R^{27}$)—$R^{28}$; still more preferably, 4-(piperidin-1-yl)piperidin-1-yl, 4-propylpiperidin-1-yl, 4-cyclohexylpiperazin-1-yl, or 4-propylpiperazin-1-yl.

(2) The pharmaceutical composition according to (1) wherein $R^1$ is phenyl or thienyl, each of which may be substituted with 1 to 3 halogen atoms (when substituted with 2 or 3 halogen atoms, the halogen atoms may be identical or different); $R^2$ is a group represented by the general Formula (II), (wherein n is 2, m is 2, and X is a group represented by N—$R^{26}$ or C(—$R^{27}$)—$R^{28}$); and $Ar^1$ is phenyl or pyridyl, each of which may be substituted.

(3) The pharmaceutical composition according to (1) or (2), wherein the pharmaceutical composition is used as a therapeutic agent for thrombocytopenia.

(4) The pharmaceutical composition according to (1) or (2), wherein the pharmaceutical composition is used as a c-Mpl ligand.

(5) A 2-acylaminothiazole derivative represented by the following general Formula (V) or a pharmaceutically acceptable salt thereof.

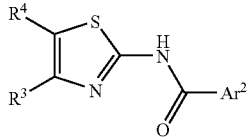

(V)

wherein symbols have the following meaning, $Ar^2$: a group represented by $Ar^1$ as described in (1), with the proviso that indol-2-yl is excluded, $R^3$: a group represented by $R^1$ as described in (1), $R^4$: a group represented by $R^2$ as described in (1), with the proviso that a group represented by the general Formula (IV) is excluded.

$Ar^2$ in the compound of the general Formula (V) is preferably phenyl or monocyclic aromatic heterocycle, each of which may be substituted;

more preferably, phenyl or pyridyl, each of which may be substituted;

still more preferably, phenyl which is unsubstituted at 2- and 6-positions, substituted with —H, —F, —Cl, or —Br at 3-position, substituted with —F, —Cl, or —Br at 5-position, and substituted at 4-position, or pyridin-3-yl which is unsubstituted at 2- and 4-positions, substituted with —F, —Cl, or —Br at 5-position, and substituted at 6-position;

most preferably, phenyl substituted at 4-position with a substituent group selected from the group consisting of —O—$R^Y$, —NH—$R^Y$, optionally substituted piperidin-1-yl and optionally substituted piperazin-1-yl, or pyridin-3-yl which is substituted at 6-position with a substituent group selected from the group consisting of —O—$R^Y$, —NH—$R^Y$, optionally substituted piperidin-1-yl and optionally substituted piperazin-1-yl.

$R^3$ in the compound of the general Formula (V) is preferably phenyl or thienyl, each of which may be substituted; more preferably, phenyl or thienyl, each of which may be substituted with one or more groups selected from the group consisting of halogen atom and trifluoromethyl; still more preferably, phenyl or thienyl, each of which is substituted with 1 to 3 halogen atoms (when substituted with 2 or 3 halogen atoms, the halogen atom may be identical or different.)

$R^4$ in the compound of the general Formula (V) is preferably a group represented by the general Formula (II), more preferably a group represented by the general Formula (II) wherein n is 2, m is 2, and X is N—$R^{26}$ or C—($R^{27}$)—$R^{28}$; still more preferably, 4-(piperidin-1-yl)piperidin-1-yl, 4-propylpiperidin-1-yl, 4-cyclohexylpiperazin-1-yl, or 4-propylpiperazin-1-yl.

(6) The compound according to (5), wherein $Ar^2$ is phenyl or monocyclic aromatic heterocycle, each of which may be substituted.

(7) The compound according to (6), wherein $R^3$ is phenyl or thienyl, each or which may be substituted; $R^4$ is a group represented by the general Formula (II); $Ar^2$ is phenyl or pyridyl, each of which may be substituted.

(8) The compound according to (7), wherein n is 2, m is 2, and X is a group represented by N—$R^{26}$ or C(—$R^{27}$)—$R^{28}$.

(9) The compound according to (8), wherein $R^3$ is phenyl or thienyl, each of which is substituted with 1 to 3 halogen atoms (when substituted with 2 or 3 halogen atoms, the halogen atoms may be identical or different.).

(10) The compound according to (9), wherein $R^4$ is 4-(piperidin-1-yl)piperidin-1-yl, 4-propylpiperidin-1-yl, 4-cyclohexylpiperazin-1-yl, or 4-propylpiperazin-1-yl.

(11) The compound according to (10), wherein Are is phenyl which is unsubstituted at 2- and 6-positions, substituted with —H, —F, —Cl, or —Br at 3 position, substituted with —F, —Cl, or —Br at 5-position, and substituted at 4-position; or pyridin-3-yl which is unsubstituted at 2- and 4-positions, substituted with —F, —Cl, or —Br at 5-position, and substituted at 6-position.

(12) The compound according to (11), wherein $Ar^2$ is phenyl which is substituted at 4-position with a group selected from the group consisting of —O—$R^Y$, —NH—$R^Y$, optionally substituted piperidin-1-yl and optionally substituted piperazin-1-yl; or pyridin-3-yl which is substituted at 6-position with a group selected from the group consisting of —O—$R^Y$, —NH—$R^Y$, optionally substituted piperidin-1-yl and optionally substituted piperazin-1-yl (wherein $R^Y$ is lower alkyl which may be substituted with one or more groups selected from the group consisting of —OH, —O-lower alkyl, amino which may be substituted with one or two lower alkyl, —CO$_2$H, —CO-lower alkyl, carbamoyl which may be substituted with one or two lower alkyl, cyano, aryl, aromatic heterocycle, nonaromatic heterocycle, and halogen atom.).

(13) The compound according to any one of (5) to (12), which is selected from the group consisting of compound group X, compound group Y, and pharmaceutically acceptable salts thereof, preferably selected from compound group X or pharmaceutically acceptable salts thereof.

The "compound group X" includes:
N-[4-(4-chlorothiophen-2-yl)-5-(4-cyclohexylpiperazin-1-yl)thiazol-2-yl]-3-fluoro-4-hydroxybenzamide, 3-chloro-N-[4-(4-chlorothiophen-2-yl)-5-(4-cyclohexylpiperazin-1-yl)thiazol-2-yl]-4-(2-hydroxyethoxy)benzamide,
N-[4-(4-chlorothiophen-2-yl)-5-(4-propylpiperidino)thiazol-2-yl)]-2-methoxyisonicotinamide,
N-[4-(4-chlorothiophen-2-5-yl)-5-(4-cyclohexylpiperazin-1-yl)thiazol-2-yl]isoquinoline-6-carboxamide,
3-chloro-N-[4-(4-chlorothiophen-2-yl)-5-(4-propylpiperazin-1-yl)thiazol-2-yl]-4-(2-hydroxyethoxy)benzamide,
5-chloro-N-[4-(4-chlorothiophen-2-yl)-5-(4-cyclohexylpiperazin-1-yl)thiazol-2-yl]-6-(3-hydroxypropoxy)nicotinamide,
5-chloro-N-[4-(4-chlorothiophen-2-yl)-5-(4-cyclohexylpiperazin-1-yl)thiazol-2-yl]-6-[(3-hydroxypropyl)amino)]nicotinamide,
1-(3-chloro-5-{[4-(4-chlorothiophen-2-yl)-5-(4-cyclohexylpiperazin-1-yl)thiazol-2-yl]carbamoyl}-2-pyridyl)piperidine-4-carboxylic acid,
1-(3-chloro-5-{[4-(4-chlorothiophen-2-yl)-5-(4-propylpiperazin-1-yl)thiazol-2-yl]carbamoyl}-2-pyridyl)piperidine-4-carboxylic acid,
N-[4-(4-chlorothiophen-2-yl)-5-(4-cyclohexylpiperazin-1-yl)thiazol-2-yl]-4-(4-cyanopiperidino)-3,5-difluorobenzamide,
1-(2-chloro-4-{[4-(4-chlorothiophen-2-yl)-5-(4-cyclohexylpiperazin-1-yl)thiazol-2-yl]carbamoyl}phenyl)piperidine-4-carboxylic acid,
1-(2-chloro-4-{[4-(4-chlorothiophen-2-yl)-5-(4-cyclohexylpiperidin-1-yl)thiazol-2-yl]carbamoyl}-6-fluorophenyl)piperidine-4-carboxylic acid,
1-(2-chloro-4-{[4-(4-chlorothiophen-2-yl)-5-(4-propylpiperazin-1-yl)thiazol-2-yl]carbamoyl}phenyl)piperidine-4-carboxamide,
5-chloro-N-[4-(4-chlorothiophen-2-yl)-5-(4-cyclohexylpiperazin-1-yl)thiazol-2-yl]-6-(4-hydroxymethylpiperidino)nicotinamide,
1-(3-chloro-5-{[5-(4-cyclohexylpiperazin-1-yl)-4-(4-fluorophenyl)thiazol-2-yl]carbamoyl}-2-pyridyl)piperidine-4-carboxylic acid,
1-(3-chloro-5-{[5-(4-cyclohexylpiperazin-1-yl)-4-(3-trifluoromethylphenyl)thiazol-2-yl]carbamoyl}-2-pyridyl)piperidine-4-carboxylic acid,
5-chloro-N-[4-(4-chlorothiophen-2-yl)-5-(4-cyclohexylpiperazin-1-yl)thiazol-2-yl]-6-{4-[(2-methoxyethyl)carbamoyl]piperidino}nicotinamide,
5-chloro-N-[4-(4-chlorothiophen-2-yl)-5-(4-cyclohexylpiperazin-1-yl)thiazol-2-yl]-6-{4-[(3-methoxypropyl)carbamoyl]piperidino}nicotinamide, and
5-chloro-N-[4-(4-chlorothiophen-2-yl)-5-(4-cyclohexylpiperazin-1-yl)thiazol-2-yl]-6-[4-(morpholinocarbonyl)piperidino]nicotinamide.

The "compound group Y" includes:
N-[4-(4-chlorothiophen-2-yl)-5-(4-cyclohexylpiperazin-1-yl)thiazol-2-yl]-2-methoxyisonicotinamide,
3-chloro-N-[4-(4-chlorothiophen-2-yl)-5-(4-cyclohexylpiperazin-1-yl)thiazol-2-yl]-4-(2-methoxyethoxy)benzamide,
N-[4-(4-chlorothiophen-2-yl)-5-(4-cyclohexylpiperazin-1-yl)thiazol-2-yl]quinoline-6-carboxamide,
3-chloro-N-[4-(5-chlorothiophen-2-yl)-5-(4-cyclohxylpiperazin-1-yl)thiazol-2-yl]-4-(2-hydroxyethoxy)benzamide,
3-chloro-N-[4-(4-chlorothiophen-2-yl)-5-(4-cyclohexylpiperazin-1-yl)thiazol-2-yl]-5-fluoro-4-(2-hydroxyethoxy)benzamide,
3-chloro-N-[4-(4-chlorothiophen-2-yl)-5-(4-cyclohexylpiperazin-1-yl)thiazol-2-yl]-4-(3-hydroxypropoxy)benzamide,
3,5-dichloro-N-[4-(4-chlorothiophen-2-yl)-5-(4-cyclohexyl)piperazin-1-yl)thiazol-2-yl]-4-(2-hydroxyethoxy)benzamide,
3-bromo-N-[4-(4-chlorothiophen-2-yl)-5-(4-cyclohexylpiperazin-1-yl)thiazol-2-yl]-4-(2-hydroxyethoxy)benzamide,
N-[4-(4-chlorothiophen-2-yl)-5-(4-cyclohexylpiperazin-1-yl)thiazol-2-yl]-2-oxo-2,3-dihydrobenzoxazole-6-carboxamide,
3-chloro-N-[4-(4-chlorothiophen-2-yl)-5-(4-cyclohexylpiperazin-1-yl)thiazol-2-yl]-4-hydroxybenzamide,
(±)-5-chloro-N-[4-(4-chlorothiophen-2-yl)-5-(4-cyclohexylpiperazin-1-yl)thiazol-2-yl]-6-(3-hydroxypyrrolidin-1-yl)nicotinamide,
5-chloro-N-[4-(4-chlorothiophen-2-yl)-5-(4-cyclohexylpiperazin-1-yl)thiazol-2-yl]-6-(4-hydroxypiperidino)nicotinamide,
5-chloro-N-[4-(4-chlorothiophen-2-yl)-5-(4-propylpiperazin-1-yl)thiazol-2-yl]-6-[(2-hydroxyethyl)amino]nicotinamide,
5-chloro-N-[4-(4-chlorothiophen-2-yl)-5-(4-propylpiperazin-1-yl)thiazol-2-yl]-6-(4-hydroxypiperidino)nicotinamide,
5-chloro-N-[4-(4-chlorothiophen-2-yl)-5-(4-cyclohexylpiperazin-1-yl)thiazol-2-yl]-6-(3-oxopiperazin-1-yl)nicotinamide,
6-(4-carbamoylpiperidino)-5-chloro-N-[4-(4-chlorothiophen-2-yl)-5-(4-cylclohexylpiperazin-1-yl)thiazol-2-yl)]nicotinamide,
(±)-5-chloro-N-[4-(4-chlorothiophen-2-yl)-5-(4-cyclohexylpiperazin-1-yl)thiazol-2-yl]-6-[(2,3-dihydroxypropyl)amino]nicotinamide,
(±)-5-chloro-N-[4-(4-chlorothiophen-2-yl)-5-(4-cyclohexylpiperazin-1-yl)thiazol-2-yl]-6-[(tetrahydro-3-furyl)methoxy]nicotinamide,
6-(4-carbamoylpiperidino)-5-chloro-N-[4-(4-chlorothiophen-2-yl)-5-(4-propylpiperazin-1-yl)thiazol-2-yl]nicotinamide,
3-chloro-N-[4-(4-chlorothiophen-2-yl)-5-(4-cyclohexylpiperazin-1-yl)thiazol-2-yl]-4-(4-hydroxypiperidino)benzamide,
1-(2-bromo-4-{[4-(4-chlorothiophen-2-yl)-5-(4-cyclohexylpiperazin-1-yl)thiazol-2-yl]carbamoyl}phenyl)piperidine-4-carboxylic acid,
1-(2-bromo-4-{([4-(4-chlorothiophen-2-yl)-5-(4-cyclohexylpiperazin-1-yl)thiazol-2-yl]carbamoyl}phenyl)piperidine-4-carboxamide,
1-(4-{[4-(4-chlorothiophen-2-yl)-5-(4-cyclohexylpiperazin-1-yl)thiazol-2-yl]carbamoyl-2,6-difluorophenyl)piperidine-4-carboxylic acid,
3-chloro-N-[4-(4-chlorothiophen-2-yl)-5-(4-cyclohexylpiperazin-1-yl)thiazol-2-yl]-4-(4-cyanopiperidino)benzamide,
1-(4-{[4-(4-chlorothiophen-2-yl)-5-(4-cyclohexylpiperazin-1-yl)thiazol-2-yl]carbamoyl}-2,6-difluorophenyl)piperidine-4-carboxamide,
3-chloro-N-[4-(4-chlorothiophen-2-yl)-5-(4-propylpiperazin-1-yl)thiazol-2-yl]-4-(4-hydroxypiperidino)benzamide,
1-(2-chloro-4-{[4-(4-chlorothiophen-2-yl)-5-(4-cyclohexylpiperazin-1-yl)thiazol-2-yl]carbamoyl}phenyl)piperidine-4-carboxamide, 1-(2-chloro-4-{[4-(4-chlorothiophen-2-yl)-5-(4-propylpiperazin-1-yl)thiazol-2-yl]carbamoyl}phenyl)piperidin-4-carboxylic acid, 3-chloro-N-[4-(4-chlorothiophen-2-yl)-5-(4-cyclohexylpiperazin-1-yl)thiazol-2-yl]-4-(4-cyanopiperidino)-5-fluorobenzamide, 1-(2-chloro-4-{[4-(4-chlorothiophen-2-yl)-5-(4-cyclohexylpiperazin-1-yl)thiazol-2-yl]carbamoyl}-6-fluorophenyl)piperidine-4-carboxamide, 1-(3-chloro-5-{[4-(3-chlorophenyl)-5-(4-cyclohexylpiperazin-1-yl)thiazol-2-yl]carbamoyl)}-2-pyridyl)piperidine-4-carboxylic acid, 5-chloro-N-[4-(4-chlorothiophen-2-yl)-5-(4-cyclohexylpiperidin-1-yl)thiazol-2-yl]-6-(5-oxo-1,4-diazepan-1-yl)nicotinamide,

[1-(3-chloro-5-{[4-(4-chlorothiophen-2-yl)-5-(4-cyclohexylpiperazin-1-yl)thiazol-2-yl]carbamoyl}-2-pyridyl)piperidin-4-yl]acetic acid, 5-chloro-N-[4-(4-chlorothiophen-2-yl)-5-(4-cyclohexylpiperazin-1-yl)thiazol-2-yl]-6-{4-[(dimethylamino)carbonyl]piperidino}nicotinamide, 5-chloro-N-[4-(4-chlorothiophen-2-yl)-5-(4-cyclohexylpiperazin-1-yl)thiazol-2-yl]-6-{4-[(methylamino)carbonyl]piperidino}nicotinamide,

[4-(3-chloro-5-{[4-(4-chlorothiophen-2-yl)-5-(4-cyclohexylpiperazin-1-yl)thiazol-2-yl]carbamoyl}-2-pyridyl)piperazin-1-yl]acetic acid, 6-[4-(acetylamino)piperidino]-5-chloro-N-[4-(4-chlorothiophen-2-yl)-5-(4-cyclohexylpiperazin-1-yl)thiazol-2-yl]nicotinamide, 3-chloro-N-[4-(4-chlorothiophen-2-yl)-5-(4-cyclohexylpiperazin-1-yl)thiazol-2-yl]-5-fluoro-4-[4-(methoxyacetyl)piperazin-1-yl]benzamide,

[4-(2-chloro-4-{[(4-chlorothiophen-2-yl)-5-(4-cyclohexylpiperazin-1-yl)thiazol-2-yl]carbamoyl}-6-fluorophenyl)piperazin-1-yl]acetic acid, 3-chloro-N-[4-(4-chlorothiophen-2-yl)-5-(4-cyclohexylpiperazin-1-yl)thiazol-2-yl]-5-fluoro-4-(4-sulfamoylpiperazin-1-yl)benzamide, 4-[4-(carbamoylmethyl)piperazin-1-yl]-3-chloro-N-[4-(4-chlorothiophen-2-yl)-5-(4-cyclohexylpiperazin-1-yl)thiazol-2-yl]-5-fluorobenzamide, 5-chloro-N-[4-(4-chlorothiophen-2-yl)-5-(4-cyclohexylpiperazin-1-yl)thiazol-2-yl]-6-[4-(propylcarbamoyl)piperidino]nicotinamide, and 5-chloro-N-[4-(4-chlorothiophen-2-yl)-5-(4-cyclohexylpiperazin-1-yl)thiazol-2-yl]-6-{4-[(2-ethoxyethyl)carbamoyl]piperidino}nicotinamide.

(14) A pharmaceutical composition comprising the compound of any one of (5) to (13) as an active ingredient.

(15) The pharmaceutical composition according (14), wherein the pharmaceutical composition is used as an agent for increasing the number of platelets.

(16) The pharmaceutical composition according to (14), wherein the pharmaceutical composition is used as a therapeutic agent for thrombocytopenia.

(17) The pharmaceutical composition according to (14), wherein the pharmaceutical composition is used as a c-Mpl ligand.

The compound of the present invention is a 2-acylaminothiazole derivative structurally characterized in that an acylamino group is substituted at the 2-position thereof and that a nitrogen atom of a nitrogen; containing heterocycle is directly bound to the 5-position thereof. Also, it has pharmacological characteristics of showing the effects of proliferating human c-mpl Ba/F3 cells and promoting differentiation of human $CD34^+$ into megakaryocytes, and good effects in oral administration test for mice, and thus, having the activity of increasing the number of platelets.

The present invention will be explained in more detail herein below.

In the definition of the general formula for the compound of the present invention, the term "lower" means a straight or branched carbon chain having from 1 to 6 carbon atoms, unless otherwise indicated.

Thus, the "lower alkyl" means alkyls having 1 to 6 carbon atoms, and its examples include methyl, ethyl, propyl, isopropyl, butyl, isobutyl, sec-butyl, tert-butyl, pentyl, neopentyl, hexyl, and the like, of which those having 1 to 3 carbon atoms such as methyl, ethyl, propyl, and isopropyl are preferred.

The "lower alkenyl" means alkenyls having 2 to 6 carbon atoms, and its examples include ethenyl, propenyl, butenyl, pentenyl, hexenyl and the like, of which those having 2 to 3 carbon atoms such as ethenyl, 1-propenyl, 2-propenyl, and 3-propenyl are preferred.

The "lower alkylidene" means alkylidenes having 1 to 6 carbon atoms, and its examples include methylidene, ethylidene, propylidene, butylidene, pentylidene, hexylidene, and the like, of which those having 1 to 3 carbon atoms such as methylidene, ethylidene, 1-propylidene, and 2-propylidene are preferred.

The "lower alkylene" means a divalent group of alkyls having 1 to 6 carbon atoms, of which those having 1 to 4 carbon atoms such as methylene, ethylene, trimethylene, methylethylene, tetramethylene, dimethylmethylene, and dimethylethylene are preferred.

The "cycloalkyl" means a carbon ring having 3 to 8 carbon atoms, which may have partial unsaturation. Its examples include cyclopropyl, cyclobutyl, cyclopentyl, cyclohexyl, cyclooctyl, cyclobutenyl, cyclohexenyl, cyclooctadienyl, and the like.

The "aryl" means a mono- to tri-cyclic aromatic ring having 6 to 14 carbon atoms, of which phenyl and naphthyl are preferred, and phenyl is more preferred.

The "arylalkyl" means the "lower alkyl" substituted with the "aryl", and its examples include benzyl, 1-phenethyl, 2-phenethyl, naphthylmethyl, 1-naphthylethyl, 2-naphthylethyl and the like.

The "monocyclic aromatic heterocycle" means a monovalent group of five- to six-membered aromatic heterocycle or its partially hydrogenated ring, which may comprise a nitrogen, an oxygen, or a sulfur atom, and its examples include thienyl, furyl, pyrrolyl, thiazolyl, oxazolyl, imidazolyl, isothiazolyl, isoxazolyl, pyrazolyl, thiadiazolyl, oxadiazolyl, triazolyl, tetrazolyl, pyridyl, pyrazinyl, pyrimidinyl, pyridazinyl and the like.

The "bicyclic condensed heterocycle" means a monovalent group of an aromatic heterocycle condensed with an aryl or monocyclic aromatic heterocycle, or its partially hydrogenated ring, which may comprise a nitrogen, an oxygen, or a sulfur atom, and its example include indolyl, isoindolyl, indolizinyl, indazolyl, quinolyl, isoquinolyl, quinolidinyl, phthalazinyl, naphthylidinyl, quinoxalinyl, quinazolinyl, cinnolinyl, benzimidazolyl, imidazopyridyl, benzofuranyl, benzoxazolyl, 1,2-benzoisoxazolyl, benzothienyl, benzothiazolyl, oxazolopyridyl, thiazolopyridyl, indolinyl, isoindolinyl, 1,2-dihydroquinolinyl, 1,2,3,4-tetrahydroquinolinyl, 3,4-dihydro-2H-1,4-benzoxazinyl, 1,4-dihydro-2H-3,1-benzoxazinyl, chromanyl, isochromanyl, benzoxolanyl, benzodioxolanyl, benzodioxanyl, and the like.

The "aromatic heterocycle" means the "monocyclic aromatic heterocycle" combined with the "bicyclic condensed heterocycle".

The "aromatic heterocyclic alkyl" means the "lower alkyl" substituted with the "aromatic heterocycle", and its examples include thienylmethyl, furylmethyl, pyridylmethyl, thiazolylmethyl, oxazolylmethyl, imidazolylmethyl, thienylethyl, furylethyl, pyridylethyl, and the like.

The "non-aromatic heterocycle" means a monovalent group of a non-aromatic heterocycle, which may be condensed with an aryl or monocyclic aromatic heterocycle, and has one or more hetero atoms, which are identical or different, selected from the group consisting of a nitrogen, an oxygen, and a sulfur, and its examples include azetidinyl, pyrrolidinyl, imidazolinyl, imidazolidinyl, pyrazolidinyl, pyrazolinyl, piperidinyl, azepinyl, piperazinyl, homopiperazinyl, morpholinyl, thiomorpholinyl, indolinyl, isoindolinyl, and the like.

The "halogen" includes fluorine, chlorine, bromine, and iodine atoms.

The "ligand" means a low molecular weight substance binding to an enzyme, receptor, protein, and the like, and includes an agonist and antagonist, of which an agonist is preferred.

As substituent groups that can be used for the term "optionally substituted" or "which may be substituted", those commonly used as substituent groups for each group can be used, and each group may have one or more substituent groups.

As the substituent groups that can be used for "aryl or monocyclic aromatic heterocycle, each of which may be substituted" in the definition of $R^1$, "optionally substituted cycloalkyl", "optionally substituted aryl", "optionally substituted arylalkyl", "optionally substituted aromatic heterocycle", "optionally substituted aromatic heterocyclic alkyl", and "optionally substituted nonaromatic heterocycle" in the definitions of $R^{20}$, $R^{21}$, $R^{22}$, $R^{23}$, $R^{26}$, $R^{27}$, $R^{28}$, and $R^{29}$, and the "optionally substituted cycloalkyl" and "optionally substituted nonaromatic heterocycle" in the definitions of $R^{24}$ and $R^{25}$, the following groups (a) to (h) can be exemplified. Wherein, "$R^Z$" is a lower alkyl which may be substituted with one or more groups selected from the group consisting of —OH, —O-lower alkyl, amino which may be substituted with one or two lower alkyls, carbamoyl which may be substituted with one or two lower alkyls, aryl, aromatic heterocycle, and halogen.

(a) halogen;
(b) —OH, —O—$R^Z$, —O-aryl, —OCO—$R^Z$, oxo(=O);
(c) —SH, —S—$R^Z$, —S-aryl, —SO—$R^Z$, —SO-aryl, $SO_2R^Z$, $SO_2$-aryl, sulfamoyl which may be substituted with one or two $R^Z$;
(d) amino which may be substituted with one or two $R^Z$, —NHCO—$R^Z$, —NHCO-aryl, —NHCO$_2$—$R^Z$, —NHCONH$_2$, —NHSO$_2$—$R^Z$, —NHSO$_2$-aryl, —NHSO$_2$NH$_2$, nitro;
(e) —CHO, —CO—$R^Z$, —CO$_2$H, —CO$_2$—$R^Z$, carbamoyl which may be optionally substituted with one or two $R^Z$, cyano;
(f) aryl or cycloalkyl, each of which may be substituted with one or more groups selected from the group consisting of —OH, —O-lower alkyl, amino which may be substituted with one or two lower alkyl, halogen and $R^Z$;
(g) aromatic heterocycle or nonaromatic heterocycle, each of which may be substituted with one or more groups selected from the group consisting of —OH, —O-lower alkyl, amino which may be substituted with one or two lower alkyl, halogen and $R^Z$;
(h) lower alkyl which may be substituted with one or more groups selected from the substituent groups described in (a) to (g).

As the substituent groups that can be used for the "optionally substituted lower alkyl", "optionally substituted lower alkenyl", and "optionally substituted lower alkylidene" in the definitions of $R^{20}$, $R^{21}$, $R^{22}$, $R^{23}$, $R^{26}$, $R^{27}$, $R^{28}$, and $R^{29}$, and the "optionally substituted lower alkyl" in the definitions of $R^{24}$ and $R^{25}$, the group described in (a) to (g) can be exemplified.

As the substituent groups that can be used for the "aryl, monocyclic aromatic heterocycle, or bicyclic condensed heterocycle, each of which may be substituted" in the definition of $Ar^1$, oxo (with the proviso that oxo can be used only for a bicyclic condensed heterocycle); and a group represented by the general Formula (VI) can be exemplified.

$$A\text{-}B\text{-}C\text{-}D\text{-}E \qquad (IV)$$

Wherein symbols have the following meanings,

-A-: a single bond, or optionally substituted cyclic aminediyl (with the proviso that the cyclic aminediyl is bound to $Ar^1$ with nitrogen atom of the cyclic amine thereof.), —B—: a single bond, —O—, —NH—, —N(—$R^Z$)—, —NHCO—, —CO—, —CONH—, or —CON(—$R^Z$)—, —C—: a single bond; or, lower alkylene or lower alkenylene, each of which may be substituted with one or more groups selected from the group consisting of halogen and —OH, -D-: a single bond, —NHCO—, —NHSO$_2$—, —CO—, or —SO$_2$—, -E: —H; halogen; —OH; —O—$R^Z$; —O—CO—$R^Z$; amino which may be substituted with one or two $R^Z$; —$R^Z$; cyano; aryl, cycloalkyl, aromatic heterocycle or nonaromatic heterocycle, each of which may be substituted, with the proviso that —CH$_2$-nonaromatic heterocycle, and —CH=nonaromatic heterocycle (with the proviso that the carbon atom of the nonaromatic heterocycle is substituted with methyne) are excluded from the group represented by the general Formula (VI); and in case $Ar^1$ is an aryl or monocyclic aromatic heterocycle, each of which may be substituted, the following groups are excluded:

a group wherein -A- and —B— form a single bond, —C— is a single bond, or ethylene or vinylene, each of which may be substituted with one or more groups selected from the group consisting of halogen and —OH, and -D- is —CO—, a group wherein -A- and —B— form a single bond, —C— is a single bond, or ethylene or vinylene, each of which may be substituted with one or more groups selected from the group consisting of halogen and —OH, -D- is —SO$_2$—, and -E- is amino which may be substituted with one or two $R^Z$, a group wherein -A- and —B— form a single bond, —C— is a single bond, or ethylene or vinylene, each of which may be substituted with one or more groups selected from the group consisting of halogen and —OH, -D- is a single bond -E- is a monovalent group of aryl, partially unhydrogenated monocyclic aromatic heterocycle, or a ring condensed with partially unhydrogenated monocyclic aromatic heterocycle, each of which may be substituted, a group wherein -A- is a single bond, and —B— is —CO—, a group wherein -A-, —B—, —C— and -D- form a single bond, and -E is a monovalent group of aryl, partially unhydrogenated monocyclic aromatic heterocycle, or a ring condensed with partially unhydrogenated monocyclic aromatic heterocycle.

And, the "cyclic aminediyl (with the proviso that the cyclic aminediyl is bound to $Ar^1$ with nitrogen atom of the cyclic amine thereof.)" in the definition of -A- means a divalent group of three to eight-membered (in the case of a condensed ring or spiro ring, five- to fifteen-membered) aromatic or nonaromatic cyclic amines, which have at least one nitrogen atom, and may have one or more hetero atoms, identical or different, selected from the group consisting of nitrogen, oxygen, and sulfur, including a condensed ring and spiro ring, and $Ar^1$ is directly substituted with the at least one nitrogen atom. Its examples include divalent groups of azepine, pyrrolidine, piperidine, piperazine, N-methylpiperazine, azepane, diazepane, N-methyldiazepane, morpholine, thiomorpholine, isoindoline, 1,4-dioxa-8-azaspiro[4,5]decane, 1-oxa-8-azaspiro-[4,5]decane, 1-oxa-8-azaspiro[4,5]undecane, and the like.

As the substituent groups that can be used for the "optionally substituted cyclic aminediyl" in the definition of -A- and the "aryl, cycloalkyl, aromatic heterocycle, or nonaromatic heterocycle, each of which may be substituted" in the definition of -E-, the groups described in (a) to (h), and lower alkylidene which may be substituted with the groups (a) to (h) can be exemplified.

The compound of the present invention represented by the general

Formula (I) or (V) may comprise asymmetric carbon atoms depending on the kinds of substituent groups, and optical isomers based on the asymmetric carbon atom may exist. The compound of the present invention includes a mixture of these optical isomers or isolated ones. And, tautomers may exist in the compound of the present invention, and the compound of the present invention includes these isomers as a mixture or an isolated one. As the tautomer, 2-hydroxypyridine and 2-pyridone can be exemplified. And, labeled compounds, i.e., compounds wherein one or more atoms are labeled with radioisotopes or non-radioisotopes, are also included in the present invention.

In addition, the compound of the present invention may form a salt, which is included in the present invention as long as pharmaceutically acceptable. Examples of the salt include addition salts with a mineral acid such as hydrochloric acid, hydrobromic acid, hydroiodic acid, sulfuric acid, nitric acid, phosphoric acid, and the like, or an organic acid such as formic acid, acetic acid, propionic acid, oxalic acid, malonic acid, succinic acid, fumaric acid, maleic acid, lactic acid, malic acid, tartaric acid, citric acid, methanesulfonic acid, ethanesulfonic acid, p-toluenesulfonic acid, aspartic acid, glutamic acid, and the like; salts with an inorganic base such as sodium, potassium, magnesium, calcium, and the like, or an organic base such as methylamine, ethylamine, ethanolamine, lysine, ornithine, and the like; and ammonium salts, and the like. And, a hydrate and a solvate of the compound and its pharmaceutically acceptable salt of the present invention, and those having polymorphism are also included in the present invention. In addition, the compound of the present invention also includes a compound which is metabolized in a living body to be converted into the compound of the general Formula (I) or (V) or its salt, a so-called prodrug. As groups forming the prodrug, those described in Prog. Med., 5; 2157-2161, 1985; and Hirokawa-Shoten, 1990, "Development of medicine" Vol. 7, Molecular Design, pp 163-198 can be exemplified.

<Production Method>

The compound and its pharmaceutically acceptable salt of the present invention can be prepared by various known synthesis methods, using characteristics based on its basic backbone or the kinds of substituent groups. The following describes representative preparation methods. And, according to the kinds of functional groups, it is advantageous in some cases in terms of preparation technique to substitute a functional group with a suitable protection group, i.e., a group that can be easily converted into the functional group, in the raw material or intermediate step. Then, if necessary, the protection group is removed to obtain a desired compound. Examples of the functional group include hydroxyl, carboxy, and amino groups, and examples of the protection group include those described in "Protective Groups in Organic Synthesis", third edition, edited by Greene and Wuts. It is preferable to suitably use them depending on reaction conditions.

(First Production Method)

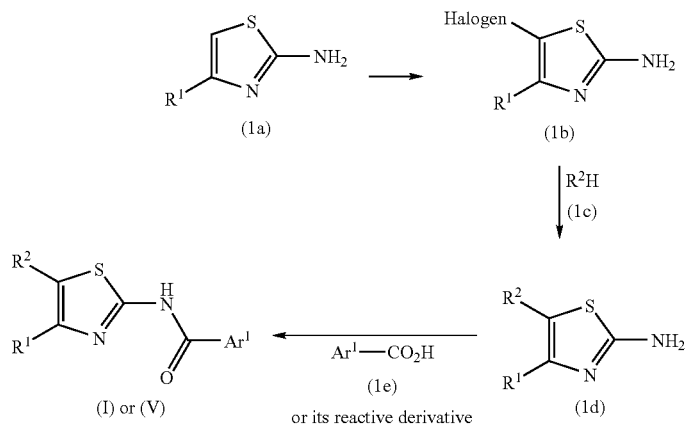

(wherein $R^1$, $R^2$, $Ar^1$ are as defined in the foregoing)

In this method, a compound of the general Formula (I) or (V) is prepared by the amidation of a compound (1d) or its salt with a compound (1e) or its reactive derivative by a general method, and then, if necessary, removing a protection group.

As the reactive derivatives of the compound (1e), a common ester such as methylester, ethylester, tert-butyl ester, and the like; an acid halide such as acid chloride, acid bromide, and the like; an acid azide; an active ester with N-hydroxybenzotriazole, p-nitrophenol, or N-hydroxysuccinimide, or the like; a symmetrical acid anhydride; an acid anhydride mixture with alkyl carbonate, p-toluenesulfonic acid, or the like can be exemplified.

In case the compound (1e) is reacted in its free acid form, or active ester or acid halide without isolation, and the like, it is preferable to carry out the reaction using a condensing agent such as dicylcohexylcarbodiimide, carbonyldiimidazole, diphenylphosphorylazide, diethylphosphorylcyanide, or 1-ethyl-3-(3-dimethylaminopropyl)carbodiimide hydrochloride (WSC.HCl), and phosphorous oxychloride in pyridine solvent.

The reaction is, although it varies depending on the reactive derivatives or condensing agent, carried out in an inert organic solvent such as a halogenated hydrocarbon including dichloromethane, dichloroethane, chloroform and the like; an aromatic hydrocarbon including benzene, toluene, xylene and the like; ether including ether, tetrahydrofuran (THF) and the like; an ester including ethyl acetate; N,N-dimethylformamide (DMF) or dimethylsulfoxide (DMSO), and the like, under cooling, cooling to room temperature, or room temperature to heating.

In order to progress the reaction smoothly, it is advantageous in some cases to employ an excess amount of the compound (1e) or carry out the reaction in the presence of a base such as N-methylmorpholine, trimethylamine, triethylamine, N,N-dimethylaniline, pyridine, 4-(N,N-dimethylamino)pyridine, picoline, lutidine, and the like. And, a salt consisting of a strong acid and weak base such as pyridine hydrochloride, pyridine p-toluenesulfonate, N,N-dimethylaniline hydrochloride and the like can be used. Pyridine can also be used as a solvent.

Particularly, it is advantageous to carry out the reaction in a solvent such as acetonitrile or DMF using a base such as pyridine or N,N-dimethylaniline, or using pyridine as a solvent.

The starting material (1d) used in the reaction can be prepared by synthesizing a compound (1b) by halogenation of the 5-position of a compound (1a) and then reacting the compound (1b) with a compound (1c). The compound (1b) can also be used in subsequent reaction without isolation.

As a halogenation agent, those commonly used for a halogen substitution reaction of hydrogen on an aromatic ring can be used. A halogen atom such as chlorine, bromine and the like, dioxanedibromide, phenyltrimethylammonium tribromide, a pyridine such as pyridinium hydrobromide perbromide, pyrrolidonehydrotribromide and the like, a perbromide such as α-pyrrolidone, quaternary ammonium, dioxane and the like are appropriate. An imide-type halogenation agent such as N-bromosuccinimide, N-chlorosuccinimide and the like, a hydrogen halide such as hydrochloric acid, hydrobromic acid and the like, a metal agent such as copper (II) halide including copper bromide (II), copper chloride (II), and the like can also be used.

In case a halogen or perbromide is used, the compound (1a) can be reacted in an inert organic solvent such as halogenated hydrocarbon; ether; alcohol including methanol (MeOH), ethanol (EtOH), 2-propanol, ethyleneglycol and the like; aromatic hydrocarbon; acetic acid; ester including ethyl acetate (EtOAc) and the like. If necessary, the reaction may be carried out in the presence of a small amount of a catalyst such as hydrogen halide. It is preferable to carry out the reaction at −30° C. to reflux temperature of the used solvent.

In case a hydrogen halide is used as a halogenation agent, the compound (1a) can be reacted therewith in an acid solution or a base solution such as sodium hydroxide aqueous solution, and the reaction is preferably carried out at −30° C. to reflux temperature of the used solvent. And, in case a metal agent is used as a halogenation agent, the compound (1a) is generally dissolved in an inert organic solvent such as halogenated hydrocarbon, ether, alcohol, aromatic hydrocarbon, acetic acid, ester, and the like, or water, or a mixture thereof to react with the agent, and if necessary, it is advantageous to carry out the reaction in the presence of a small amount of a catalyst such as hydrogen halide, under room temperature to heating.

The thus-obtained compound (1b) is reacted with the compound (1c) in a non-protonic polar solvent such as DMF, N-methyl-2-pyrrolidone, DMSO and the like, an inert organic solvent such as halogenated hydrocarbon, ether, aromatic hydrocarbon, or water, or a mixture thereof to prepare a compound (1d). The reaction is preferably carried out at room temperature to reflux temperature of the used solvent.

In order to progress the reaction smoothly, it is advantageous in some cases to employ an excess amount of the compound (1e) or carry out the reaction in the presence of a base such as N-methylmorpholine, triethylamine, diethylisopropylamine, N,N-dimethylaniline, pyridine, 4-(N,N-dimethylamino)pyridine, picoline, lutidine and the like.

(Second Production Method)

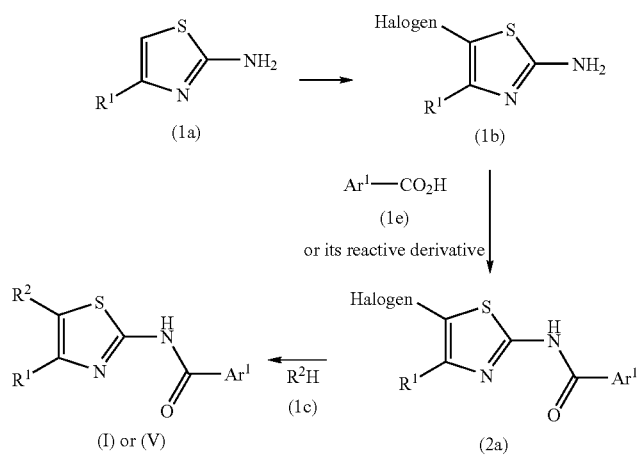

In this method, a compound (2a) is synthesized by the amidation of the compound (1b) synthesized by the first production method with a compound (1e) or its reactive derivative, and then reacted with a compound (1c), and if necessary a protection group is removed to prepare the compound (I) or (V) of the present invention.

Any step can be carried out in accordance with the steps of the first production method.

And, the thus-obtained compounds can be subjected to a process commonly used in the art such as alkylation, acylation, substitution, oxidation, reduction, hydrolysis, and the like to prepare some of the compounds of the general Formula (I) or (V).

The thus-produced compound of the present invention is isolated and purified as its free form or as a salt thereof. A salt of the compound (I) can be produced by subjecting it to a usual salt formation reaction. The isolation and purification are carried out by usual chemical manipulations such as extraction, concentration, evaporation, crystallization, filtration, recrystallization, various types of chromatography and the like.

Various types of isomers can be separated by usual method using the difference in physicochemical properties among isomers. For example, a racemic mixture can be separated by a general racemic mixture resolution method, e.g., a method in which racemic mixture is converted into diastereomer salts with an optically active acid such as tartaric acid and the like and then subjected to optical resolution. And, diastereomers can be separated by fraction crystallization or various types of chromatography or the like. Also, optically active compounds can be prepared using appropriate optically active starting materials.

Industrial Applicability

The compound and its salt of the present invention have excellent effects of increasing the number of platelets. Thus, the compound of the present invention is useful in the treatment and/or prevention of thrombocytopenia due to aplastic anemia, myelodysplastic syndrome, chemotherapy or radiotherapy for malignant tumors, idiopathic thrombocytopenic purpura, liver disease, HIV, and the like. In case thrombocytopenia is likely to be caused by chemotherapy or radiotherapy, it is possible to administrate the compound of the present invention prior to carrying out the therapy.

Pharmaceutical efficacy of the compound of the present invention was confirmed by the following tests.

(i) Human c-mpl-Ba/F3 Cell Proliferation Test

In a 96 well microplate, $2\times10^5$ cells/ml of human c-mpl-Ba/F3 cells were cultured at 37° C. for 24 hours with 10% fetal bovine serum containing a RPMI1640 medium (100 μl/well) to which varied concentrations of tested compounds were respectively added. After the culturing, 10 μl/well of WST-1/1-methoxy PMS (cell counting kit, Dojindo) were added. Immediately after the adding and after 2 hours, absorbance of A450/A650 was measured with a microplate reader (Model 3350:Bio-Rad), and the absorbance increase after 2 hours was regarded as proliferation activity of each tested compound. The results are shown in Table 1.

Each term in the Table has the following meaning.

pot.: Concentration of tested compound for promoting cell proliferation of the compound of Example 9 (compound of Example 9 and rhTPO in rhTPO) to 30% of maximum cell proliferation activity value.

Efficacy: Maximum cell proliferation activity value of tested compound when the maximum cell proliferation activity value of the compound of Example 9 (compound of Example 9 and rhTPO in rhTPO) is set to 100%.

TABLE 1

Human c-mpl-Ba/F3 cell proliferation activity of the compound of the present invention

| Tested compound | pot. [nM] | Efficacy [%] |
|---|---|---|
| Example 9 | 10 | 87 |
| Example 16 | 2.4 | 93 |
| Example 66 | 14 | 99 |
| Example 103 | 18 | 97 |
| Example 214 | 15 | 106 |
| Example 250 | 6.7 | 87 |
| Example 272 | 3.3 | 96 |
| Example 276 | 8.7 | 100 |
| Example 280 | 4.9 | 107 |
| Example 328 | 9.0 | 88 |
| Control 1 | 4.4 | 101 |
| Control 2 | 2.1 | 96 |
| Control 3 | 6.9 | 96 |
| rhTPO | 0.012 | 100 |

As Control 1, the compound A-1 of the Patent Document 7 was employed; as the Control 2; the compound A-14 of the Patent Document 8 was employed; and as Control 3, the compound J-14 of the Patent Document 8 was employed. The structures of the control compounds are shown below.

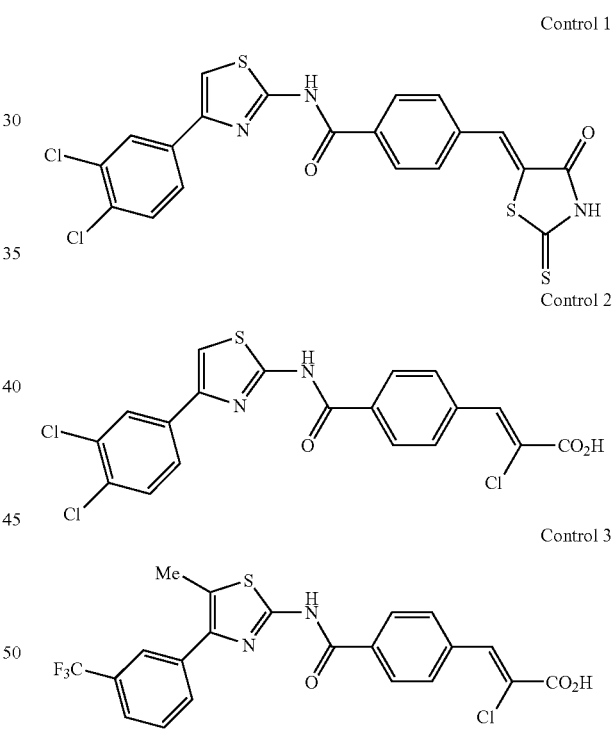

From the above results, it has been verified that the compound of the present invention has an activity of proliferating human c-Mpl Ba/F3 cells. (ii) Test for measuring effects of promoting the formation of megakaryocytic colonies Human $CD34^+$ cells were cultured at 37° C. for 10-14 days in the presence of tested materials in a 2 well chamber slide, using MegaCult™-C (Stem Cell Technologies). In accordance with the attached instructions, dehydration, fixing, and staining with antihuman glycoprotein IIb/IIIa antibody were carried out. A group of 3 or more stained megakaryocytes was regarded as 1 colony, and the number of colonies per well was measured with a microscope. $EC_{30}$ values of each tested compound were calculated from a capacity curve.

As results, the compound of Example 9 had an $EC_{30}$ value of 12 nM, the compound of Example 66 was 47 nM, and the compound of Example 250 was 26 nM.

From these results, it has been confirmed that the compound of the present invention has excellent effects of promoting the formation of megakaryocytic colonies.

(iii) Oral Administration Test for Mice

To male ICR mice, a tested compound dissolved or suspended in 0.5% methylcellulose aqueous solution was orally administrated in an amount of 100 mg/kg or 10 mg/kg. After 2 hours, blood was drawn from the inferior vena cava of the abdomen using 1/10 capacity of 3.8% sodium citrate as an anticoagulant. Plasma obtained by centrifugation at 12,000 rpm for 3 minutes was warmed up at 56° C. for 30 minutes, and added to the human c-mpl.Ba/F3 cell proliferation system described in (i) such that the final plasma concentration became 10%, and then cell proliferation activity was measured. The cell proliferation activity (%) of each plasma batch, when maximum cell proliferation activity of each tested compound was set to 100%, was calculated. The results are as shown in Table 2.

TABLE 2

Human c-mpl-Ba/F3 cell proliferation activity of plasma after tested compound is orally administrated

| Tested compound | dose [mg/kg p.o.] | Cell proliferation activity [%] |
| --- | --- | --- |
| Example 16 | 10 | >80% |
| Example 66 | 10 | 61% |
| Example 214 | 10 | >80% |
| Example 250 | 10 | >80% |
| Example 272 | 10 | >80% |
| Example 276 | 10 | >80% |
| Example 280 | 10 | >80% |
| Example 328 | 10 | >80% |
| Control 1 | 100 | <10% |
| Control 2 | 100 | <10% |
| Control 3 | 100 | <10% |

From the above results, it has been verified that the compound of the present invention has oral activity in mice. Particularly, it is very surprising that the control did not show oral activity at 100 mg/kg, while the compound of the present invention showed good oral activity even at 10 mg/kg, which is considered to be achieved by the introduction of a directly bonding nitrogen atom at the 5-position of thiazole. And; controls 2 and 3 showed <10% of cell proliferation activity with the same dose (10 mg/kg p.o.) as the compounds of Examples. It has also been confirmed that, in a mouse in which human platelet production is recognized after transplanting human hematopoietic stem cells, effects of increasing the number of platelets are recognized by orally administering the compound of the present invention.

A pharmaceutical composition of the present invention can be prepared by generally used methods using one or more kinds of the compound of the present invention of the general Formula (I) or (V) and pharmaceutical carriers, fillers, and other additives generally used in the preparation of medicaments. It may be administered either by oral administration through tablets, pills, capsules, granules, powders, solutions and the like, or by parenteral administration through injections such as intravenous injection, intramuscular injection and the like, or through suppositories, or pernasal, permucosal, or percutaneous preparations and the like.

The solid composition for use in the oral administration according to the present invention is used in the forms of tablets, powders, granules and the like. In such a solid composition, one or more active substances are mixed with at least one kind of inert diluent such as lactose, mannitol, glucose, hydroxypropylcellulose, microcrystalline cellulose, starch, polyvinyl pyrrolidone, metasilicate, or magnesium aluminate. In the usual way, the composition may contain additives other than the inert diluent, which include a lubricant such as magnesium stearate, a disintegrating agent such as calcium cellulose glycolate, a stabilizing agent such as lactose, and a solubilization-assisting agent such as glutamic acid or aspartic acid. As occasion demands, tablets or pills may be coated with a sugar coat or a film of gastrosoluble or enterosoluble substance such as sucrose, gelatin, hydroxypropylcellulose, hydroxypropylmethylcellulose phthalate, or the like.

The liquid composition for oral administration includes pharmaceutically acceptable emulsions, solutions, suspensions, syrups, elixirs and the like, and contains a generally used inert diluent such as purified water or ethanol. In addition to the inert diluent, this composition may also contain auxiliary agents such as a moistening agent and a suspending agent, as well as a sweetener, a flavor, an aromatic, and an antiseptic.

The injections for parenteral administration include aseptic aqueous or non-aqueous solutions, suspensions, and emulsions. Examples of the aqueous solutions and suspensions include distilled water for injection use, and physiological saline. Examples of the non-aqueous solutions and suspensions include plant oil such as propylene glycol, polyethylene glycol, olive oil or the like; an alcohol such as ethanol, polysorbate 80 (trade name) and the like. Such a composition may further contain auxiliary agents such as an antiseptic, a moistening agent, an emulsifying agent, a dispersing agent, a stabilizing agent (e.g., lactose), and a solubilization-assisting agent (e.g., glutamic acid or aspartic acid. These compositions are sterilized for example by filtration through a bacteria-retaining filter, blending of a germicide, or irradiation. Alternatively, they may be used by firstly making into sterile solid compositions and dissolving them in sterile water or a sterile solvent for injection use prior to their use.

In the case of oral administration, a daily dose is approximately 0.0001-50 mg/kg of body weight, preferably approximately 0.001-10 mg/kg, and more preferably approximately 0.01-1 mg/kg, and the daily dose is administered once a day or by dividing it into 2 to 4 doses per day. In the case of intravenous administration, a daily dose is approximately 0.0001-1 mg/kg of body weight, preferably approximately 0.0001-0.1 mg/kg, and the daily dose is administered once a day or by dividing it into plural doses per day. The dose is appropriately decided by taking symptoms, age, and sex of the patient to be treated and the like into consideration.

BEST MODE FOR CARRYING OUT OF THE INVENTION

The following describes the invention more illustratively with reference to examples, but the present invention is not limited to these examples. In this connection, novel materials are included in the starting materials to be used in the examples, and production methods of the starting materials from known materials are described as reference examples.

REFERENCE EXAMPLE 1

To a solution of 4.18 g of 4-chloro-2-acetylthiophene in 30 ml of diethylether, 1.5 ml of bromine was added under ice cooling, and the mixture was stirred at room temperature for 2 hours. Water was added to the reaction solution, and the organic phase was extracted. The obtained organic layer was washed with brine and dried over anhydrous sodium sulfate.

The solvent was evaporated under reduced pressure to obtain brominated compound. To a solution of the brominated compound in 30 ml of EtOH, 2.1 g of thiourea was added at room temperature, and the mixture was stirred at 80° C. overnight. The precipitate was filtered, and obtained solution was evaporated under reduced pressure. Chloroform was added and then an organic layer was washed with aqueous potassium carbonate and brine, and dried over sodium sulfate. The residue obtained by the evaporation of the solvent under reduced pressure was washed with hexane:EtOAc=1:1 to obtain 2.57 g of 2-amino-4-(4-chlorothiophen-2-yl)thiazole.

Compounds of Reference Examples 2-8 as shown in Table 3 were synthesized employing each corresponding starting material, in the same manner as described in Reference Example 1.

Each symbol in the Table has the following meaning.
Rf Reference Example number
Data: physical data (MS:FAB-MS(M+H)+; MN: FAB-MS (M−H)$^-$; MM: FAB-MS(M)$^+$; NMR: δ (ppm) of peaks in $^1$H-NMR employing DMSO-$d_6$ as a measuring solvent, unless otherwise indicated, and $(CH_3)_4Si$ as an internal standard)
Structure: chemical structure
$R^1$, $R^2$, Ar: substituent group in the general Formula (Me: methyl, Et: ethyl, nPr: normal propyl, nBu: normal butyl, tBu: tert-butyl, cHex: cyclohexyl, cHep: cycloheptyl, allyl: allyl, Ph: phenyl, Bn: benzyl, cyano: cyano, Ac: acetyl, Boc: tert-butyloxycarbonyl, Fur: furanyl, The: thienyl, azet: azetidin-1-yl, pryy: pyrrolidin-1-yl, pipe: piperidin-1-yl, pipa: piperazin-1-yl, mor: morpholin-4-yl, tmor:thiomorpholin-4-yl, imid: imidazol-1-yl, TBS: tert-butyldimethylsillyl, the number before the substituent group indicates substitution position, and as examples, 5-Cl-3-The indicates 5-chlorothiophen-3-yl, and 4-cHex-pipa 4-cylcohexylpiperazin-1-yl.)

TABLE 3

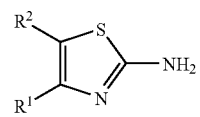

| Rf | $R^1$ | Data |
|---|---|---|
| 1 | 4-Cl-2-The | MS; 217. |
| 2 | 5-Cl-3-The | MS; 217. |
| 3 | 5-F-2-The | MS; 201. |
| 4 | 3-F-2-The | MS; 201. |
| 5 | 5-Me-2-The | MS; 197. |
| 6 | 4-Me-2-The | MS; 197. |
| 7 | 4-F-5-Cl-2-The | MS; 235. |
| 8 | 4-F-2-The | MS; 201. |

REFERENCE EXAMPLE 9

To a solution of 6.0 g of 2-amino-4-(4-fluorophenyl)thiazole in 100 ml of THF, 1.60 ml of bromine was added dropwisely, and the mixture was stirred at room temperature for 90 minutes. After evaporation of the solvent, 100 ml of DMF, 10.4 g of 1-cyclohexylpiperazine, and 17.2 ml of triethylamine were added, and the mixture was stirred at 90 for 31 hours. The solvent was evaporated under reduced pressure, and the residue was mixed with saturated aqueous $NaHCO_3$ and extracted with chloroform. The organic layer was washed with brine, and dried over sodium sulfate. The residue obtained by the evaporation of the solvent under reduced pressure was purified by silica gel column chromatography (elute:chloroform-MeOH =100:1-100:3) to obtain 11.26 g of 2-amino-5-(4-cyclohexylpiperazin-1-yl)-4-(4-fluorophenyl) thiazole.

Compounds of Reference Examples 10-40 as shown in Table 4 were synthesized employing each corresponding starting material, in the same manner as described in Reference Example 9.

REFERENCE EXAMPLE 41

To a solution of 0.5g of the compound of Reference Example 1 in 5 ml of DMF, 0.45 g of N-bromosuccinimide was added under ice cooling, and the mixture was stirred at the same temperature for 50 minutes. To the reaction mixture, 0.6 g of cyclohexylpiperazine and 0.6 ml of triethylamine were sequentially added, and the mixture was stirred at 70° C. for 3 days. The solvent was evaporated under reduced pressure, chloroform was added to the residue, and then the organic layer was washed with aqueous potassium carbonate and brine, and dried over sodium sulfate. The residue obtained by the evaporation of the solvent under reduced pressure was purified by silica gel column chromatography (elute:hexane-EtOAc=1:1) to obtain 300 mg of 2-amino-4-(4-chlorothiophen-2-yl)-5-(4-cyclohexylpiperazin-1-yl) thiazole.

Compounds of Reference Examples 42-71 as shown in Table 4 were synthesized employing each corresponding starting material, in the same manner as described in Reference Example 41.

TABLE 4

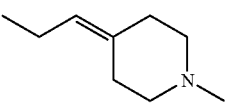

| Rf | $R^1$ | $R^2$ | Data |
|---|---|---|---|
| 9 | 4-F—Ph | 4-cHex-pipa | MS; 361. |
| 10 | 4-F—Ph | 4-nPr-pipe | MS; 320. |
| 11 | 4-$F_3$C—Ph | 4-cHex-pipa | MS; 411. |
| 12 | 4-$O_2$N—Ph | 4-cHex-pipa | MS; 388. |
| 13 | 4-$Me_2$N—Ph | 4-cHex-pipa | MS; 386. |
| 14 | 4-cyano-Ph | 4-cHex-pipa | MS; 368. |
| 15 | 4-$EtO_2$C—Ph | 4-cHex-pipa | MS; 415. |
| 16 | 3-$F_3$C—Ph | 4-cHex-pipa | MS; 410. |
| 17 | 3-cyano-Ph | 4-cHex-pipa | MS; 368. |
| 18 | 4-F—Ph | 4-nPrO-pipe | MS; 336. |
| 19 | 4-F—Ph | 4-mor-pipe | MS; 363. |
| 20 | 5-Cl-2-The | (structure) | MS; 339. |
| 21 | 5-Me-2-Fur | 4-cHex-pipa | MS; 347. |
| 22 | 3-Cl-2-The | 4-cHex-pipa | MS; 383. |
| 23 | S-Cl-3-The | 4-cHex-pipa | MS; 383. |
| 24 | 5-Cl-2-The | 4-cHex-pipa | MS; 383. |
| 25 | 5-Br-2-The | 4-cHex-pipa | MS; 427, 429. |
| 26 | 5-Me-2-The | 4-cHex-pipa | MS; 363. |
| 27 | 3-F-2-The | 4-cHex-pipa | MS; 367. |

TABLE 4-continued

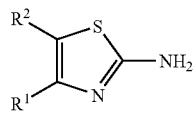

| Rf | R¹ | R² | Data |
|---|---|---|---|
| 28 | 5-Cl-2-The | 4-nPr-pipe | MS; 342. |
| 29 | 4-F—Ph | (MeO(CH₂)₂)(Me)N— | MS; 282. |
| 30 | 4-F—Ph | ((cHex)(Me)N(CH₂)₂)(Me)N— | MS; 363. |
| 31 | 4-F—Ph | (Me₂N(CH₂)₂)(Me)N— | MS; 295. |
| 32 | 4-F—Ph | (Me₂N(CH₂)₃)(Me)N— | MS; 309. |
| 33 | 4-F—Ph | (pipe-(CH₂)₂)(Me)N— | MS; 335. |
| 34 | 4-F—Ph | 4-AcHN-4-Ph-pipe | MS; 411. |
| 35 | 4-F—Ph | imid | MS; 261. |
| 36 | 4-F—Ph | 4-Ph-imid | MS; 337. |
| 37 | 4-F—Ph | 4-BnO₂C-pipa | MS; 413. |
| 38 | 4-F—Ph | 4-nBu-2,5-diMe-pipa | MS; 362. |
| 39 | 4-F—Ph | 3-(1-pipe)-azet | MS; 333. |
| 40 | 3-Cl—Ph | 4-cHex-pipa | MS; 377. |
| 41 | 4-Cl-2-The | 4-cHex-pipa | MS; 383. |
| 42 | 5-F-2-The | 4-cHex-pipa | MS; 367. |
| 43 | 4-Br-2-The | 4-cHex-pipa | MS; 427, 429. |
| 44 | 4-Me-2-The | 4-cHex-pipa | MS; 363. |
| 45 | 4-Cl-2-The | 4-nPr-pipe | MS; 342. |
| 46 | 4-Cl-2-The | (1-nBu-piperidin-4-yl)(Me)N— | MS; 385. |
| 47 | 4-Cl-2-The | 4-(allylO₂C)-pipa | MS; 385. |
| 48 | 4-Cl-2-The | 3-(4-nPr-1-pipe)-azet | MS; 397. |
| 49 | 4-Cl-2-The | 4-mor-pipe | MS; 385. |
| 50 | 4-Cl-2-The | (1-nBu-pyrrolidin-3-yl)(Me)N— | MS; 371. |
| 51 | 4-Cl-2-The | (quinuclidin-3-yl)(Me)N— | MS; 355. |
| 52 | 4-F-5-Cl-2-The | 4-cHex-pipa | MS; 401. |
| 53 | 4-Cl-2-The | 4-nPr-pipa | MS; 343. |
| 54 | 4-Cl-2-The | mor | MS; 302. |
| 55 | 4-F-2-The | 4-cHex-pipa | MS; 367. |
| 56 | 4-Cl-2-The | (mor-(CH₂)₃)(Me)N— | MS; 373. |
| 57 | 4-Cl-2-The | (mor-(CH₂)₂)(cHex)N— | MS; 427. |
| 58 | 4-Cl-2-The | 4-tmor-pipe | MS; 401. |
| 59 | 4-Cl-2-The | tmor | MS; 318. |
| 60 | 4-Cl-2-The | 3-oxo-pipa | MS; 315. |
| 61 | 4-Cl-2-The | 4-(cHex)(Me)N-pipe | MS; 411. |
| 62 | 4,5-diCl-2-The | 4-cHex-pipa | MS; 417. |
| 63 | 4-Cl-2-The | 4-pipe-pipe | MS; 383. |
| 64 | 4-Cl-2-The | 4-(F₃C—CH₂)(Me)N-pipe | MS; 411. |
| 65 | 4-Cl-2-The | (3R*,5S*)-3,5-diMe-4-nPr-pipa | MS; 371. |
| 66 | 4-Cl-2-The | 4-cHep-pipa | MS; 397. |
| 67 | 4-Cl-2-The | 4-(nPr)(Me)N-pipe | MS; 371. |
| 68 | 4-Cl-2-The | 4-(F₃C—(CH₂)₂)(Me)N-pipe | MS; 425. |
| 69 | 4-Cl-2-The | 3-EtO₂C-pipe | MS; 372. |
| 70 | 4-Cl-2-The | 2-EtO₂C-pipe | MS; 372. |
| 71 | 4-Cl-2-The | 4-(3-F-pyrr)-pipe | MS; 387. |

REFERENCE EXAMPLE 72

To a solution of 830 mg of the compound of Reference Example 69 in 2 ml of EtOH, 6 ml of 1M NaOH aq. was added, and the mixture was stirred at room temperature overnight. The solvent was evaporated, and the residue was mixed with water and extracted with diethylether. 6.5 ml of 1M HCl aq. was added to the remaining aqueous layer, and the resulting precipitate was collected by filtration and dried under reduced pressure to obtain 726 mg of 1-[2-amino-4-(4-chlorothiophen-2-yl)thiazol-5-yl]piperidine-3-carboxylic acid.

Compounds of Reference Example 73 as shown in Table 5 were synthesized employing each corresponding starting material, in the same manner as described in Reference Example 72.

TABLE 5

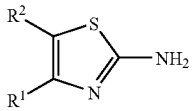

| Rf | R¹ | R² | Data |
|---|---|---|---|
| 72 | 4-Cl-2-The | 3-HO₂C-pipe | MS; 344. |
| 73 | 4-Cl-2-The | 2-HO₂C-pipe | MS; 344. |

REFERENCE EXAMPLE 74

To a solution of 683 mg of the compound of Reference Example 72 in 20 ml of DMF, 359 mg of 1-hydroxybenzotriazole (HOBO, 506 mg of WSC.HCl 432 mg of dimethylamine hydrochloride, and 1.11 ml of triethylamine were added, and the mixture was stirred at room temperature overnight. The solvent was evaporated under reduced pressure, and saturated NaHCO₃ aq. was added to the residue. The produced precipitate was collected by filtration and dissolved in chloroform, and the reaction solution was mixed with saturated NaHCO₃ aq. and extracted with chloroform. After drying over MgSO₄, the solvent was evaporated, and the thus-obtained residue was purified by silica gel column chromatography using chloroform: MeOH (100:1~50:1) as an eluent to obtain 628 mg of 14[2-amino-4-(4-chlorothiophen-2-yl)]-N,N-dimethylpiperidine-3-carboxamide.

The compound of Reference Example 75 as shown in Table 6 was synthesized employing corresponding starting material, in the same manner as described in Reference Example 74.

TABLE 6

| Rf | R¹ | R² | Data |
|---|---|---|---|
| 74 | 4-Cl-2-The | 3-Me₂NOC-pipe | MS; 371. |
| 75 | 4-Cl-2-The | 2-Me₂NOC-pipe | MS; 371. |

REFERENCE EXAMPLE 76

A solution of 608 mg of the compound of Reference Example 74 in 10 ml of THF was added to a suspension of 143 mg of LAH in 10 ml of THF, and the mixture was heated under reflux overnight. The reaction solution was cooled to room temperature, and 0.14 ml of water, 0.14 ml of 2M NaOH aq., and 0.42 ml of water were added thereto. The thus-produced precipitate was removed by filtration, the solvent was evaporated under reduced pressure, and the thus-obtained residue was purified by silica gel column chromatography using chloroform:MeOH (20:1) as an eluent to obtain 156 mg of 2-amino-4-(4-chlorothiophen-2-yl)-5-{3-[(dimethylamino)methyl]piperidin-1-yl}thiazole.

The compound of Reference Example 77 as shown in Table 7 was synthesized employing corresponding starting material, in the same manner as described in Reference Example 76.

TABLE 7

| Rf | R¹ | R² | Data |
|---|---|---|---|
| 76 | 4-Cl-2-The | 3-(Me$_2$N—CH$_2$)-pipe | MS; 357. |
| 77 | 4-Cl-2-The | 2-(Me$_2$N—CH$_2$)-pipe | MS; 357. |

REFERENCE EXAMPLE 78

To a solution of 2.50 g of 3-chloro-4-hydroxybenzoic acid methyl ester in 25 ml of DMF, 2.78 g of potassium carbonate and 4.31 ml of 2-(tert-butyldimethylsilyloxy)ethylbromide were added, and the mixture was stirred at 50° C. for 15 hours. The solvent was evaporated, EtOAc was added to the residue, and the organic layer was washed with water and brine and dried over sodium sulfate. After the evaporation of the solvent, the obtained residue was purified by silica gel column chromatography (eluent: hexane-EtOAc=10:1~5:1) to obtain 4.88 g of 4-[2-(tert-butyldimethylsilyloxy)ethoxy]-3-chlorobenzoic acid methyl ester.

Compounds of Reference Examples 79-89 were synthesized employing each corresponding starting material, in the same manner as described in Reference Example 78.

REFERENCE EXAMPLE 90

To a solution of 1.5 g of 3-chloro-4-hydroxybenzoic acid methyl ester in 20 ml of THF, 1.8 ml of 1-tert-butoxy-2-propanol, 3.16 g of triphenylphosphine, and 1.9 ml of diethylazodicarboxylate were added, and the mixture was stirred at room temperature for 1 hour. After evaporation of the solvent under reduced pressure, the obtained residue was purified by silica gel column chromatography (eluent: hexane-EtOAc=100:1~5:1) to obtain 2.3 g of 4-(1-tert-butoxy-2-propoxy)-3-chlorobenzoic acid methyl ester.

Compounds of Reference Examples 91.93 as shown in Table 8 were synthesized employing each corresponding starting material in the same manner as described in Reference Example 90.

REFERENCE EXAMPLE 94

4.0 g of 6-quinolinecarboxylic acid were suspended in 30 ml of MeOH, 2.0 ml of conc. sulfate was added under ice cooling, and the mixture was stirred at 70° C. for 22 hours. The reaction solution was concentrated under reduced pressure, and the residue was mixed with water and neutralized with potassium carbonate. The thus-precipitated solid was filtered and dried to obtain 4.28 g of 6-quinolinecarboxylic acid methyl ester. 0.5 g of the obtained ester body was dissolved in 5 ml of formamide, 0.15 ml of conc. sulfate, 0.05 g of ferrous sulfate hepta-hydrate, and 0.4 ml of 31% hydrogen peroxide were sequentially added thereto, and the mixture was stirred at 80° C. for 50 minutes. The reaction solution was mixed with water and alkalinized with potassium carbonate. 10% MeOH-chloroform was added, and insoluble matter was filtered using celite. The obtained filtrate was separated, the obtained organic layer was dried over anhydrous sodium sulfate and concentrated, and the obtained residue was washed with EtOH to obtain 0.15 g of 6-methoxycarbonyl-2-quinolinecarboxamide.

REFERENCE EXAMPLE 95

To a solution of 1.96 g of 5-methylpyrazole-3-carboxylic acid ethyl ester in 40 ml of DMF, 2.64 g of potassium carbonate and 3.53 ml of 3-(tert-butyldimethylsilyloxy)propylbromide were added, and the mixture was stirred at 50° C. for 18 hours. The solvent was evaporated, EtOAc was added to the residue, and the organic layer was washed with water and brine and dried over sodium sulfate. After the evaporation of the solvent, the obtained residue was purified by silica gel column chromatography (eluent:hexane-EtOAc=15:1~5:1) to obtain 1.39 g of 1-[3-(tert-butyldimethylsilyloxy)propoxy]-5-methylpyrazole-3-carboxylic acid ethyl ester.

REFERENCE EXAMPLE 96

To a solution of 0.50 g of 3-chloro-4-formylbenzoic acid methylester in 10 ml of methylene chloride, 0.5 ml of acetic acid, 0.3 ml of 2-methoxyethylamine, and 0.85 g of triacetoxyborohydride were added, and the mixture was stirred at room temperature for 1 day. The reaction solution was mixed with water and neutralized with potassium carbonate, and then EtOAc was added thereto. The organic layer was washed with water and brine, and dried over sodium sulfate. The solvent was evaporated to obtain a benzyl amine body.

To a solution of the benzyl amine body in 10 ml of THF, 0.70 g of di-tert-butyldicarbonate was added, and the mixture was stirred at room temperature overnight. After the evaporation of the solvent, the obtained residue was purified by silica gel column chromatography (eluent:hexane-EtOAc=10:1~8:1) to obtain 0.87 g of N-(2-chloro-4-methoxycarbonylbenzyl)-N-(2-methoxyethyl)carbamic acid tert-butylester.

The compound of Reference Example 97 as shown in Table 8 was synthesized employing corresponding starting material, in the same manner as described in Reference Example 96.

REFERENCE EXAMPLE 98

To a solution of 1.52 g of 3,4,5-trifluorobenzoic acid in 15 ml of dichloromethane, 0.92 ml of oxalyl chloride was added under ice cooling, and the mixture was stirred at the same temperature for 30 minutes and at room temperature for 80 minutes. After DMF was added dropwise, the mixture was stirred at room temperature for 1 hour. To the residue obtained by the evaporation of the solvent under reduced pressure, 20 ml of pyridine, 3.40 ml of 2-tert-butoxyethanol, and 1 fold by spatula of DMAP were added under ice cooling, and the mixture was stirred at room temperature overnight. After the evaporation of the solvent under reduced pressure, the residue was mixed with saturated NaHCO$_3$ aq. extracted with EtOAc, washed with water and brine, and dried over MgSO$_4$. The solvent was evaporated under reduced pressure to obtain 2.10 g of crude 3,4,5-trifluorobenzoic acid 2-tert-butoxyethyl ester. To a solution of 1.03 g of potassium tert-butoxide in 15 ml of THF, 1.50 ml of 2-tert-butoxyethanol was added, and the mixture was stirred for 40 minutes. The reaction solution was cooled to −78° C., a solution of 2.10 g of crude 3,4,5-trifluorobenzoic acid 2-tert-butoxyethylester in 5 ml of THF was added thereto, and the mixture was stirred under ice cooling for 1 hour and at room temperature for 30 minutes. The reaction solution was mixed with saturated aqueous ammonium chloride, extracted with EtOAc, and washed with water and brine, and then dried over MgSO$_4$. The residue obtained by the evaporation of the solvent under reduced pressure was purified by silica gel column chromatography (eluent: hexane-EtOAc=100:1~20:1) to obtain 2.24 g of 4-(2-tert-butoxyethoxy)-3,5-difluorobenzoic acid 2-tert-butoxyethyl ester.

REFERENCE EXAMPLE 99

To a solution of 1.15 g of 3-chloro-4-fluorobenzoic acid in 20 ml of DMSO, 1.3 g of potassium carbonate and 1.4 g of isonipecotic acid ethyl ester were added, and the mixture was heated while stirring at 80 for 2 days. EtOAc was added to the reaction solution, and the organic layer was washed with water and brine and then dried over sodium sulfate. After the evaporation of the solvent, the obtained residue was purified by silica gel column chromatography (eluent:hexane-EtOAc=20:1-10:1) to obtain 1.42 g of N-(4-tert-butoxycarbonyl-2-chloropheyl)isonipecotic acid ethyl ester.

Compounds of Reference Examples 100.108 as shown in Table 8 were synthesized employing each corresponding starting material, in the same manner as described in Reference Example 99.

REFERENCE EXAMPLE 109

To a solution of 0.70 g of 3-chloro-4-(4-hydroxypiperidino)benzoic acid in 15 ml of methylene chloride, 1.5 ml of 2,6-lutidine and 2.7 g of tert-butyldimethylsilyltriflate were added, and the mixture was stirred at room temperature for 2 weeks. To the reaction solution, EtOAc was added, and the organic layer was washed with water and brine and then dried over sodium sulfate. After the evaporation of the solvent, the obtained residue was purified by silica gel column chromatography (eluent:hexane-EtOAc=5:1~4:1) to obtain 0.90 g of 4-(4-tert-butyldimethylsilyloxypiperidino)-3-chlorobenzoic acid methyl ester.

REFERENCE EXAMPLE 110

To a solution of 1.50 g of 1-(4-ethoxycarbonyl-2-fluorophenyl)piperidine-4-carboxamide in 20 ml of THF, 2.0 ml of triethylamine and 0.9 ml of trifluoroacetic acid anhydride were added at −78° C., and the mixture was stirred at room temperature for 6 hours. The solvent was evaporated, EtOAc was added, and then the organic layer was washed with water and brine, and dried over sodium sulfate. After the evaporation of the solvent, the residue was purified by silica gel column chromatography (eluent:hexane-EtOAc=5:1~4:1) to obtain 1.43 g of 4-(4-cyanopiperidino)-3-fluorobenzoic acid ethyl ester.

REFERENCE EXAMPLE 111

To a solution of 0.50 g of N-(4-tert-butoxycarbonyl-2-fluorophenyl)isonipecotic acid ethyl ester in 5 ml of DMF, 0.21 g of N-chlorosuccinimide was added, and the mixture was stirred at room temperature for 1 day. After the evaporation of the solvent, the residue was purified by silica gel column chromatography (eluent:hexane-EtOAc=5:1~1:1) to obtain 0.51 g of N-(4-tert-butoxycarbonyl-2-chloro-6-fluorophenyl)isonipecotic acid ethyl ester.

Compounds of Reference Examples 112-113 as shown in Table 8 were synthesized employing each corresponding starting material, in the same manner as described in Reference Example 111.

TABLE 8

| Rf | structure | Data |
|----|-----------|------|
| 78 | MeO$_2$C—(phenyl, Cl)—O—CH$_2$CH$_2$—OTBS | MS; 345. |
| 79 | EtO$_2$C—(phenyl, F)—O—CH$_2$—OMe | MS; 243 |
| 80 | MeO$_2$C—(phenyl, Cl)—O—CH$_2$—OMe | MS; 245. |
| 81 | EtO$_2$C—(phenyl, Br)—O—CH$_2$CH$_2$—OTBS | MS; 403, 405. |
| 82 | EtO$_2$C—(phenyl, Cl, F)—O—CH$_2$CH$_2$—OTBS | NMR (CDCl$_3$); 0.05-0.13 (6H, m), 0.82-0.93 (9H, m), 1.40 (3H, t, J = 7.1 Hz), 3.97 (2H, t, J = 5.1 Hz), 4.28-4.34 (2H, m), 4.37 (2H, q, J = 7.1 Hz), 7.68 (1H, dd, J = 2.0, 11.6 Hz), 7.87 (1H, t, J = 2.0 Hz) |

TABLE 8-continued

| Rf | structure | Data |
|---|---|---|
| 83 | EtO₂C-[3,5-diCl-4-(OCH₂CH₂OTBS)phenyl] | MS; 393. |
| 84 | MeO₂C-[3-Cl-4-(OCH₂CH₂CH₂OTBS)phenyl] | MS; 359. |
| 85 | MeO₂C-[3-F-4-(OCH₂OMe)phenyl] | GC-MS(M)⁺; 214. |
| 86 | MeO₂C-[3-Cl-4-(OCH₂OMe)phenyl] | MS; 231. |
| 87 | EtO₂C-[3-Cl-4-(OCH₂CH₂NHC(O)OtBu)phenyl] | MS; 343. |
| 88 | EtO₂C-[3-CH₃-4-(OCH₂CH₂OTBS)phenyl] | MS; 339. |
| 89 | MeO₂C-[3-(CH₂CH₂OTBS)-2-oxo-benzoxazole] | MS; 339. |
| 90 | MeO₂C-[3-Cl-4-(OCH(CH₃)CH₂OtBu)phenyl] | MS; 301. |
| 91 | EtO₂C-[3-Cl-4-(OCH₂-tetrahydrofuran-2-yl)phenyl] | MS; 285. |

TABLE 8-continued
| Rf | structure | Data |
|---|---|---|
| 92 | 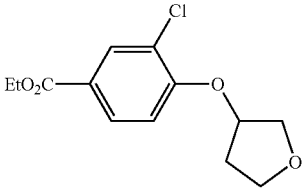 | MS; 271 |
| 93 | 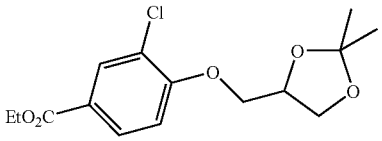 | NMR (CDCl₃); 1.38 (3H, t, J = 6.0 Hz), 1.41 (3H, s), 1.47 (3H, s), 4.00-4.23 (4H, m), 4.33 (2H, q, J = 6.0 Hz), 4.48-4.56 (1H, m), 6.96 (1H, d, J = 8.7 Hz), 7.92 (1H, dd, J = 2.0, 8.7 Hz), 8.05 (1H, d, J = 2.0 Hz). |
| 94 | 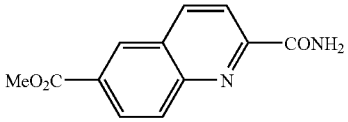 | MS; 231. |
| 95 | 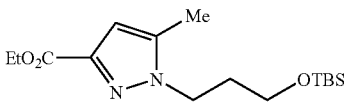 | MS; 327. |
| 96 | 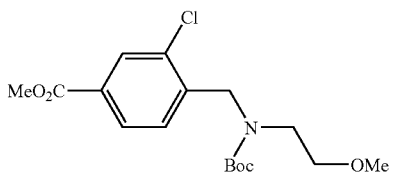 | MS; 358. |
| 97 | 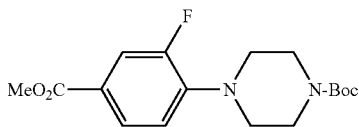 | MS; 339. |
| 98 | 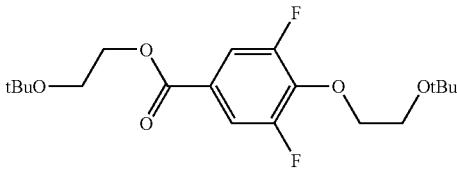 | MS; 375. |
| 99 | 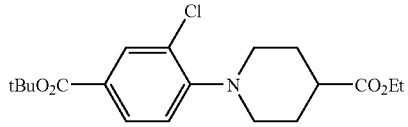 | MS; 368 |
| 100 | 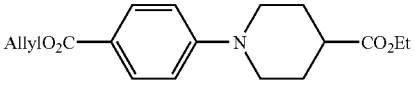 | MS; 318. |
| 101 | 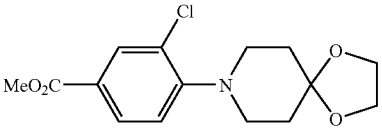 | MS; 312 |

TABLE 8-continued
| Rf | structure | Data |
|---|---|---|
| 102 | 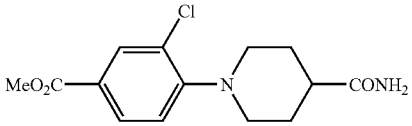 | MS; 297 |
| 103 | 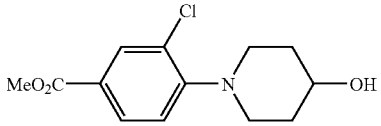 | MS; 269 |
| 104 | 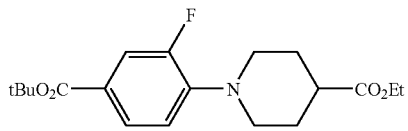 | MS; 352 |
| 105 | 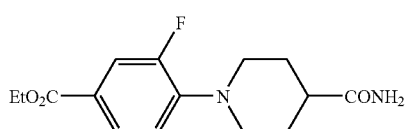 | MS; 295 |
| 106 | 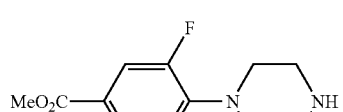 | MS; 239. |
| 107 | 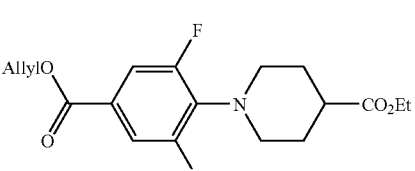 | MS; 354. |
| 108 | 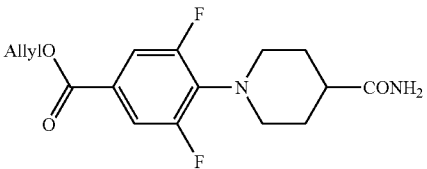 | MS; 325. |
| 109 | 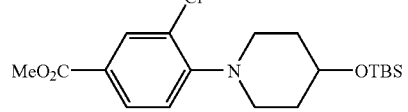 | MS; 384 |
| 110 | 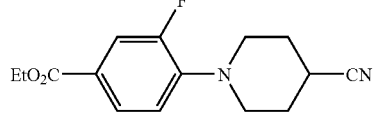 | MS; 277 |
| 111 | 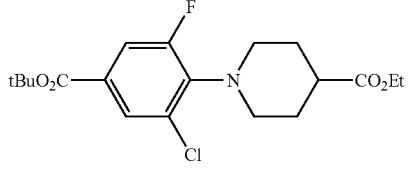 | MS; 386 |

TABLE 8-continued

| Rf | structure | Data |
|---|---|---|
| 112 | EtO₂C-C₆H₂(F)(Cl)-N(piperidine)-CN | MS; 311 |
| 113 | MeO₂C-C₆H₂(F)(Cl)-N(piperazine)-N-Boc | MS; 373. |

REFERENCE EXAMPLE 114

To a solution of 2.16 g of the compound of Reference Example 78 in MeOH 20 ml-THF 15 ml, 7.5 ml of 1M NaOH aq was added, and the mixture was stirred at room temperature for 3 days. The solvent was evaporated, and the residue was acidified with 5% potassium hydrogen sulfate aq. and extracted with chloroform-2-propanol (3:1). The organic layer was washed with brine, and dried over sodium sulfate, and then the solvent was evaporated to obtain 1.17 g of 4-[2-(tert-butyldimethylsilyloxy)ethoxyl]-3-chlorobenzoic acid.

Compounds of Reference Examples 115-138 as shown in Table 9 were synthesized employing each corresponding starting material, in the same manner as described in Reference Example 114.

REFERENCE EXAMPLE 139

To 1.56 g of 3,4,5-trifluorobenzoylchloride, 6.32 ml of 2-methoyethanol and 6.53 g of cesium carbonate were added, and the mixture was stirred at 100° C. for 20 hours. The reaction solution was mixed with 50 ml of THF and filtered, and the filtrate was evaporated to obtain 4.36 g of colorless solid. The solid was dissolved in 15 ml of THF, 3.16 ml of 2-methoxyethanol, and 1.35 g of potassium tert-butoxide were added thereto, and the mixture was stirred at room temperature for 4 days. The reaction solution was mixed with 5% potassium hydrogensulfate aq. and extracted with EtOAc. The organic layer was washed with brine and dried over sodium sulfate, and then the solvent was evaporated to obtain 1.76 g of 3,5-difluoro-4-(2-methoxyethoxy)benzoic acid.

REFERENCE EXAMPLE 140

0.3 g of the compound of Reference Example 94 was dissolved in 10 ml of a mixed solvent of THF-MeOH (1:1), 1.5 ml of 1M NaOH aq. was added at room temperature, and the mixture was stirred at the same temperature for 3 days. The reaction solution was concentrated under reduced pressure, mixed with water, and neutralized with 1.5 ml of 1M HCl aq. The thus-obtained solid was filtered and dried to obtain 0.29 g of 2-carbamoylquinoline-6-carboxylic acid.

REFERENCE EXAMPLE 141

To a solution of 410 mg of the compound of Reference Example 130 in 10 ml of pyridine, 0.24 ml of acetic acid anhydride was added, and the mixture was stirred at room temperature for 15 hours. The solvent was evaporated, EtOAc was added to the residue, and the organic layer was washed with 1M HCl, water and brine and dried over sodium sulfate. After the evaporation of the solvent, the residue was purified by silica gel column chromatography (eluent: chloroform-MeOH=100:1-50:1) to obtain 351 mg of 4-[2-(acetyloxy)ethoxy]-3-methylbenzoic acid.

The compound of Reference Example 142 as shown in Table 9 was synthesized employing each corresponding starting material, in the same manner as described in Reference Example 141.

REFERENCE EXAMPLE 143

To 2.00 g of 2-chloroisonicotic acid, 15 ml of ethyleneglycol and 4.28 g of potassium tert-butoxide were added, and the mixture was stirred at 150° C. for 6 days. The reaction solution was poured into 5% potassium hydrogen sulfate aq. and extracted with EtOAc, and then the organic layer was washed with brine and dried over MgSO₄. The solvent was evaporated to obtain 0.54 g of 2-(2-hydroxyethoxy)isonicotic acid.

REFERENCE EXAMPLE 144

To a solution of 4.74 g of 1-{4-[(allyloxy)carbonyl]phenyl}piperidine-4-carboxylic acid ethyl ester in 75 ml of THF, 2.10 ml of morpholine and 390 mg of tetrakis(triphenylphosphine)palladium were added, and the mixture was stirred at 60° C. for 1.5 hours. After the solvent was evaporated under reduced pressure, EtOAc was added to the residue, and the reaction solution was washed with NaHCO₃ aq. three times. To the collected saturated NaHCO₃ aq., conc. HCl was added, and the produced precipitate was collected by filtration and dried under reduced pressure to obtain 2.73 g of 4-[4-(Ethoxycarbonyl)piperidin-1-yl]benzoic acid.

The compound of Reference Example 145 as shown in Table 9 was synthesized employing corresponding starting material, in the same manner as described in Reference Example 144.

REFERENCE EXAMPLE 146

1.42 g of the compound of Reference Example 99 were dissolved in 5 ml of methylene chloride, 5 ml of trifluoroacetic acid were added under ice cooling, and the mixture was stirred at room temperature for 1 day. The reaction solution was concentrated under reduced pressure, mixed with water, and neutralized with NaOH aq. The obtained solid was filtered and dried to obtain 1.16 g of 3-chloro-4-(4-ethoxycarbonylpiperidino)benzoic acid.

The compound of Reference Example 147 as shown in Table 9 was synthesized employing corresponding starting material, in the same manner as described in Reference Example 146.

REFERENCE EXAMPLE 148

To a solution of 1.12 g of the compound of Reference Example 144 in 20 ml of DMF, 775 mg of N-bromosuccinimide were added, and the mixture was stirred at room temperature for 70 minutes and at 50° C. for 2 hours. After the solvent was evaporated under reduced pressure, water was added to the residue, and the produced precipitate was collected by filtration. After adding saturated NaHCO3 aq., EtOAc, and HCl, the reaction solution was extracted with chloroform, and dried over MgSO4. The residue obtained by the evaporation of the solvent under reduced pressure was purified by silica gel column chromatography (eluent:chloroform-methanol=100:1~30:1) to obtain 1.29 g of 3-bromo-4-[4-(ethoxycarbonyl(piperidin-1-yl)benzoic acid.

TABLE 9

| Rf | structure | Data |
|---|---|---|
| 114 | (HO2C-phenyl(Cl)-O-CH2CH2-OTBS) | MN; 329. |
| 115 | (HO2C-phenyl(F)-O-CH2CH2-OMe) | MN; 213. |
| 116 | (HO2C-phenyl(Cl)-O-CH2CH2-OMe) | MN; 229. |
| 117 | (HO2C-phenyl(Br)-O-CH2CH2-OTBS) | MN; 373, 375. |
| 118 | (HO2C-phenyl(Cl,F)-O-CH2CH2-OTBS) | NMR (CDCl$_3$); 0.05-0.15 (6H, m), 0.85-0.92 (9H, m), 3.97 (2H, t, J = 5.2 Hz), 4.32-4.37 (2H, m), 7.73 (1H, dd, J = 2.0, 11.2 Hz), 7.93 (1H, t, J = 2.0 Hz). |
| 119 | (HO2C-phenyl(Cl,Cl)-O-CH2CH2-OTBS) | MN; 363. |
| 120 | (HO2C-phenyl(Cl)-O-CH2CH2CH2-OTBS) | MN; 343. |

TABLE 9-continued

| Rf | structure | Data |
|---|---|---|
| 121 | 3-chloro-4-(1-(tert-butoxymethyl)ethoxy)benzoic acid | MS; 287. |
| 122 | 3-fluoro-4-(methoxymethoxy)benzoic acid | MN; 199. |
| 123 | 3-chloro-4-(methoxymethoxy)benzoic acid | MS; 217. |
| 124 | 5-methyl-1-(3-(TBSoxy)propyl)pyrazole-3-carboxylic acid | MN; 297. |
| 125 | 3-chloro-4-((tetrahydrofuran-2-yl)methoxy)benzoic acid | MS; 257. |
| 126 | 3-chloro-4-((tetrahydrofuran-3-yl)oxy)benzoic acid | MN; 241 |
| 127 | 3-chloro-4-((2,2-dimethyl-1,3-dioxolan-4-yl)methoxy)benzoic acid | NMR (CDCl$_3$); 1.41 (3H, s), 1.48 (3H, s), 4.00-4.25 (4H, m), 4.49-4.58 (1H, m), 6.99 (1H, d, J = 8.7 Hz), 7.99 (1H, dd, J = 2.0, 8.7 Hz), 8.12 (1H, d, J = 2.0 Hz). |
| 128 | 3-chloro-4-(2-(Boc-amino)ethoxy)benzoic acid | MS; 316. |
| 129 | 3-chloro-4-((Boc-(2-methoxyethyl)amino)methyl)benzoic acid | MN; 342 |
| 130 | 3-methyl-4-(2-hydroxyethoxy)benzoic acid | NMR (CD$_3$OD); 2.17 (3H, s), 3.77-3.85 (2H, m), 3.97-4.06 (2H, m), 6.86 (1H, d, J = 8.7 Hz), 7.68-7.78 (2H, m). |

TABLE 9-continued
| Rf | structure | Data |
|---|---|---|
| 131 | 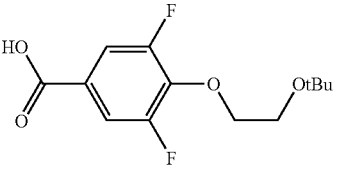 | MN; 273. |
| 132 | 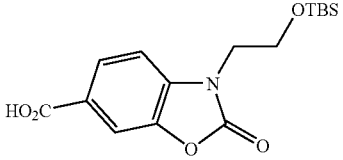 | MS; 338. |
| 133 | 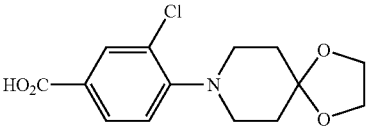 | MN; 296 |
| 134 | 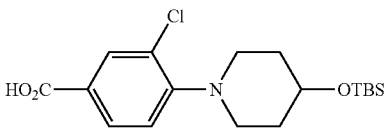 | MN; 368 |
| 135 | 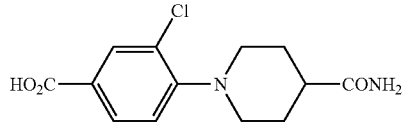 | MN; 281 |
| 136 | 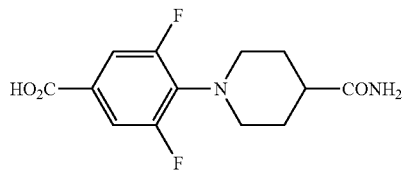 | MS; 285. |
| 137 | 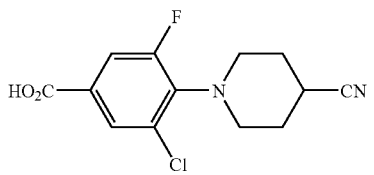 | MN; 281 |
| 138 | 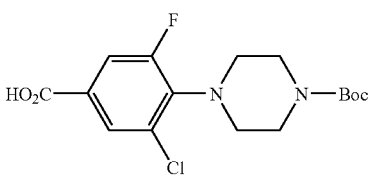 | MS; 359. |
| 139 | 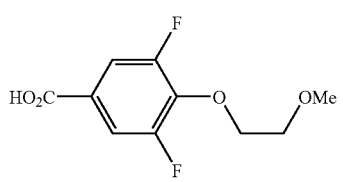 | MN; 231. |

TABLE 9-continued

| Rf | structure | Data |
|---|---|---|
| 140 | HO2C-naphthalene-CONH2 | MN; 215. |
| 141 | HO2C-(3-CH3,4-OCH2CH2OAc)phenyl | MS; 239. |
| 142 | HO2C-pyridine-2-OCH2CH2OAc | MS; 226. |
| 143 | HO2C-pyridine-2-OCH2CH2OH | NMR; 3.72 (2H, t, J = 5.0 Hz), 4.31 (2H, t, J = 5.0 Hz), 4.82 (1H, brs), 7.18 (1H, d, J = 1.3 Hz), 7.38 (1H, dd, J = 5.1, 1.3 Hz), 8.31 (1H, d, J = 5.1 Hz), 13.56 (1H, brs). |
| 144 | HO2C-C6H4-N(piperidine)-CO2Et | MS; 278. |
| 145 | HO2C-(2,6-diF)C6H2-N(piperidine)-CO2Et | MS; 314. |
| 146 | HO2C-(2-Cl)C6H3-N(piperidine)-CO2Et | MN; 310. |
| 147 | HO2C-(2-F,6-Cl)C6H2-N(piperidine)-CO2Et | MN; 328 |
| 148 | HO2C-(2-Br)C6H3-N(piperidine)-CO2Et | MN; 354, 356. |

REFERENCE EXAMPLE 149

To a solution of 2.00 g of the compound of Reference Example 9 and 1.14 g of 4-formylbenzoic acid in 30 ml of DMF, 992 mg of N-hydroxybenzotriazole (HOBO and 1.39 g of WSC.HCl were added, and the mixture was stirred at room temperature overnight. After the evaporation of the solvent under reduced pressure, the residue was mixed with saturated NaHCO$_3$ aq. and extracted with chloroform, and then the organic layer was dried over MgSO$_4$. The residue obtained by the evaporation of the solvent was purified by silica gel column chromatography twice using chloroform:methanol (100:1~30:1) and hexane:EtOAc (5:1~1:1) as eluent to obtain 1.32 g of N-[5-(4-cyclohexylpiperazin-1-yl)-4-(4-fluorophenyl)thiazol-2-yl]-4-formylbenzamide.

The compound of Reference Example 150 as shown in Table 10 was synthesized employing corresponding starting material, in the same manner as described in Reference Example 149.

TABLE 10

| Rf | structure | Data |
|---|---|---|
| 149 | (cyclohexyl-piperazinyl)-(4-fluorophenyl)thiazol-2-yl NH-C(O)-C6H4-CHO | MS; 493. |
| 150 | (cyclohexyl-piperazinyl)-(4-EtO2C-phenyl)thiazol-2-yl NH-C(O)-(2-OMe-pyridin-4-yl) | MS; 550. |

EXAMPLE 1

To a solution of 300 mg of the compound of Reference Example 9 in 5 ml of pyridine, 280 mg of 4-cyanobenzoyl-chloride were added under ice cooling, the temperature was elevated to room temperature, and then the mixture was stirred at the same temperature for 3 days and then at 50° C. for 1 day. The solvent was evaporated under reduced pressure, the residue was mixed with chloroform, and the organic layer was washed with saturated aqueous NaHCO$_3$ and brine and dried over sodium sulfate. After the evaporation of the solvent under reduced pressure, the obtained residue was recrystallized from EtOAc to obtain 230 mg of N-[5-(4-cyclohexypiperazin-1-yl)-4-(4-fluorophenyl)thiazol-2-yl]-4-cyanobenzamide. To a solution of 80 mg of the obtained compound in 5 ml of EtOAc, 0.4 ml of a solution of 0.4 M HCl-EtOAc were added, and the mixture was stirred overnight and filtered to obtain 57 mg of N-[5-(4-cyclohexylpiperazin-1-yl)-4-(4-fluorophenyl)thiazol-2-yl]-4-cyanobenzamide hydrochloride.

EXAMPLE 2

To a solution of 500 mg of the compound of Reference Example 24 in 10 ml of DMF, 300 mg of 2-methoxyisonicotinic acid, 376 mg of WSC.HCl, and 265 mg of HOBt were added, and the mixture was stirred at room temperature for 4 days. The solvent was evaporated, and the residue was mixed with EtOAc and washed with saturated aqueous NaHCO$_3$ and brine and then dried over sodium sulfate. After the evaporation of the solvent, the residue was purified by silica gel column chromatography (hexane-EtOAc=8:1~2:1) and dissolved in 10 ml of EtOAc, 0.46 ml of 0.4M HCl-EtOAc solution were added thereto, and the mixture was stirred for a while, and then the produced precipitate was collected by filtration to obtain 72 mg of N-[4-(5-chlorothiophen-2-yl)-5-(4-cyclohexylpiperazin-1-yl)thiazol-2-yl]-2-methoxyisonicotinamide hydrochloride.

EXAMPLE 3

To a solution of 342 mg of the compound of Reference Example 28 in 10 ml of DMF, 306 mg of 2-methoxyisonicotinic acid, 383 mg of WSC.HCl, 270 mg of HOBt, and 244 mg of 4-(dimethylamino)pyridine were added, and the mixture was stirred at 50° C. for 3 days. The solvent was evaporated, and the residue was mixed with EtOAc, washed with saturated aqueous NaHCO$_3$ and brine, and dried over sodium sulfate. After the evaporation of the solvent, the residue was purified by silica gel column chromatography (hexane-EtOAc=8:1) and dissolved in 30 ml of EtOAc, 4.1 ml of 0.1M HCl-EtOAc solution was added thereto, and the mixture was stirred for a while, and then the produced precipitate was collected by filtration to obtain 120 mg of N-[4-(5-chlorothiophen-2-yl)-5-(4-propylpiperidin-1-yl)thiazol-2-yl]-2-methoxyisonicotinamide hydrochloride.

EXAMPLE 4

To a solution of 1.72 g of the compound of Reference Example 78 in a mixed solvent of MeOH 17 ml-THF 10 ml, 6 ml of 1M NaOH aq. was added, and the mixture was stirred at room temperature for 3 days. To the reaction solution, 5.5 ml of 1M HCl aq. was added, and solvent was evaporated under reduced pressure to obtain a crude product of 4-[2-(tert-butyldimethylsilyloxy)ethoxy]-3-chlorobenzoic acid. To the obtained crude product, 720 mg of the compound of Reference Example 78, 20 ml of DMF, 959 mg of WSC.HCl, 676 mg of HOBt, and 611 mg of 4-(dimethylamino)pyridine were added, and the mixture was stirred at 50° C. for 22 hours and then at 90° C. for 20 hours. The solvent was evaporated, the residue was mixed with saturated aqueous NaHCO$_3$ and extracted with EtOAc, and the organic layer was washed with saturated aqueous NaHCO$_3$ and brine and dried over sodium sulfate. After the evaporation of the solvent, the residue was purified by silica gel column chromatography using chloroform-MeOH (100:1~10:1) as an eluent and silica gel column chromatography using hexane:EtOAc (2:1~1:1) as an eluent to obtain 38 mg of 3-chloro-4-{2-[3-chloro-4-(2-hydroxy-ethoxy)benzoyloxy]ethoxy}-N-[5-(4-cyclohexylpiperazin-1-yl)-4-(4-fluorophenyl)thiazol-2-yl]benzamide. To the obtained compound, 0.5 ml of MeOH, 1 ml of THF, and 225 µl of 1M NaOH aq. were added, and the mixture was stirred at room temperature for 5 days. The reaction solution was mixed with EtOAc, washed with saturated aqueous NaHCO₃ and brine, and dried over sodium sulfate. After the evaporation of the solvent, the residue was purified by silica gel chromatography (chloroform-MeOH=100:0~100:2) and the obtained product was dissolved in 5 ml of EtOAc, 1.0 ml of 0.1 M HCl-EtOAc solution was added, the mixture was stirred for a while, and the produced precipitate was collected by filtration to obtain 18 mg of 3-chloro-N-[5-(4-cyclohexylpiperazin-1-yl)-4-(4-fluorophenyl)thiazol-2-yl]-4-(2-hydroxyethoxy)benzamide hydrochloride.

EXAMPLE 5

To a solution of 1.0 g of the compound of Reference Example 41 in 30 ml of pyridine, 602 mg of 5,6-dichloronicotinic acid was added, 0.27 ml of phosphorous oxychloride was added at −25° C., and the temperature was elevated to room temperature, and then the mixture was stirred for 4 hours. The solvent was evaporated under reduced pressure, the residue was mixed with water and potassium carbonate and extracted with chloroform, and the organic layer was washed with brine and dried over sodium sulfate. After the evaporation of the solvent, the obtained residue was purified by silica gel column chromatography (hexane-EtOAc=200: 1~100:1) to obtain 1.21 g of 5,6-dichloro-N-[4-(4-chlorothiophen-2-yl)-5-(4-cyclohexylpiperazin-1-yl)thiazol-2-yl]nicotinamide.

EXAMPLE 6

To a solution of 100 mg of the compound of Example 246 in 5 ml of EtOH, 0.2 ml of 4M HCl-EtOAc solution was added, and the mixture was stirred for 27 hours. To the reaction solution, chloroform was added, and the organic layer was washed with saturated aqueous NaHCO₃ and brine and dried over sodium sulfate. After the evaporation of the solvent, the obtained residue was purified by silica gel column chromatography (chloroform-MeOH=100:1~5:1) and the obtained product was dissolved in 15 ml of MeOH, 10 ml of 4M HCl-EtOAc solution was added thereto, and the mixture was stirred for a while. Then, the solvent was evaporated under reduced pressure, and the residue was washed with diethylether to obtain 28 mg of 5-chloro-N-[4-(4-chlorothiophen-2-yl)-5-(4-cyclohexylpiperazin-1-yl)thiazol-2-yl]-6-hydroxynicotinamide hydrochloride.

EXAMPLE 7

To 183 mg of the compound of Example 233, 5 ml of trifluoroacetic acid was added, and the mixture was stirred for 40 hours. Then, the solvent was evaporated under reduced pressure, and the obtained residue was purified by silica gel column chromatography (chloroform-MeOH=100:1~20:1) to obtain 50 mg of 3-chloro-N-[4-(4-chlorothiophen-2-yl)-5-(4-cyclohexylpiperazin-1-yl)thiazol-2-yl]-4-(1-hydroxy-2-propoxy)benzamide trifluoroacetate.

EXAMPLE 8

0.34 g of the compound of Example 218 was suspended in 5 ml of MeOH, 1 ml of conc. HCl was added thereto under ice cooling, and the mixture was stirred at 50° C. overnight. To the reaction solution, 0.5 ml of conc. HCl was added again, and the mixture was stirred at 50° C. for 5 hours and 60° C. overnight. The reaction solution was cooled to room temperature, and the thus-precipitated solid was filtered and dried to obtain 0.33 g of N-[4-(4-chlorothiophen-2-yl)-5-(4-cyclohexylpiperazin-1-yl)thiazol-2-yl]-3-fluoro-4-hydroxybenzamide hydrochloride.

EXAMPLE 9

187 mg of the compound of Example 230 was dissolved in 10 ml of MeOH, 3.5 ml of conc. HCl was added, and the mixture was stirred for 18 hours. Then, the thus-produced precipitate was filtered and washed with diethylether to obtain 90 mg of 3-chloro-N-[4-(4-chlorothiophen-2-yl)-5-(4-cyclohexylpiperazin-1    -yl)thiazol-2-yl]-4-(2-hydroxyethoxy)benzamide hydrochloride.

EXAMPLE 10

To a solution of 5.23 g of the compound of Example 101 in 100 ml of THF, 17.0 g of tributyltin hydride was added at 0° C., and the mixture was cooled to −78° C. And, 670 mg of tetrakis(triphenylphosphine)palladium was added thereto, the temperature was slowly elevated to room temperature, and the mixture was stirred for 1.5 hours. The reaction solution was mixed with 1.6 ml of acetic acid and stirred at room temperature for 15 minutes. Then, the solvent was evaporated under reduced pressure, hexane was added to the obtained residue, and the thus-formed precipitate was collected by filtration and dried under reduced pressure to obtain 4.30 g of N-[4-(4-chlorothiophen-2-yl)-5-(piperazin-1-yl)thiazol-2-yl]-2-methoxyisonicotinamide acetate.

EXAMPLE 11

0.15 g of the compound of Example 136 was dissolved in 5.0 ml of THF, a total 1.3 ml of butyl lithium (1.55 M) was added thereto at −78° C., and the mixture was stirred at the same temperature for 4.5 hours to confirm the loss of the starting material. 0.5 ml of acetic acid was added to the reaction solution to stop the reaction, and the temperature was elevated to room temperature. The reaction solution was mixed with water, alkalinized with potassium carbonate, and extracted with chloroform. The organic layer was dried over anhydrous sodium sulfate, and the solvent was concentrated under reduced pressure. The thus-obtained residue was purified by silica gel column chromatography to obtain 0.12 g of N-[5-(4-cyclohexylpiperazin-1-yl)-4-(thiophen-2-yl)thiazol-2-yl]-2-methoxyisonicotinamide. The obtained compound was dissolved in 2 ml of EtOAc, 0.25 ml of 1M HCl-EtOAc solution was added thereto under ice cooling, and the mixture was stirred at room temperature overnight. The thus-precipitated solid was filtered and dried to obtain 98 mg of N-[5-(4-cyclohexylpiperazin-1-yl)-4-(thiophen-2-yl)thiazol-2-yl]-2-methoxyisonicotinamide hydrochloride.

EXAMPLE 12

To a solution of 48 mg of 40% sodium hydride in 1 ml of ethyleneglycol, 100 mg of the compound of Example 5 was added at room temperature, the temperature was elevated to 50° C., and the mixture was stirred for 4 days. To the reaction solution, chloroform was added, and the organic layer was washed with saturated aqueous NaHCO₃ and brine and dried over sodium sulfate. After the evaporation of the solvent under reduced pressure, the obtained residue was purified by silica gel column chromatography (chloroform-MeOH=200: 1~20:1) and the obtained compound was dissolved in 5 ml of EtOAc, 0.8 ml of 0.1M HCl-EtOAc solution was added thereto, and the mixture was stirred for a while. Then, the solvent was evaporated under reduced pressure, and the residue was washed with diethylether to obtain 34 mg of 5-chloro-N-[4-(4-chlorothiophen-2-yl)-5-(4-cyclohexylpiperazin-1-yl)thiazol-2-yl]-6-(2-hydroxyethoxy)nicotinamide hydrochloride.

EXAMPLE 13

To a solution of 750 mg of the compound of Example 5 in 10 ml of THF, 2.1 ml of ethyl isonipecotate was added at room temperature, the temperature was elevated to 50° C., and the mixture was stirred for 5 hours. To the reaction solution, chloroform was added, and the organic layer was washed with saturated aqueous NaHCO$_3$ and brine and dried over sodium sulfate. After the evaporation of the solvent under reduced pressure, the obtained residue was purified by silica gel column chromatography (chloroform-MeOH=200:1~100:1) to obtain 881 mg of 1-(3-chloro-5-{[4-(4-chlorothiophen-2-yl)-5-(4-cyclohexylpiperazin-1-yl)thiazol-2-yl]carbamoyl}-2-pyridyl)pipedirine-4-carboxylic acid ethyl ester.

EXAMPLE 14

231 mg of the compound of Example 10 and 80 µl of benzaldehyde were dissolved in 9 ml of 1,2-dichloroethane-9 ml of acetic acid, 210 mg of sodium triacetoxyborohydride was added thereto at 0° C., and the mixture was stirred at 0° C. for 30 minutes and at room temperature for 30 minutes. The reaction solution was alkalinized with saturated aqueous NaHCO$_3$ and 1M aqueous NaOH, and extracted with chloroform. The organic layer was dried over MgSO$_4$, and the solvent was evaporated under reduced pressure. Then, to the obtained residue, 5 ml of acetic acid, a total of 160 µl of benzaldehyde, and a total of 404 mg of sodium triacetoxyborohydride were added, and the mixture was stirred at 50° C. for 4 hours. The solvent was evaporated under reduced pressure, saturated aqueous NaHCO$_3$ was added to the obtained residue, and insoluble matter was collected by filtration. Chloroform was added thereto to dissolve it, and the solution was mixed with saturated aqueous NaHCO$_3$ and extracted with chloroform. The organic layer was dried over MgSO$_4$, and the solvent was evaporated under reduced pressure. The obtained residue was purified by silica gel column chromatography (hexane-EtOAc=4:1) and the obtained compound was dissolved in EtOAc, and then a 0.5 M HCl-EtOAc solution was added thereto, and the thus-produced precipitate was collected by filtration to obtain 64 mg of N-[5-(4-benzylpiperazin-1-yl)-4-(4-chlorothiophen-2-yl)thiazol-2-yl]-2-methoxyisonicotinamide hydrochloride.

EXAMPLE 15

To a solution of 0.35 g of the compound of Example 243 in 5 ml of EtOAc, 4M HCl-EtOAc was added under ice cooling, and the mixture was stirred at room temperature for 1 hour. The thus-precipitated solid was filtered to obtain 345 mg of 4-aminomethyl-N-[4-(4-chlorothiophen-2-yl)-5-(4-cyclohexylpiperazin-1-yl)thiazol-2-yl]benzamide hydrochloride.

EXAMPLE 16

To a solution of 30 mg of the compound of Example 13 in 1 ml of MeOH, 0.12 ml of 1M NaOH aq. was added at room temperature, and the mixture was stirred for 24 hours. After the solvent was evaporated under reduced pressure, the obtained residue was dissolved in 5 ml of EtOAc, 0.2 ml of 1M HCl was added thereto, and the mixture was stirred for a while. Then, the solvent was evaporated under reduced pressure and washed with diethylether to obtain 20 mg of 1-(3-chloro-5-{[4-(4-chlorothiophen-2-yl)-5-(4-cyclohexylpiperazin-1-yl)thiazol-2-yl]carbamoyl}pyridin-2-yl)piperidine-4-carboxylic acid hydrochloride.

EXAMPLE 17

To a suspension of 180 mg of the compound of Example 143 in 5 ml of DMF, 100 mg of 1,1'-carbonyldimidazole were added, and the mixture was stirred at room temperature for 4 hours. Then, 1 ml of 28% ammonia water was added, and the mixture was stirred at room temperature for 1.5 hours. The reaction solution was mixed with water and extracted with chloroform. The organic layer was dried over MgSO$_4$, and the solvent was evaporated under reduced pressure. The obtained residue was washed with ethanol, and suspended in EtOH. Then, 0.35 ml of 1M HCl-EtOAc solution was added thereto, the mixture was stirred overnight, and the thus-produced precipitate was collected by filtration to obtain 151 mg of N-[4-(4-fluorophenyl)-5-(4-cyclohexylpiperazin-1-yl)thiazol-2-yl]-4-carbamoylmethylbenzamide hydrochloride.

EXAMPLE 18

To 138 mg of the compound of Example 147, 3 ml of water and 3 ml of conc. HCl were added, and the mixture was stirred at 80° C. for 17 hours. The reaction solution was cooled to room temperature, and the thus-produced precipitate was collected by filtration and washed with water. 1M aqueous NaOH, MeOH, and diethylether were added thereto, and insoluble matter was removed by filtration. The obtained filtrate was extracted with diethylether, and conc. HCl was added to the aqueous layer, and the thus-produced precipitate was collected by filtration and dried under reduced pressure to obtain 101 mg of N-[5-(4-cyclohexylpiperazin-1-yl)-4-(4-fluorophenyl)thiazol-2-yl]-4-(3,4-dioxo-2-hydroxycyclobut-1-ene-1-yl)amino]benzamide hydrochloride.

EXAMPLE 19

To 430 mg of the compound of Example 198, 15 ml of water, and 15 ml of conc. HCl were added, and the mixture was stirred at 80° C. for 3.6 hours. The reaction solution was cooled to 0° C., 50 ml of water was added thereto, and the thus-produced precipitated was collected by filtration and dried under reduced pressure to obtain 101 mg of N-[5-(4-cyclohexylpiperazin-1-yl)-4-(4-fluorophenyl)thiazol-2-yl]-2,3-dihydroxyquinoxaline-6-carboxamide hydrochloride.

EXAMPLE 20

To a solution of 100 mg of the compound of Reference Example 149 in 5 ml of MeOH, 24 mg of sodium borohydride was added at 0° C., and the mixture was stirred at room temperature for 1 hour. 2 ml of DMF was added thereto, and the mixture was stirred for 1 hour, and 36 mg of the sodium borohydride was added and the mixture was stirred for 1 hour again. The reaction solution was poured into 1M aqueous HCl, alkalinized with saturated aqueous NaHCO$_3$, and extracted with chloroform, and the organic layer was dried over MgSO$_4$. The solvent was evaporated under reduced pressure, and the obtained residue was purified by silica gel column chromatography (chloroform-MeOH=100:1~20:1) and the obtained compound was dissolved in EtOAc, and then 0.5M HCl-EtOAc solution was added thereto and the thus-produced precipitate was collected by filtration to obtain 73 mg of N-[5-(4-cyclohexylpiperazin-1-yl)-4-(4-fluorophenyl) thiazol-2-yl]-4-hydroxymethylbenzamide hydrochloride.

EXAMPLE 21

To a suspension of 279 mg of the compound of Example 141 in 10 ml of toluene, 1.81 g of tributyltin azide was added, and the mixture was heated under reflux for 14 hours. And, diethylether, 1M aqueous NaOH, EtOAc, and conc. HCl were added thereto. The thus-produced precipitate was collected by filtration and dried under reduced pressure, and then dissolved in 1M aqueous NaOH and MeOH, and washed with diethylether. To the aqueous layer, conc. HCl was added at 0° C., and the thus-produced precipitate was collected by filtration to obtain 138 mg of N-[5-(4-cyclohexylpiperazin-1-yl)-4-(4-fluorophenyl)thiazol-2-yl]-4-(1H-tetrazol-5-ylmethyl) benzamide.

EXAMPLE 22

0.15 g of the compound of Example 149 was dissolved in 10 ml of THF, 0.1 ml of triethylamine and a solution of 40 mg of methyl chloroformate in 2 ml of THF were sequentially added thereto under ice cooling, and the mixture was stirred at room temperature overnight. The reaction solution was concentrated, mixed with water, and extracted with EtOAc. The obtained organic layer was washed with brine, and dried over anhydrous sodium sulfate. The solvent was concentrated under reduced pressure, and the thus-obtained residue was recrystallized from EtOAc to obtain 0.12 g of N-[5-(4-cyclohexylpiperazin-1-yl)-4-(4-fluorophenyl)thiazol-2-yl]-4-(methoxycarbonylaminomethyl)benzamide. The obtained compound was suspended in 5 ml of EtOAc, 0.6 ml of 0.4M HCl-EtOAc solution was added thereto under ice cooling, and the mixture was stirred overnight. The thus-precipitated solid was filtered and dried to obtain 115 mg of N-[5-(4-cylcohexylpiperazin-1-yl)-4-(4-fluorophenyl)thiazol-2-yl]-4-(methoxycarbonylaminomethyl)benzamide hydrochloride.

EXAMPLE 23

0.15 g of the compound of Example 149 was suspended in 5 ml of THF, 0.2 ml of triethylamine and a solution of 35 mg of methanesulfonyl chloride in 2 ml of THF were sequentially added thereto under ice cooling, and the mixture was stirred at room temperature for 3 hours. The reaction solution was concentrated, mixed with water, and extracted with EtOAc. The obtained organic layer was washed with brine, and dried over anhydrous sodium sulfate. The solvent was concentrated under reduced pressure, and the thus-obtained residue was recrystallized from EtOAc-hexane mixed solvent to obtain 0.12 g of N-[5-(4-cyclohexylpiperazin-1-yl)-4-(4-fluorophenyl)thiazol-2-yl]-4-(methanesulfonylaminomethyl)benzamide. The obtained compound was suspended in 5 ml of EtOAc, 0.2 ml of 1M HCl-EtOAc solution was added under ice cooling, and the mixture was stirred overnight. The thus-precipitated solid was filtered and dried to obtain 111 mg of N-[5-(4-cyclohexylpiperazin-1-yl)-4-(4-fluorophenyl)thiazol-2-yl]-4-(methanesulfonylaminomethyl)benzamide hydrochloride.

EXAMPLE 24

To a solution of 57 mg of the compound of Example 168 in 2 ml of pyridine, 18 μl of methyl chlorooxoacetate were added, and the mixture was stirred from 0° C. to room temperature for 2 hours. After the solvent was evaporated under reduced pressure, the residue was mixed with saturated aqueous $NaHCO_3$ and extracted with chloroform, and the organic layer was dried over $MgSO_4$. Then, the solvent was evaporated under reduced pressure, and the obtained residue was purified by silica gel column chromatography (eluent: chloroform-MeOH=100:1). And, diisopropyl ether was added thereto, and the thus-produced precipitate was collected by filtration to obtain 19 mg of methyl N-(4-{[5-(4-cyclohexylpiperazin-1-yl)-4-(4-fluorophenyl)thiazol-2-yl] carbamoyl}phenyl)oxamate.

EXAMPLE 25

To a suspension of 71 mg of the compound of Example 168 in 5 ml of DMF, 71 mg of 3-methoxypropionic acid, 120 mg of HOBt, and 180 mg of WSC.HCl were added, and the mixture was stirred from room temperature to 50° C. for 29 consecutive days. After the solvent was evaporated under reduced pressure, the residue was mixed with saturated aqueous $NaHCO_3$ and extracted with chloroform, and the organic layer was dried over $MgSO_4$. Then, the residue obtained by the evaporation of the solvent was purified by silica gel column chromatography (chloroform-MeOH=100:1~50:1). And, the obtained compound was dissolved in MeOH and 1M aqueous HCl, and purified by ODS column chromatography (0.001M HCl aq-MeOH=2:1~1:1), and then mixed with saturated aqueous $NaHCO_3$ and extracted with chloroform. After the organic layer was dried over $MgSO_4$, the solvent was evaporated, diisopropyl ether was added thereto, and the thus-produced precipitate was collected by filtration to obtain 20 mg of N-[5-(4-cyclohexypiperazin-1-yl)-4-(4-fluorophenyl)thiazol-2-yl]-4-[(3-methoxypropanoyl)amino]benzamide.

EXAMPLE 26

To a solution of 1.00 g of the compound of Example 83 in 15 ml of acetic acid, a total of 886 mg of palladium hydroxide-carbon (20 wt %) was added, and the mixture was stirred under a hydrogen atmosphere for 2 consecutive days. After celite filtration of the reaction solution, acetic acid was evaporated and saturated aqueous $NaHCO_3$ was added to the obtained residue. The thus-produced precipitate was collected by filtration, and dried under reduced pressure to obtain 505 mg of N-[4-(4-fluorophenyl)-5-(piperazin-1-yl)thiazol-2-yl]-2-methoxyisonicotinamide.

EXAMPLE 27

To a suspension of 202 mg of the compound of Example 26 and 207 mg of potassium carbonate in 15 ml of DMF, 46 μl of allyl bromide was added at 0° C., the temperature was slowly elevated, and the mixture was stirred at room temperature overnight. After the evaporation of the solvent under reduced pressure, the reaction solution was mixed with water, extracted with chloroform, and the organic layer was dried over $MgSO_4$. Then, the residue obtained by the evaporation of the solvent under reduced pressure was purified by silica gel column chromatography (chloroform-MeOH=300:0~100:1) and the obtained compound was dissolved in EtOAc, a 0.5 M HCl-EtOAc solution was added thereto, and the thus-produced precipitate was collected by filtration to obtain 165 mg of N-[5-(4-allylpiperazin-1-yl)-4-(4-fluorophenyl)thiazol-2-yl]-2-methoxyisonicotinamide hydrochloride.

EXAMPLE 28

To a solution of 178 mg of the compound of Example 56 in 4 ml of chloroform, 90 mg of m-chloroperbenzoic acid (mCPBA) was added under ice cooling, and the mixture was stirred at room temperature overnight. And, MeOH, saturated aqueous NaHCO$_3$, and chloroform were added thereto, and insoluble matter was removed by filtration, and then the reaction solution was extracted with chloroform. After drying over MgSO$_4$, the solvent was evaporated under reduced pressure. The thus-obtained residue was purified by silica gel column chromatography (chloroform-MeOH=300:1~400:1) and the obtained compound was suspended in EtOAc, and 0.5M HCl-EtOAc solution was added thereto, and the thus-produced precipitate was collected by filtration to obtain 39 mg of N-[4-(4-chloro-2-thienyl)-5-(1-oxidothiomorpholino)thiazol-2-yl]-2-methoxyisonicotinamide hydrochloride.

EXAMPLE 29

To a solution of 185 mg of the compound of Example 75 in 4 ml of acetic acid, 100 µl of hydrogen peroxide (30%) was added, and the mixture was stirred at room temperature overnight. And, saturated aqueous NaHCO$_3$, 1M aqueous NaOH, and 1M aqueous HCl were added thereto, and the thus-produced precipitate was collected by filtration. Chloroform and MeOH were added thereto to dissolve it, and the solution was mixed with saturated aqueous NaHCO$_3$ and extracted with chloroform. After drying over MgSO$_4$, the solvent was evaporated under reduced pressure. The thus-obtained residue was purified by silica gel column chromatography (chloroform-MeOH=300:1~100:1) and the obtained compound was suspended in EtOAc, a 0.5M HCl-EtOAc solution was added thereto, and the thus-produced precipitate was collected by filtration to obtain 47 mg of N-{4-(4-chlorothiophen-2-yl)-5-[4-(1-oxidothiomorpholino)piperidino]thiazol-2-yl}-2-methoxyisonicotinamide hydrochloride.

EXAMPLE 30

To a solution of 268 mg of the compound of Reference Example 41 in 8 ml of pyridine, 241 mg of the compound of Reference Example 127 were added, 72 µl of phosphorous oxychloride chloride were added at −25° C., the temperature was elevated to room temperature, and the mixture was stirred for 1.5 hours. After evaporation of the solvent under reduced pressure, the residue was mixed with water and potassium carbonate and extracted with chloroform. The organic layer was washed with brine and dried over sodium sulfate. The residue obtained by the evaporation of the solvent under reduced pressure was purified by silica gel column chromatography (chloroform-MeOH=200:1~100:1) and the obtained compound was dissolved in EtOAc, a 0.1M HCl-EtOAc solution was added thereto, and the thus-produced precipitate was collected by filtration to obtain 137 mg of 3-chloro-N-[4-(4-chlorothiophen-2-yl)-5-(4-cycohexylpiperazin-1-yl)thiazol-2-yl]-4-(2,3-dihydroxypropoxy)benzamide hydrochidride.

EXAMPLE 31

To a solution of 132 mg of the compound of Example 244 in 5 ml of MeOH, 61 mg of potassium carbonate were added, and the mixture was stirred at room temperature for 1.5 hours. The solvent was evaporated under reduced pressure, and the residue was mixed with water and extracted with chloroform. The organic layer was washed with brine and dried over sodium sulfate. The residue obtained by the evaporation of the solvent under reduced pressure was purified by silica gel column chromatography (chloroform-MeOH=200:1~50:1) and the obtained compound was dissolved in EtOAc, a 0.1 M HCl-EtOAc solution was added thereto, and the thus-produced precipitate was collected by filtration to obtain 77 mg of N-[4-(4-chlorothiophen-2-yl)-5-(4-cyclohexylpiperazin-1-yl)thiazol-2-yl]-4-(2-hydroxyethoxy)-3-methylbenzamide hydrochloride.

EXAMPLE 32

To a solution of 255 mg of the compound of Example 56 in 10 ml of chloroform, 303 mg of mCPBA were added, and the mixture was stirred at room temperature for 3 days. And, MeOH, saturated aqueous NaHCO$_3$, and chloroform were added thereto, insoluble matter was removed by filtration, and then the reaction solution was extracted with chloroform. The organic layer was dried over MgSO$_4$, and the solvent was evaporated under reduced pressure. The obtained residue was purified by silica gel column chromatography (chloroform-MeOH=300:1) and the obtained compound was suspended in EtOAc, a 0.5M HCl-EtOAc solution was added thereto, and the thus-produced precipitate was collected by filtration to obtain 130 mg of N-[4-(4-chloro-2-thienyl)-5-(1,1-dioxidothiomorpholino)thiazol-2-yl]-2-methoxyisonicotinamide hydrochloride.

EXAMPLE 33

To a solution of 0.35 g of the compound of Example 210 in 15 ml of DMF, 0.2 ml of triethylamine, 32 mg of diphenylphosphinoferrocene, and 13 mg of palladium acetate were added at room temperature, and the mixture was stirred under a carbon monoxide atmosphere at 70° C. for 1 day. After the solvent was evaporated under reduced pressure, the residue was mixed with water and extracted with chloroform, and the organic layer was dried over MgSO$_4$. The residue obtained by the evaporation of the solvent under reduced pressure was purified by silica gel column chromatography (chloroform-MeOH=100:0~98:2) and the obtained compound was dissolved in 5 ml of MeOH, 0.1 ml of 4M HCl-EtOAc solution was added thereto, and the thus-produced precipitate was collected by filtration to obtain 102 mg of N-[4-(4-chloro-2-thienyl)-5-(4-cyclohexylpiperazin-1-yl)thiazol-2-yl]-2-methoxycarbonylquinoline-6-carboxamide hydrochloride.

EXAMPLE 34

To a solution of 0.27 g of the compound of Example 213 in 10 ml of trifluoroacetic acid, 0.36 g of pentamethylbenzene was added at room temperature, and the mixture was stirred at room temperature for 6 days. After the solvent was evaporated under reduced pressure, the residue was mixed with water, neutralized with potassium carbonate, and extracted with chloroform, and the organic layer was dried over MgSO$_4$. The residue obtained by the evaporation of the solvent under reduced pressure was purified by silica gel column chromatography (chloroform-MeOH=100:0~97:3) and the obtained compound was dissolved in 5 ml of EtOAc, 0.47 ml of a 1M HCl-EtOAc solution was added thereto, and the thus-produced precipitate was collected by filtration to obtain 148 mg of N-[4-(4-chloro-2-thienyl)-5-(4-cycohexylpiperazin-1-yl)thiazol-2-yl]-7-hydroxyquinoline-3-carboxamide hydrochloride.

EXAMPLE 35

To a solution of 0.30 g of the compound of Example 217 in 5 ml of
MeOH, 2.0 ml of conc. HCl were added at room temperature, and the mixture was stirred at 70° C. for 3 days. The reaction solution was cooled to room temperature, and the thus-produced precipitated was collected by filtration to obtain 122 mg of 4-amino-3-chloro-N-[4-(4-chloro-2-thienyl)-5-(4-cyclohexylpiperazin-1-yl)thiazol-2-yl]benzamide hydrochloride.

EXAMPLE 36

To 350 mg of the compound of Example 5, 5 ml of DMF, 0.5 ml of piperidin-4-ylacetic acid ethyl ester, and 1.0 ml of triethylamine were added, and the mixture was stirred at 80 t for 8.5 hours. The solvent was evaporated, and the residue was mixed with 40 ml of water and extracted with chloroform. The organic layer was washed with brine and dried over sodium sulfate to evaporate the solvent. 10 ml of EtOH was added thereto to dissolve it, 0.5 ml of a 1M aqueous NaOH was added at room temperature, and the mixture was stirred at room temperature for 2 days, and then 0.5 ml of 1M aqueous NaOH was added thereto and the mixture was stirred at room temperature for 5 hours. To the reaction solution, 3 ml of 1M aqueous HCl were added at room temperature, the mixture was stirred for a while, and the thus-precipitated solid was filtered and dried to obtain 58 mg of [1-(3-chloro-5-{[4-(4-chloro-2-thienyl)-5-(4-cyclohexylpiperidin-1-yl)thiazol-2-yl]carbamoyl}-2-pyridyn-4-piperidyl]acetic acid hydrochloride.

EXAMPLE 37

To 272 mg of the compound of Example 366, 10 ml of THF, 10 ml of 1,4-dioxane, 50.5 mg of potassium cyanate, and 0.5 ml of 1M HCl were added, and the mixture was stirred at 40° C. for 5 hours and at 80° C. for 13 hours. Then, 2 ml of 1M HCl were added thereto at room temperature, and the mixture was stirred at 80° C. for 10 minutes. The solvent was evaporated under reduced pressure. The obtained residue was mixed with 40 ml of saturated aqueous NaHCO$_3$, and extracted with chloroform. The organic layer was washed with brine and dried over sodium sulfate to evaporate the solvent. The obtained residue was purified by silica gel column chromatography (chloroform-MeOH=5:1~1:1) and the obtained compound was dissolved in 60 ml of MeOH, 80 ml of chloroform, and 10 ml of 1,4-dioxane. And, 4 ml of 4M HCl was added thereto, and the mixture was stirred for a while, and then the solvent was evaporated under reduced pressure, and the residue was washed with diethylether to obtain 102 mg of 4-(3-chloro-5-{[4-(4-chloro-2-thienyl)-5-(4-cyclohexylpiperazin-1-yl)thiazol-2-yl]carbamoyl}-2-pyridyl)piperazin-1-carboxamide hydrochloride.

EXAMPLE 38

To a solution of 1.20 g of the compound of Example 331 in 40 ml of THF, 1.29 ml of triethylamine were added, 0.57 ml of trifluoroacetic acid anhydride was added under ice cooling, the temperature was elevated to room temperature, and the mixture was stirred for 3 days. The solvent was evaporated under reduced pressure, the residue was mixed with saturated aqueous NaHCO$_3$, and extracted with chloroform-MeOH (7:3). The organic layer was washed with brine and dried Over sodium sulfate. The residue obtained by the evaporation of the solvent under reduced pressure was purified by silica gel column chromatography (hexane-EtOAc=6:1~1:1, hexane-THF=1:1~0:1) and the obtained compound was washed with chloroform to obtain 882 mg of 5-choro-N-[4-(4-chlorothiophen-2-yl)-5-(4-cyclohexylpiperazin-1-yl)thiazol-2-yl]-6-(4-cyanopiperidin-1-yl)nicotinamide.

120 mg of the obtained compound were suspended in THF-MeOH, 0.1M HCl-EtOAc solution was added thereto, and the solvent was evaporated under reduced pressure. Then, EtOH-diethylether was added to the residue, and the thus-produced precipitate was collected by filtration to obtain 106 mg of 5-chloro-N-[4-(4-chlorothiophen-2-yl)-5-(4-cyclohexylpiperazin-1-yl)thiazol-2-yl]-6-(4-cyanopiperidin-1-yl)nicotinamide hydrochloride.

EXAMPLE 39

To a solution of 300 mg of the compound of Example 16 in 6 ml of THF, 56 μl of N-methylmorpholine was added, 60 μl of isobutyl chloroformate was added at −15° C., and the mixture was stirred for 2 hours. To a solution of 219 mg of methanesulfonamide in 4 ml of THF, 74 mg of sodium hydride was added, and the mixture was stirred at room temperature for 2 hours to prepare a suspension. The prepared suspension was added to the reaction solution, and the mixture was stirred at room temperature for 2 hours and at 50° C. for 20 hours. The reaction solution was cooled to room temperature, and the thus-precipitated solid was collected by filtration, washed with THF, purified by silica gel column chromatography (chloroform-MeOH=100:0~5:1) and the obtained compound was suspended in EtOH. Then, a 0.4 M HCl-EtOAc solution was added thereto, and the thus-produced precipitate was collected by filtration to obtain 119 mg of 5-chloro-N-[4-(4-chlorothiophen-2-yl)-5-(4-cyclohexypiperazin-1-yl)thiazol-2-yl]-6-[4-(N-methanesulfonylcarbamoyl)piperidin-1-yl]nicotinamide hydrochloride.

EXAMPLE 40

To a solution of 300 mg of the compound of Example 16 in 6 ml of THF, 56 μl of N-methylmorpholine were added, 60 μl of isobutyl chloroformate was added at −15° C., and the mixture was stirred for 1.5 hours. And, to a solution of 96 mg of methanesulfonamide in 4 ml of THF, 348 μl of 1,8-diazabicyclo[5,4,0]-7-undecene was added, and the mixture was stirred at room temperature for 19 hours and at 50° C. for 2 days. The reaction solution was mixed with saturated aqueous NaHCO$_3$ and extracted with EtOAc. The organic layer was washed with brine and dried over sodium sulfate. The residue obtained by the evaporation of the solvent under reduced pressure was purified by silica gel column chromatography (hexane-THF=2:1~0:1) and then by silica gel column chromatography (chloroform-MeOH=100:0~100:3), and the obtained compound was dissolved in chloroform-EtOH. A 0.1M HCl-EtOAc solution was added thereto, the solvent was evaporated under reduced pressure, EtOH-diethylether was added thereto, and the thus-produced precipitate was collected by filtration to obtain 30 mg of 5-chloro-N-[4-(4-chlorothiophen-2-yl)-5-(4-cyclohexylpiperazin-1-yl_thiazol-2-yl]-6-(4-(3-[2-(methanesulfonylimino)azepin-1-yl]propylaminocarbonyl)piperidin-1-yl)nicotinamide hydrochloride.

EXAMPLE 41

To 1.8 ml of a solution of the compound of Example 16 in THF (0.0856 mM), 70 mg of sarcosine ethyl ester hydrochloride, 342 mg of PS-DCC (1.35 mmol/g), 0.2 ml of a solution of HOBt in THF (0.77 mM), and 60 µl of triethylamine were added, and the mixture was stirred at room temperature overnight. To the reaction solution, 2 ml of THF, 370 mg of PS-isocyanate (1.25 mmol/g), and 205 mg of PS-trisamine (3.75 mmol/g) were added, and the mixture was stirred at room temperature for 1 hour. The reaction solution was filtered, and the obtained residue was purified by silica gel column chromatography (chloroform-MeOH=99:1-97:3) and the obtained compound was dissolved in 2 ml of EtOAc. And, 1 ml of 4M HCl-AcOEt was added thereto at room temperature, and the mixture was stirred for 15 minutes. The thus-precipitated solid was collected by filtration and dissolved in 2 ml of EtOH, 0.2 ml of 1M aqueous NaOH was added thereto, and the mixture was stirred at 50° C. for 160 minutes, and then 0.6 ml of 1M aqueous HCl was added thereto at room temperature, and the mixture was stirred overnight. The thus-precipitated solid was collected by filtration to obtain 49 mg of [{[1-(3-chloro-5-{[4-(4-chloro-2-thienyl)-5-(4-cyclohexylpiperazin-1-yl)thiazol-2-yl]carbamoyl}-2-pyridyl)-4-piperazyl]carbonyl}(methyl)amino]acetic acid hydrochloride.

EXAMPLE 42

To a solution of the compound of Example 16 in 1.8 ml of THF (0.0856 mM), 39 mg of morpholine, 342 mg of PS-DCC (1.35 mmol/g), and 0.2 ml of a solution of HOBt in THF (0.77 mM) were added, and the mixture was stirred at room temperature overnight. To the reaction solution, 2 ml of THF, 370 mg of PS-isocyanate (1.25 mmol/g), and 205 mg of PS-trisamine (3.75 mmollg) were added, and the mixture was stirred at room temperature for 1 hour. The reaction solution was filtered, and the obtained residue was purified by silica gel column chromatography (chloroform-MeOH=99:1~97:3) and the obtained compound was dissolved in 2 ml of EtOAc. And, 1 ml of 4M HCl-EtOAc was added thereto at room temperature, and the mixture was stirred for 15 minutes. The thus-precipitated solid was collected by filtration to obtain 84 mg of 5-chloro-N-[4-(4-chlorothiophen-2-yl)-5-(4-cyclohexylpiperazin-1-yl)thiazol-2-yl]-6-[4-(morpholinocarbonyl)piperidino]nicotinamide hydrochloride.

The structures and physical properties of the compounds of Examples are shown in Tables 11-21. Symbols in the Tables have the following meaning.
Ex: Example number (In case only Example number is described in Ex. column, the compound is hydrochloride, and in case a slant line (/) and symbol are described after Example number, /AcOH: indicates acetate; /TFA indicates trifluoroacetate; and /free indicates a free body.)
Syn: Synthesis method (The number indicates the Example number used for synthesis)
$R^A$, $R^B$, $R^C$, $R^D$, $R^E$, $R^F$, $R^G$, $R^H$, $R^I$: substituent groups in the general Formula (nPen: normal pentyl, cPen: cyclopentyl, vinyl: vinyl, naph: naphthyl, Ms: methanesulfonyl, oxo: oxo, Py: pyridyl, pra: pyrazol-3-yl, ttrz: tetrazol-5-yl, bimid: benzoimidazol-1-yl, oxido: oxido, di and tri: respectively di and tri (indicating that 2 or 3 substituent groups substitute)

TABLE 11

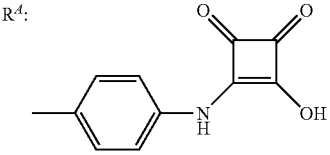

| Ex | $R^A$; $R^B$; $R^C$ | Data |
|---|---|---|
| 1 | $R^A$: 4-cyano-Ph; $R^B$: 4-F-Ph; $R^C$: 4-cHex-pipa | 490. |
| 2 | $R^A$: 2-MeO-4-py; $R^B$: 5-Cl-2-The; $R^C$: 4-cHex-pipa | 518. |
| 3 | $R^A$: 2-MeO-4-py; $R^B$: 5-Cl-2-The; $R^C$: 4-nPr-pipe | 477. |
| 4 | $R^A$: 3-Cl-4-HO (CH$_2$)$_2$O-Ph; $R^B$: 4-F-Ph; $R^C$: 4-cHex-pipa | 559. |
| 5/free | $R^A$: 5,6-diCl-3-py; $R^B$: 4-Cl-2-The; $R^C$: 4-cHex-pipa | 556. |
| 6 | $R^A$: 5-Cl-6-HO-3-py; $R^B$: 4-Cl-2-The; $R^C$: 4-cHex-pipa | 538. |
| 7/TFA | $R^A$: 3-Cl-4-HOCH$_2$CH(Me)O-Ph; $R^B$: 4-Cl-2-The; $R^C$: 4-cHex-pipa | 595. |
| 8 | $R^A$: 3-F-4-HO-Ph; $R^B$: 4-Cl-2-The; $R^C$: 4-cHex-pipa | 521. |
| 9 | $R^A$: 3-Cl-4-HO(CH$_2$)$_2$O-Ph; $R^B$: 4-Cl-2-The; $R^C$: 4-cHex-pipa | 581. |
| 10/AcOH | $R^A$: 2-MeO-4-py; $R^B$: 4-Cl-2-The; $R^C$: pipa | 436. |
| 11 | $R^A$: 2-MeO-4-py; $R^B$: 2-The; $R^C$: 4-cHex-pipa | 484. |
| 12 | $R^A$: 5-Cl-6-HO(CH$_2$)$_2$O-3-py; $R^B$: 4-Cl-2-The; $R^C$: 4-cHex-pipa | 582. |
| 13/free | $R^A$: 5-Cl-6-(4-(EtO$_2$C)-pipe)-3-py; $R^B$: 4-Cl-2-The; $R^C$: 4-cHex-pipa | 677. |
| 14 | $R^A$: 2-MeO-4-py; $R^B$: 4-Cl-2-The; $R^C$: 4-Bn-pipa | 526. |
| 15 | $R^A$: 4-H$_2$NCH$_2$-Ph; $R^B$: 4-Cl-2-The; $R^C$: 4-cHex-pipa | 516. |
| 16 | $R^A$: 5-Cl-6-(4-(HO$_2$C)-pipe)-3-py; $R^B$: 4-Cl-2-The; $R^C$: 4-cHex-pipa | 649. |
| 17 | $R^A$: 4-((H$_2$NOC)-CH$_2$)-Ph; $R^B$: 4-F-Ph; $R^C$: 4-cHex-pipa | 522. |
| 18 | $R^A$: (squaric acid-4-anilino structure) ; $R^B$: 4-F-Ph; $R^C$: 4-cHex-pipa | 576. |
| 19 | $R^A$: 2,3-diHO-quinoxalin-6-yl; $R^B$: 4-F-Ph; $R^C$: 4-cHex-pipa | 549. |
| 20 | $R^A$: 4-HOCH$_2$-Ph; $R^B$: 4-F-Ph; $R^C$: 4-cHex-pipa | 495. |
| 21/free | $R^A$: 4-(ttrz-CH$_2$)-Ph; $R^B$: 4-F-Ph; $R^C$: 4-cHex-pipa | 547. |
| 22 | $R^A$: 4-((MeO$_2$C)—HNCH$_2$)-Ph; $R^B$: 4-F-Ph; $R^C$: 4-cHex-pipa | 552. |
| 23 | $R^A$: 4-MsHNCH$_2$-Ph; $R^B$: 4-F-Ph; $R^C$: 4-cHex-pipa | 572. |

TABLE 11-continued

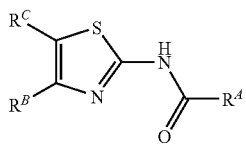

| Ex | $R^A$; $R^B$; $R^C$ | Data |
|---|---|---|
| 24/free | $R^A$: 4-((MeO$_2$C)—OCHN)-Ph; $R^B$: 4-F-Ph; $R^C$: 4-cHex-pipa | 566. |
| 25/free | $R^A$: 4-(MeO(CH$_2$)$_2$—(OCHN))-Ph; $R^B$: 4-F-Ph; $R^C$: 4-cHex-pipa | 566. |
| 26 | $R^A$: 2-MeO-4-py; $R^B$: 4-F-Ph; $R^C$: pipa | 414. |
| 27 | $R^A$: 2-MeO-4-py; $R^B$: 4-F-Ph; $R^C$: 4-allyl-pipa | 454. |
| 28 | $R^A$: 2-MeO-4-py; $R^B$: 4-Cl-2-The; $R^C$: 1-oxido-tmor | 469. |
| 29 | $R^A$: 2-MeO-4-py; $R^B$: 4-Cl-2-The; $R^C$: 4-(1-oxido-tmor)-pipe | 552. |
| 30 | $R^A$: 3-Cl-4-(HOCH$_2$CH(OH)CH$_2$O)-Ph; $R^B$: 4-Cl-2-The; $R^C$: 4-cHex-pipa | |
| 31 | $R^A$: 3-Me-4-HO(CH$_2$)$_2$O)-Ph; $R^B$: 4-Cl-2-The; $R^C$: 4-cHex-pipa | 561. |
| 32 | $R^A$: 2-MeO-4-py; $R^B$: 4-Cl-2-The; $R^C$: 1,1-dioxido-tmor | 485. |
| 33 | $R^A$: 3-MeO$_2$C-quinolin-6-yl; $R^B$: 4-Cl-2-The; $R^C$: 4-cHex-pipa | 595. |
| 34 | $R^A$: 7-HO-quinolin-3-yl; $R^B$: 4-Cl-2-The; $R^C$: 4-cHex-pipa | 554. |
| 35 | $R^A$: 3-Cl-4-H$_2$N-Ph; $R^B$: 4-Cl-2-The; $R^C$: 4-cHex-pipa | 536. |
| 36 | $R^A$: 5-Cl-6-(4-((HO$_2$C)—CH$_2$)-pipe)-3-py; $R^B$: 4-Cl-2-The; $R^C$: 4-cHex-pipa | 663. |
| 37 | $R^A$: 5-Cl-6-(4-(H$_2$NOC)-pipe)-3-py; $R^B$: 4-Cl-2-The; $R^C$: 4-cHex-pipa | 649. |
| 38 | $R^A$: 5-Cl-6-(4-cyano-pipe)-3-py; $R^B$: 4-Cl-2-The; $R^C$: 4-cHex-pipa | 630. |
| 39 | $R^A$: 5-Cl-6-(4-(MsHN—OC)-pipe)-3-py; $R^B$: 4-Cl-2-The; $R^C$: 4-cHex-pipa | 726. |
| 40 | $R^A$: 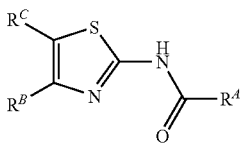 ; $R^B$: 4-Cl-2-The; $R^C$: 4-cHex-pipa | 878. |
| 41 | $R^A$ 5-Cl-6-(4-((HO$_2$C)—CH$_2$—(Me)NOC)-pipe)-3-py; $R^B$: 4-Cl-2-The; $R^C$: 4-cHex-pipa | 720. |
| 42 | $R^A$: 5-Cl-6-(4-(mor-OC)-pipe)-3-py; $R^B$: 4-Cl-2-The; $R^C$: 4-cHex-pipa | 718. |

TABLE 12

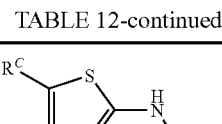

| Ex | $R^A$ | $R^B$ | $R^C$ | MS | Syn |
|---|---|---|---|---|---|
| 43 | 3,5-diMeO-Ph | 4-F-Ph | —N(Me)((CH$_2$)$_2$OMe) | 446. | 2 |
| 44 | 3,5-diMeO-Ph | 4-F-Ph | —N(Me)((CH$_2$)$_2$NMe$_2$) | 459. | 2 |
| 45 | 3,5-diMeO-Ph | 4-F-Ph | —N(Me)((CH$_2$)$_3$NMe$_2$) | 473. | 2 |
| 46 | 3,5-diMeO-Ph | 4-F-Ph | —N(Me)((CH$_2$)$_2$N(Me)(cHex)) | 527. | 2 |
| 47 | 3,5-diMeO-Ph | 4-F-Ph | —N(Me)((CH$_2$)$_2$-pipe) | 499. | 2 |
| 48 | 2-MeO-4-py | 4-Cl-2-The | —N(Me)((CH$_2$)$_3$-mor) | 508. | 5 |
| 49 | 2-MeO-4-py | 4-Cl-2-The | —N(Me)(1-nBu-pyrrolidin-3-yl) | 506. | 5 |
| 50 | 2-MeO-4-py | 4-Cl-2-The | —N(Me)(1-nBu-piperidin-4-yl) | 520. | 5 |

TABLE 12-continued

| Ex | $R^A$ | $R^B$ | $R^C$ | MS | Syn |
|---|---|---|---|---|---|
| 51 | 2-MeO-4-py | 4-Cl-2-The | —N(Me)(quinuclidin-3-yl) | 490. | 5 |
| 52 | 2-MeO-4-py | 4-Cl-2-The | —N(cHex)((CH$_2$)$_2$-mor) | 562. | 5 |

TABLE 13

| Ex | $R^A$ | $R^B$ | $R^C$ | MS | Syn |
|---|---|---|---|---|---|
| 53 | 2-MeO-4-py | 4-F-Ph | imid | 396. | 2 |
| 54 | 2-MeO-4-py | 4-F-Ph | 4-Ph-imid | 472. | 2 |
| 55 | 2-MeO-4-py | 4-F-Ph | 3-pipe-azet | 468. | 2 |
| 56 | 2-MeO-4-py | 4-Cl-2-The | tmor | 453. | 5 |
| 57 | 2-MeO-4-py | 4-Cl-2-The | 3-(4-nPr-pipe)-azet | 532. | 5 |
| 58 | quinolin-6-yl | 4-Cl-2-The | mor | 457. | 5 |

TABLE 14

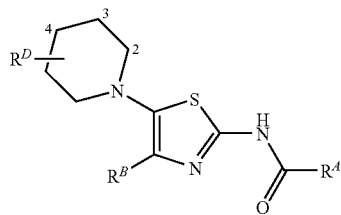

| Ex | R$^A$ | R$^B$ | R$^D$ | MS | Syn |
|---|---|---|---|---|---|
| 59 | 2-MeO-4-py | 4-F-Ph | 4-nPr | 455. | 3 |
| 60 | 2-MeO-4-py | 4-F-Ph | 4-nPrO | 471. | 3 |
| 61 | 2-MeO-4-py | 4-F-Ph | 4-mor | 498. | 2 |
| 62 | 2-MeO-4-py | 4-F-Ph | 4-Ph-4-AcHN | MM; 545. | 3 |
| 63 | quinolin-6-yl | 4-F-Ph | 4-nPr | 475. | 2 |
| 64 | 3-F-4-HO-Ph | 4-Cl-2-The | 4-nPr | 480. | 8 |
| 65/free | 3-F-4-MeOCH$_2$O-Ph | 4-Cl-2-The | 4-nPr | 524. | 5 |
| 66 | 2-MeO-4-py | 4-Cl-2-The | 4-nPr | 477. | 5 |
| 67 | quinolin-6-yl | 4-Cl-2-The | 4-nPr | 497. | 5 |
| 68 | 2-MeO-4-py | 4-Cl-2-The | 2-((Me$_2$N)—CH$_2$) | 492. | 5 |
| 69 | 2-MeO-4-py | 4-Cl-2-The | 3-((Me$_2$N)—CH$_2$) | 492. | 5 |
| 70 | 2-MeO-4-py | 4-Cl-2-The | 4-(Me)(nPr)N | 506. | 5 |
| 71 | 2-MeO-4-py | 4-Cl-2-The | 4-(Me)(cHex)N | 546. | 5 |
| 72 | 2-MeO-4-py | 4-Cl-2-The | 4-(Me)((F$_3$C)—CH2)N | 546. | 5 |
| 73 | 2-MeO-4-py | 4-Cl-2-The | 4-(Me)((F$_3$C)—(CH$_2$)$_2$)N | 560. | 5 |
| 74 | 2-MeO-4-py | 4-Cl-2-The | 4-mor | 520. | 5 |
| 75 | 2-MeO-4-py | 4-Cl-2-The | 4-tmor | 536. | 5 |
| 76 | 2-MeO-4-py | 4-Cl-2-The | 4-pipe | 518. | 5 |
| 77/free | 5,6-diCl-3-py | 4-Cl-2-The | 4-pipe | 556, 558. | 5 |
| 78/free | 5,6-diCl-3-py | 4-Cl-2-The | 4-(3-F-pyrr) | 560. | 5 |
| 79 | quinolin-6-yl | 5-Cl-2-The | 4-nPr | 497. | 3 |
| 80 | quinolin-6-yl | 5-Cl-2-The | Me-CH=C(1-methylpiperidin-4-ylidene) | 495. | 3 |

TABLE 15

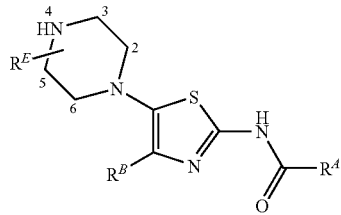

| Ex | R$^A$ | R$^B$ | R$^E$ | MS | Syn |
|---|---|---|---|---|---|
| 81/free | 2-MeO-4-py | 4-F-Ph | 4-((HO$_2$C)—CH$_2$) | 472. | 16 |
| 82/free | 2-MeO-4-py | 4-F-Ph | 4-((EtO$_2$C)—CH$_2$) | 500. | 27 |
| 83 | 2-MeO-4-py | 4-F-Ph | 4-BnO$_2$C | 547. | 2 |
| 84 | 2-MeO-4-py | 4-F-Ph | 4-(cyano-CH$_2$) | MM; 452. | 27 |
| 85 | 2-MeO-4-py | 4-F-Ph | 4-((Me$_2$N)—(CH$_2$)$_2$) | 485. | 27 |
| 86 | 2-MeO-4-py | 4-F-Ph | (trans)-2,5-diMe-4-nBu | 498. | 3 |
| 87 | 2-MeO-4-py | 4-Cl-2-The | 3-oxo. | 450. | 5 |
| 88 | 2-MeO-4-py | 4-Cl-2-The | 4-nPr | 478. | 5 |
| 89 | 2-MeO-4-py | 4-Cl-2-The | 4-nBu | 492. | 14 |
| 90 | 2-MeO-4-py | 4-Cl-2-The | (3R*,5S*)-3,5-diMe-4-nPr | 506. | 5 |
| 91/free | 2-MeO-4-py | 4-Cl-2-The | 4-((HO$_2$C)—CH$_2$) | 494. | 16 |
| 92 | 2-MeO-4-py | 4-Cl-2-The | 4-((EtO$_2$C)—CH$_2$) | 522. | 14 |
| 93 | 2-MeO-4-py | 4-Cl-2-The | 4-((Me$_2$NOC)—CH$_2$) | 521. | 25 |
| 94 | 2-MeO-4-py | 4-Cl-2-The | 4-((pipe-OC)—CH$_2$) | 561. | 25 |
| 95 | 2-MeO-4-py | 4-Cl-2-The | 4-((2-py)-CH$_2$) | 527. | 14 |
| 96 | 2-MeO-4-py | 4-Cl-2-The | 4-((2-The)-CH$_2$) | 532. | 14 |
| 97 | 2-MeO-4-py | 4-Cl-2-The | 4-((2-oxo-pyrr)-(CH$_2$)$_2$) | 547. | 27 |
| 98 | 2-MeO-4-py | 4-Cl-2-The | 4-cPen | 504. | 14 |
| 99 | 2-MeO-4-py | 4-Cl-2-The | 4-(4-Et-cHex) | 546. | 14 |
| 100 | 2-MeO-4-py | 4-Cl-2-The | 4-cHept | 532. | 5 |
| 101 | 2-MeO-4-py | 4-Cl-2-The | 4-(allyl-O$_2$C) | 519. | 5 |
| 102 | 2-MeO-4-py | 4-Cl-2-The | 4-(tetrahydro-2H-pyran-4-yl) | 520. | 14 |

TABLE 15-continued

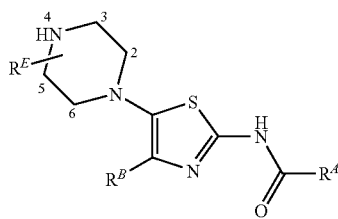

| Ex | $R^A$ | $R^B$ | $R^E$ | MS | Syn |
|---|---|---|---|---|---|
| 103 | 3-Cl-4-HO(CH$_2$)$_2$O-Ph | 4-Cl-2-The | 4-nPr | 541. | 9 |
| 104/free | 5,6-diCl-3-py | 4-Cl-2-The | 4-nPr | 516. | 5 |
| 105 | 5-Cl-6-HO(CH$_2$)$_2$HN-3-py | 4-Cl-2-The | 4-nPr | 541. | 13 |

TABLE 16

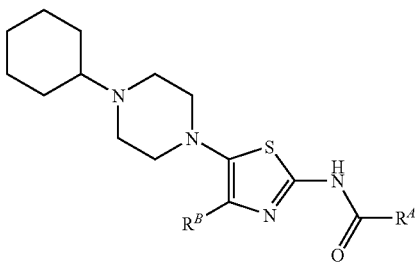

| Ex | $R^A$ | $R^B$ | MS | Syn |
|---|---|---|---|---|
| 106 | 2-MeO-4-py | 3-F$_3$C-Ph | 546. | 5 |
| 107 | 2-MeO-4-py | 4-F$_3$C-Ph | 546. | 2 |
| 108 | 2-MeO-4-py | 4-HO$_2$C-Ph | 522. | 16 |
| 109 | 2-MeO-4-py | 4-H$_2$NOC-Ph | 521. | 17 |
| 110 | 2-MeO-4-py | 3-cyano-Ph | 503. | 5 |
| 111 | 2-MeO-4-py | 4-cyano-Ph | 503. | 2 |
| 112 | 2-MeO-4-py | 4-Me$_2$N-Ph | 521. | 2 |
| 113 | 2-MeO-4-py | 4-O$_2$N-Ph | 523. | 2 |
| 114/free | 5,6-diCl-3-py | 3-Cl-Ph | 550. | 5 |
| 115/free | 5,6-diCl-3-py | 3-F$_3$C-Ph | 584. | 5 |
| 116 | 2-MeO-4-py | 5-Me-2-Fur | 482. | 2 |
| 117 | 2-MeO-4-py | 3-F-2-The | 502. | 5 |
| 118 | 2-MeO-4-py | 4-F-2-The | 502. | 5 |
| 119 | 2-MeO-4-py | 5-F-2-The | 502. | 5 |
| 120 | 2-MeO-4-py | 3-Cl-2-The | 518. | 5 |
| 121 | 3-F-4-HO-Ph | 5-Cl-2-The | 521. | 8 |
| 122/free | 3-F-4-MeOCH$_2$O-Ph | 5-Cl-2-The | | 5 |
| 123 | 3-F-4-MeO(CH$_2$)$_2$O-Ph | 5-Cl-2-The | 579. | 3 |
| 124 | 3,5-diF-4-MeO(CH$_2$)$_2$O-Ph | 5-Cl-2-The | 597. | 3 |
| 125 | 3-Cl-4-HO(CH$_2$)$_2$O-Ph | 5-Cl-2-The | 581. | 9 |
| 126 | 3-Cl-4-MeO(CH$_2$)$_2$O-Ph | 5-Cl-2-The | 595. | 3 |
| 127/free | 3-Cl-4-TBSO(CH$_2$)$_2$O-Ph | 5-Cl-2-The | 695. | 5 |
| 128 | 2-Cl-6-Me-4-py | 5-Cl-2-The | 536. | 3 |
| 129 | 2-Cl-6-MeO-4-py | 5-Cl-2-The | 552. | 3 |
| 130 | 5-MeO-3-py | 5-Cl-2-The | 518. | 3 |
| 131 | 2-MeO-6-Me-4-py | 5-Cl-2-The | 532. | 3 |
| 132/free | 2,6-diMeO-pyrimidin-4-yl | 5-Cl-2-The | 549. | 3 |
| 133 | quinolin-6-yl | 5-Cl-2-The | 538. | 3 |
| 134 | 2-MeO-4-py | 5-Cl-3-The | 518. | 5 |
| 135 | 2-MeO-4-py | 4-Br-2-The | 562, 564. | 5 |
| 136 | 2-MeO-4-py | 5-Br-2-The | 562, 564. | 2 |
| 137 | 2-MeO-4-py | 4-F-5-Cl-2-The | 536. | 5 |
| 138 | 2-MeO-4-py | 4,5-diCl-2-The | 552. | 5 |
| 139 | 2-MeO-4-py | 4-Me-2-The | 498. | 5 |
| 140 | 2-MeO-4-py | 5-Me-2-The | 498. | 2 |

TABLE 17

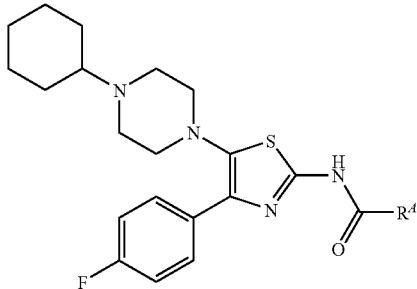

| Ex | $R^A$ | MS | Syn |
|---|---|---|---|
| 141 | 4-(cyano-CH$_2$)-Ph | 504. | 2 |
| 142 | 3-((HO$_2$C)—CH$_2$)-Ph | 523. | 16 |
| 143 | 4-((HO$_2$C)—CH$_2$)-Ph | 523. | 16 |
| 144 | 3-((MeO$_2$C)—CH$_2$)-Ph | 537. | 5 |
| 145 | 4-((MeO$_2$C)—CH$_2$)-Ph | 537. | 5 |
| 146 | 3-((H$_2$NOC)—CH$_2$)-Ph | 522. | 17 |
| 147 | | 604. | 2 |
| 148/free | 4-AcOCH$_2$-Ph | 537. | 2 |
| 149 | 4-H2NCH$_2$-Ph | 494. | 15 |
| 150 | 4-AcHNCH$_2$-Ph | 536. | 2 |
| 151/free | 4-BocHNCH$_2$-Ph | 594. | 2 |
| 152 | 4-((H$_2$NOC)—HNCH$_2$)-Ph | 537. | 2 |
| 153 | 4-((H$_2$NO$_2$S)—HNCH$_2$)-Ph | 573. | 2 |
| 154 | 4-HO-3-(mor-CH$_2$)-Ph | 580. | 2 |
| 155 | 4-((2-oxo-pyrr)-CH$_2$)-Ph | 562. | 2 |
| 156 | 4-(cyano-(CH$_2$)$_2$)-Ph | 518. | 5 |
| 157 | 4-((E)-2-cyanovinyl)-Ph | 516. | 5 |
| 158 | 3-F-4-F$_3$C-Ph | 551. | 1 |
| 159 | 3-F-4-((Me$_2$N)—CH$_2$)-Ph | 540. | 2 |
| 160 | 3-cyano-Ph | 490. | 1 |
| 161 | 3-Cl-4-((HO$_2$C)—CH$_2$O)-Ph | 573. | 16 |
| 162 | 3-Cl-4-((MeO$_2$C)—CH$_2$O)-Ph | 587. | 2 |
| 163 | 3-Cl-4-MeO(CH$_2$)$_2$O-Ph | 573. | 2 |
| 164 | 3-F-4-((Me$_2$N)—(CH$_2$)$_2$O)-Ph | 540. | 2 |
| 165 | 4-PhO-Ph | 557. | 2 |
| 166 | 4-(4-HO-PhO)-Ph | 573. | 8 |
| 167/free | 4-(4-MeOCH$_2$O-PhO)-Ph | 617. | 5 |
| 168/free | 4-H$_2$N-Ph | 480. | 9 |
| 169/free | 4-BocHN-Ph | 580. | 2 |
| 170 | 4-MsHN-Ph | 558. | 2 |
| 171 | 4-((HO$_2$C)—CH$_2$HN)-Ph | 538. | 16 |
| 172/free | 4-((EtO$_2$C)—CH$_2$HN)-Ph | 566. | 14 |
| 173/free | 4-(MeOCH$_2$—(OCHN))-Ph | 552. | 24 |

TABLE 17-continued

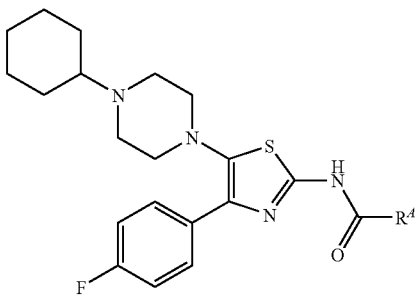

| Ex | R$^A$ | MS | Syn |
|---|---|---|---|
| 174 | 4-((HO$_2$C)—(OCHN))-Ph | 552. | 16 |
| 175 | 4-mor-Ph | 550. | 5 |
| 176 | 4-pipa-Ph | 549. | 15 |
| 177 | 4-(4-Me-pipa)-Ph | 563. | 14 |
| 178 | 4-(4-Ac-pipa)-Ph | 591. | 5 |
| 179/free | 4-(4-Boc-pipa)-Ph | 649. | 5 |
| 180/free | 4-HO$_3$S-Ph | 545. | 2 |
| 181 | 2-naph | 515. | 1 |
| 182 | 6-HO-2-naph | 531. | 2 |
| 183/free | 5,6-diCl-3-py | 534. | 5 |
| 184 | 1,3-benzodioxolan-5-yl | 509. | 1 |
| 185 | 3-oxo-3,4-dihydro-2H-1,4-benzoxazin-7-yl | 536. | 5 |
| 186/free | 1H-indol-5-yl | MM; 503. | 2 |
| 187 | 2-Me-isoindolin-5-yl | 520. | 2 |
| 188 | 5-bimid | 505. | 2 |
| 189 | quinolin-2-yl | 516. | 2 |
| 190 | quinolin-3-yl | 516. | 2 |
| 191 | quinolin-4-yl | 516. | 5 |
| 192 | quinolin-6-yl | 516. | 2 |
| 193 | quinolin-7-yl | 516. | 5 |
| 194 | 2-HO-quinolin-6-yl | 532. | 2 |
| 195 | 2-MeO-quinolin-6-yl | 546. | 5 |
| 196 | isoquinolin-3-yl | 516. | 2 |
| 197 | isoquinolin-7-yl | 516. | 5 |
| 198/free | 2,3-diBnO-quinoxalin-6-yl | 729. | 5 |
| 199 | imidazol[1,2-a]pyridin-6-yl | 505. | 2 |

TABLE 18

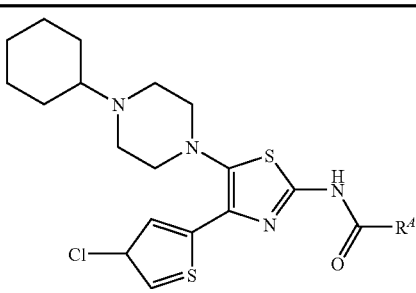

| Ex | R$^A$ | MS | Syn |
|---|---|---|---|
| 200 | 5-Me-1-HO(CH$_2$)$_3$-pra | 549. | 9 |
| 201/free | 5-Me-1-TBSO(CH$_2$)$_3$-pra | 663. | 5 |
| 202 | 3-oxo-3,4-dihydro-2H-1,4-benzoxazin-7-yl | 558. | 5 |
| 203 | 2-oxo-2,3-dihydrobenzoxazol-5-yl | 544. | 5 |
| 204 | 2-oxo-2,3-dihydrobenzoxazol-6-yl | 544. | 5 |
| 205 | 2-oxo-3-HO(CH$_2$)$_2$-2,3-dihydrobenzoxazol-6-yl | 588. | 9 |
| 206/free | 2-oxo-3-TBSO(CH$_2$)$_2$-2,3-dihydrobenzoxazol-6-yl | 702. | 5 |
| 207 | quinolin-3-yl | 538. | 5 |
| 208 | quinolin-6-yl | 538. | 5 |
| 209 | quinolin-7-yl | 538. | 5 |
| 210/free | 2-Br-quinolin-6-yl | 615, 617. | 5 |
| 211 | 2-HO$_2$C-quinolin-6-yl | MN; 580. | 16 |

TABLE 18-continued

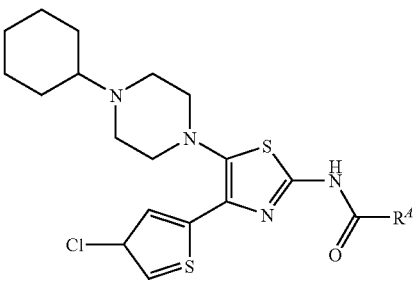

| Ex | R$^A$ | MS | Syn |
|---|---|---|---|
| 212 | 2-H$_2$NOC-quinolin-6-yl | 581. | 5 |
| 213/free | 7-BnO-quinolin-3-yl | 644. | 5 |
| 214 | isoquinolin-6-yl | 538. | 5 |
| 215 | isoquinolin-7-yl | 538. | 5 |
| 216 | imidazo[1,2-a]pyridin-7-yl | 527. | 5 |
| 217 | 3-Cl-4-((1,4-dioxa-8-azaspiro[4.5]dec-8-yl)-Ph) | 662. | 5 |
| 218/free | 3-F-4-MeOCH$_2$O-Ph | 565. | 5 |
| 219 | 3,5-diF-4-HO(CH$_2$)$_2$O-Ph | 583. | 7 |
| 220 | 3,5-diF-4-tBuO(CH$_2$)$_2$O-Ph | 639. | 5 |
| 221 | 3,4,5-triF-Ph | 541. | 5 |
| 222 | 3-Cl-5-F-4-HO(CH$_2$)$_2$O-Ph | 599. | 9 |
| 223/free | 3-Cl-5-F-4-TBSO(CH$_2$)$_2$-Ph | 713. | 5 |
| 224 | 3-Cl-4-MeO(CH$_2$)$_2$HNCH$_2$-Ph | 608. | 15 |
| 225/free | 3-Cl-4-MeO(CH$_2$)$_2$N(Boc)CH$_2$-Ph | 708. | 5 |
| 226 | 3-Cl-4-HO-Ph | 537. | 8 |
| 227/free | 3-Cl-4-MeOCH$_2$O-Ph | 581. | 5 |
| 228 | 3-Cl-4-((tetrahydro-2-fur)-CH$_2$O)-Ph | 621. | 5 |
| 229 | 3-Cl-4-MeO(CH$_2$)$_2$O-Ph | 595. | 5 |
| 230/free | 3-Cl-4-TBSO(CH$_2$)$_2$O-Ph | 695. | 5 |
| 231 | 3-Cl-4-H$_2$N(CH$_2$)$_2$-Ph | 580. | 15 |
| 232/free | 3-Cl-4-BocHN(CH$_2$)$_2$O-Ph | 680. | 5 |
| 233 | 3-Cl-4-tBuOCH$_2$CH(Me)O-Ph | 651. | 5 |
| 234 | 3-Cl-4-HO(CH$_2$)$_3$O-Ph | 595. | 9 |
| 235/free | 3-Cl-4-TBSO(CH$_2$)$_3$O-Ph | 709. | 5 |
| 236 | 3-Cl-4-(tetrahydro-3-fur-O)-Ph | 607. | 5 |
| 237 | 3,5-diCl-4-HO-Ph | 571 | 5 |
| 238 | 3,5-diCl-4-HO(CH$_2$)$_2$O-Ph | 615. | 9 |
| 239/free | 3,5-diCl-4-TBSO(CH$_2$)$_2$O-Ph | 729. | 5 |
| 240 | 3-Br-4-HO(CH$_2$)$_2$O-Ph | 625, 627. | 9 |
| 241/free | 3-Br-4-TBSO(CH$_2$)$_2$O-Ph | 739, 741. | 5 |
| 242 | 4-((Me$_2$N)-CH$_2$)-Ph | 544. | 14 |
| 243/free | 4-BocHNCH$_2$-Ph | 616. | 5 |
| 244 | 3-Me-4-AcO(CH$_2$)$_2$O-Ph | 603. | 5 |
| 245 | 2-MeO-4-py | 518. | 5 |
| 246 | 5-Cl-6-MeO-3-py | 552. | 5 |
| 247 | 2-EtO-4-py | 532. | 5 |
| 248 | 5-Cl-6-(HO(CH$_2$)$_2$)(Me)N-3-py | 595. | 13 |
| 249 | 5-Cl-6-HO(CH$_2$)$_2$HN-3-py | 581. | 13 |
| 250 | 5-Cl-6-HO(CH$_2$)$_2$O-3-py | 596. | 12 |
| 251 | 2-AcO(CH$_2$)$_2$O-4-py | 590. | 5 |
| 252 | 2-HO(CH$_2$)$_2$O-4-py | 548. | 31 |
| 253 | 5-Cl-6-HO(CH$_2$)$_3$HN-3-py | 595. | 13 |
| 254 | 5-Cl-6-MeO(CH$_2$)$_3$HN-3-py | 609. | 13 |
| 255 | 5-Cl-6-(1-Me-pyrrolidin-2-yl-(CH$_2$)$_2$O)-3-py | 649. | 12 |
| 256 | 5-Cl-6-(HO(CH$_2$)$_2$)$_2$N-3-py | 625. | 13 |
| 257 | 5-Cl-6-HOCH(Me)CH$_2$HN-3-py | 595. | 13 |
| 258 | 5-Cl-6-((4-(4-F-Bn)-morpholin-2-yl)CH$_2$HN)-3-py | 744. | 13 |
| 259 | 5-Cl-6-((MeO$_2$C)-CH$_2$HN)-3-py | 609. | 13 |
| 260 | 5-Cl-6-H$_2$N(CH$_2$)$_3$HN-3-py | 594. | 13 |
| 261 | 5-Cl-6-(4-HO-cHex)HN-3-py | 635. | 13 |
| 262 | 5-Cl-6-H$_2$NCH$_2$CH(OH)CH$_2$HN-3-py | 610. | 13 |
| 263 | 5-Cl-6-(2-HO-cHex)HN-3-py | 635. | 13 |

TABLE 18-continued

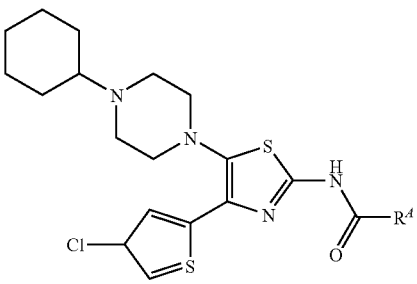

| Ex | $R^A$ | MS | Syn |
|---|---|---|---|
| 264 | 5-Cl-6-HOCH$_2$CH(OH)CH$_2$HN-3-py | 611. | 13 |
| 265 | 5-Cl-6-((HO$_2$C)-CH$_2$HN)-3-py | 595. | 16 |
| 266 | 5-Cl-6-(3-Me-oxetan-3-yl-CH$_2$O)-3-py | 622. | 12 |
| 267 | 5-Cl-6-(tetrahydro-3-Fur-CH$_2$O)-3-py | 622. | 12 |
| 268 | 5-Cl-6-MeO(CH$_2$)$_2$HN-3-py | 595. | 13 |

TABLE 19

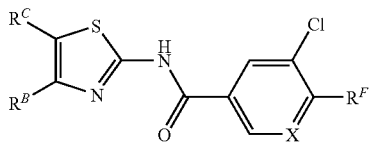

| Ex | X | $R^F$ | $R^B$ | $R^C$ | MS | Syn |
|---|---|---|---|---|---|---|
| 269 | CH | 4-cyano-pipe | 4-Cl-2-The | 4-nPr-pipa | 589. | 5 |
| 270 | CH | 4-HO$_2$C-pipe | 4-Cl-2-The | 4-nPr-pipa | 608. | 16 |
| 271 | CH | 4-EtO$_2$C-pipe | 4-Cl-2-The | 4-nPr-pipa | 636. | 5 |
| 272 | CH | 4-H$_2$NOC-pipe | 4-Cl-2-The | 4-nPr-pipa | 607. | 7 |
| 273/free | CH | 4-(PhC(Me)$_2$—(HNOC))-pipe | 4-Cl-2-The | 4-nPr-pipa | 725. | 25 |
| 274 | CH | 4-HO-pipe | 4-Cl-2-The | 4-nPr-pipa | 580. | 9 |
| 275/free | CH | 4-TBSO-pipe | 4-Cl-2-The | 4-nPr-pipa | 694. | 5 |
| 276 | N | 4-HO$_2$C-pipe | 4-F-Ph | 4-cHex-pipa | 627. | 16 |
| 277/free | N | 4-EtO$_2$C-pipe | 4-F-Ph | 4-cHex-pipa | 655. | 13 |
| 278 | N | 4-HO$_2$C-pipe | 3-Cl-Ph | 4-cHex-pipa | 643. | 16 |
| 279 | N | 4-EtO$_2$C-pipe | 3-Cl-Ph | 4-cHex-pipa | 671. | 13 |
| 280 | N | 4-HO$_2$C-pipe | 3-F$_3$C-Ph | 4-cHex-pipa | 677. | 16 |
| 281 | N | 4-EtO$_2$C-pipe | 3-F$_3$C-Ph | 4-cHex-pipa | 705. | 13 |
| 282 | N | 4-HO$_2$C-pipe | 4-Cl-2-The | 4-nPr-pipa | 609. | 16 |
| 283/free | N | 4-EtO$_2$C-pipe | 4-Cl-2-The | 4-nPr-pipa | 637. | 13 |
| 284 | N | 4-H$_2$NOC-pipe | 4-Cl-2-The | 4-nPr-pipa | 608. | 13 |
| 285 | N | 4-HO-pipe | 4-Cl-2-The | 4-nPr-pipa | 581. | 13 |
| 286 | N | 4-HO$_2$C-pipe | 4-Cl-2-The | 4-(3-F-pyrr)-pipe | 653. | 16 |
| 287/free | N | 4-EtO$_2$C-pipe | 4-Cl-2-The | 4-(3-F-pyrr)-pipe | 681. | 13 |
| 288 | N | 4-H$_2$NOC-pipe | 4-Cl-2-The | 4-pipe-pipe | 648. | 13 |

TABLE 20

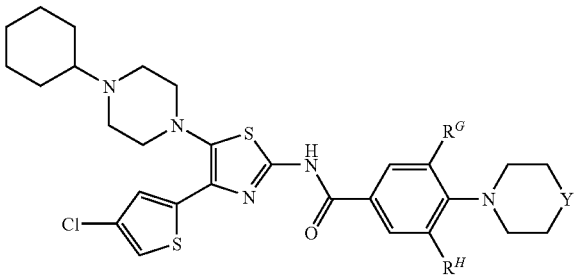

| Ex | $R^G$ | $R^H$ | Y | MS | Syn |
|---|---|---|---|---|---|
| 289 | Cl | H | CH-cyano | 629. | 5 |
| 290 | Cl | H | CH—CO$_2$H | 648. | 16 |
| 291 | Cl | H | CH—CO$_2$Et | 676. | 5 |

TABLE 20-continued

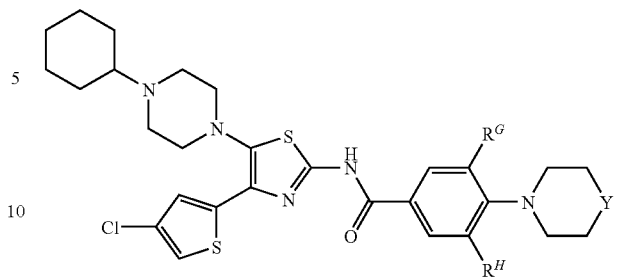

| Ex | $R^G$ | $R^H$ | Y | MS | Syn |
|---|---|---|---|---|---|
| 292 | Cl | H | CH—CONH$_2$ | 647. | 17 |
| 293 | Cl | H | CH—OH | 620. | 9 |
| 294/free | Cl | H | CH—OTBS | 734. | 5 |
| 295 | Br | H | CH—CO$_2$H | 694. | 16 |
| 296/free | Br | H | CH—CO$_2$Et | 722. | 5 |
| 297 | Br | H | CH—CONH$_2$ | 693. | 25 |

TABLE 20-continued

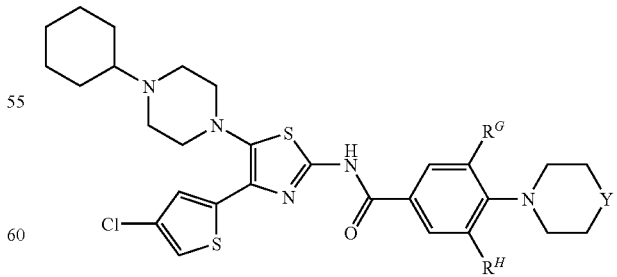

| Ex | $R^G$ | $R^H$ | Y | MS | Syn |
|---|---|---|---|---|---|
| 298 | F | F | CH-cyano | 631. | 5 |
| 299 | F | F | CH—CO$_2$H | 650. | 16 |
| 300/free | F | F | CH—CO$_2$Et | 678. | 5 |

TABLE 20-continued

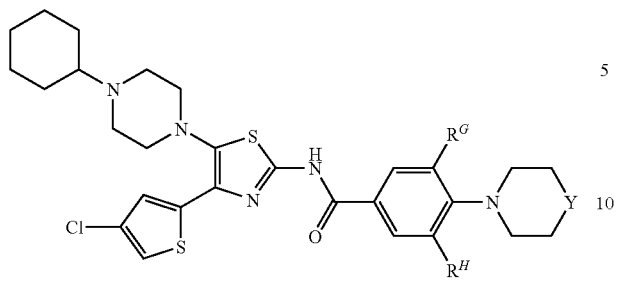

| Ex | R$^G$ | R$^H$ | Y | MS | Syn |
|---|---|---|---|---|---|
| 301 | F | F | CH—CONH$_2$ | 649. | 25 |
| 302 | F | Cl | CH-cyano | 647. | 5 |
| 303 | F | Cl | CH—CO$_2$H | 666. | 16 |
| 304 | F | Cl | CH—CO$_2$Et | 694. | 5 |
| 305 | F | Cl | CH—CONH$_2$ | 664. | 7 |
| 306/free | F | Cl | CH—CONH—C(Me)$_2$Ph | 783. | 25 |
| 307/free | F | Cl | NH | 623. | 15 |
| 308 | F | Cl | N-(2-HO-Bn) | 729. | 14 |
| 309 | F | Cl | N—CH$_2$—CO$_2$H | 681. | 16 |
| 310/free | F | Cl | N—CH$_2$—CO$_2$Et | 709. | 14 |
| 311 | F | Cl | N—CH$_2$—CONH$_2$ | 680. | 25 |
| 312/free | F | Cl | N-Boc | 723. | 5 |
| 313 | F | Cl | N—CO—CH$_2$OMe | 695. | 24 |
| 314 | F | Cl | N—CO—CO$_2$H | 695. | 16 |
| 315/free | F | Cl | N—CO—CO$_2$Et | 723. | 24 |
| 316 | F | Cl | N—SO$_2$NH$_2$ | 702. | 15 |
| 317/free | F | Cl | N—SO$_2$NHBoc | 802. | 23 |

TABLE 21

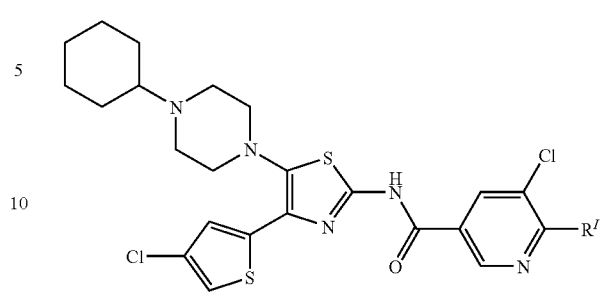

| Ex | R$^I$ | MS | Syn |
|---|---|---|---|
| 318 | 3-HO-azet | 593. | 13 |
| 319 | 3-F-pyrr | 609. | 13 |
| 320 | (S)-2-HOCH$_2$-pyrr | 621. | 13 |
| 321 | (R)-2-HOCH$_2$-pyrr | 621. | 13 |
| 322 | 3-HO-pyrr | 607. | 13 |
| 323 | (R)-3-HO-pyrr | 607. | 13 |
| 324 | 3-Me$_2$N-pyrr | 634. | 13 |
| 325 | 4-ttrz-pipe | 673. | 21 |
| 326 | 4-F-pipe | 623. | 13 |
| 327 | 3-HOCH$_2$-pipe | 635. | 13 |
| 328 | 4-HOCH$_2$-pipe | 635. | 13 |
| 329 | 2-HO(CH$_2$)$_2$-pipe | 649. | 13 |
| 330 | ![structure] | 689. | 13 |
| 331 | 4-H$_2$NOC-pipe | 648. | 13 |
| 332 | 4-(MeHNOC)-pipe | 662. | 25 |

TABLE 21-continued

| Ex | R$^I$ | MS | Syn |
|---|---|---|---|
| 333 | 4-(nPrHNOC)-pipe | 690. | 42 |
| 334 | 4-(nPenHNOC)-pipe | 718. | 42 |
| 335 | 4-(cHexHNOC)-pipe | 730. | 42 |
| 336 | 4-(BnHNOC)-pipe | 738. | 42 |
| 337 | 4-((cHex-CH$_2$)—(HNOC))-pipe | 744. | 42 |
| 338 | 4-(MeO(CH$_2$)$_2$—(HNOC))-pipe | 706. | 42 |
| 339 | 4-(EtO(CH$_2$)$_2$—(HNOC))-pipe | 720. | 42 |
| 340 | 4-(MeO(CH$_2$)$_3$—(HNOC))-pipe | 720. | 42 |
| 341 | 4-(Me$_2$N(CH$_2$)$_3$—(HNOC))-pipe | 733. | 42 |
| 342 | 4-(Me$_2$N(CH$_2$)$_4$—(HNOC))-pipe | 747. | 42 |
| 343 | 4-(Me$_2$N(CH$_2$)$_6$—(HNOC))-pipe | 775. | 42 |
| 344 | 4-Me$_2$NOC-pipe | 676. | 25 |
| 345 | 4-((Me)(nPr)N—OC)-pipe | 704. | 42 |
| 346 | 4-(MeO(CH$_2$)$_2$-((Me)NOC))-pipe | 720. | 42 |
| 347 | 4-(pipe-OC)-pipe | 716. | 42 |
| 348 | 4-(tmor-OC)-pipe | 734. | 42 |
| 349 | 3-HO-pipe | 621. | 13 |
| 350 | 4-HO-pipe | 621. | 13 |
| 351 | 4-H$_2$N-pipe | 620. | 15 |
| 352 | 4-BnHN-pipe | 710. | 13 |
| 353 | 4-AcHN-pipe | 662. | 24 |
| 354/free | 4-BocHN-pipe | 720. | 13 |
| 355 | 4-MsHN-pipe | 698. | 23 |
| 356 | pipa | 606. | 13 |
| 357 | 3-HOCH$_2$-4-Me-pipa | 650. | 13 |
| 358 | 4-((HO$_2$C)—CH$_2$)-pipa | 664. | 16 |
| 359/free | 4-((EtO$_2$C)—CH$_2$)-pipa | 692. | 13 |
| 360 | 4-HO(CH$_2$)$_2$-pipa | 650. | 13 |
| 361 | 4-MeO(CH$_2$)$_2$-pipa | 664. | 13 |
| 362 | 3-oxo-pipa | 620. | 13 |
| 363 | 3,5-dioxo-pipa | 634. | 13 |
| 364 | 4-Ac-pipa | 648. | 13 |
| 365/free | 4-EtO$_2$C-pipa | 678. | 13 |
| 366 | 4-((4-Me-pipa)-OC)-pipe | 731. | 25 |
| 367 | 4-Ms-pipa | 684. | 23 |
| 368 | mor | 607. | 13 |
| 369 | tmor | 623. | 13 |
| 370 | 1,4-diazepan-1-yl | 620. | 13 |
| 371 | 4-Ac-1,4-diazepan-1-yl | 662. | 13 |
| 372 | 5-oxo-1,4-diazepan-1-yl | 634. | 13 |
| 373 | 5-HO$_2$C-isoindolin-2-yl | 683. | 16 |
| 374 | 5-MeO$_2$C-isoindolin-2-yl | 697. | 13 |

NMR data of some of the compounds of Examples are shown in the following Table 22.

TABLE 22

| Ex | NMR |
|---|---|
| 8 | 1.05-1.20 (1H, m), 1.21-1.36 (2H, m), 1.38-1.55 (2H, m), 1.58-1.68 (1H, m), 1.82-1.91 (2H, m), 2.14-2.25 (2H, m), 3.20-3.40 (7H, m), 3.55-3.65 (2H, m), 7.11 (1H, dd, J = 8.3, 8.8 Hz), 7.49 (1H, s), 7.56 (1H, s), 7.83 (1H, dd, J = 1.4, 8.3 Hz), 8.21 (1H, dd, J = 1.4, 12.6 Hz), 10.95 (1H, brs), 12.50 (1H, brs). |
| 9 | 1.06-1.20 (1H, m), 1.22-1.36 (2H, m), 1.43-1.56 (2H, m), 1.59-1.68 (1H, m), 1.80-1.92 (2H, m), 2.17-2.27 (2H, m), 3.20-3.44 (7H, m), 3.54-3.63 (2H, m), 3.78 (2H, t, J = 4.9 Hz), 4.21 (2H, t, J = 4.9 Hz), 7.33 (1H, d, J = 8.8 Hz), 7.50 (1H, d, J = 1.5 Hz), 7.57 (1H, d, J = 1.5 Hz), 8.08 (1H, dd, J = 2.0, 8.8 Hz), 8.24 (1H, d, J = 2.0 Hz), 10.89 (1H, brs), 12.61 (1H, brs). |
| 16 | 1.06-1.20 (1H, m), 1.22-1.36 (2H, m), 1.40-1.55 (2H, m), 1.58-1.70 (3H, m), 1.78-2.00 (4H, m), 2.15-2.25 (2H, m), 2.50-2.58 (1H, m), 2.98-3.09 (2H, m), 3.23-3.40 (7H, m), 3.54-3.66 (2H, m), 3.93-4.02 (2H, m), 7.48 (1H, d, J = 1.5 Hz), 7.57 (1H, d, J = 1.5 Hz), 8.40 (1H, d, J = 1.9 Hz), 8.83 (1H, d, J = 1.9 Hz), 10.98 (1H, brs), 12.28 (1H, brs), 12.68 (1H, s). |
| 36 | 1.08-1.20 (1H, m), 1.21-1.38 (4H, m), 1.38-1.55 (2H, m), 1.60-1.68 (1H, m), 1.74-2.00 (4H, m), 2.16-2.22 (5H, m), 2.87 (2H, t, J = 12.2 Hz), 3.20-3.34 (9H, m), 4.04 (2H, d, J = 13.2 Hz), 7.50 (1H, s), 7.57 (1H, s), 8.39 (1H, d, J = 2.0 Hz), 8.83 (1H, d, J = 2.0 Hz), 10.34 (1H, brs), 12.09 (1H, brs), 12.66 (1H, brs). |
| 42 | 1.14-1.20 (1H, m), 1.21-1.32 (2H, m), 1.38-1.53 (2H, m), 1.60-1.77 (5H, m), 1.81-1.92 (2H, m), 2.14-2.25 (2H, m), 2.88-3.08 (3H, m), 3.30-3.37 (2H, m), 3.42-3.50 (2H, m), 3.52-3.64 (4H, m), 3.76-3.88 (9H, m), 4.05-4.12 (2H, m), 7.49 (1H, d, J = 1.5 Hz), 7.58 (1H, d, J = 1.5 Hz), 8.40 (1H, d, J = 1.9 Hz), 8.83 (1H, d, J = 1.9 Hz), 10.77 (1H, brs), 12.67 (1H, brs). |
| 66 | 0.90 (3H, t, J = 6.8 Hz), 1.22-1.49 (7H, m), 1.75-1.85 (2H, m), 2.63-2.71 (2H, m), 3.06-3.16 (2H, m), 3.92 (3H, s), 7.42 (1H, d, J = 2.0 Hz), 7.43 (1H, s), 7.51 (1H, d, J = 2.0 Hz), 7.54 (1H, d, J = 5.4 Hz), 8.36 (1H, d, J = 5.4 Hz), 12.80 (1H, brs). |
| 103 | 0.95 (3H, t, J = 7.3 Hz), 1.71-1.82 (2H, m), 3.11-3.36 (8H, m), 3.60 (2H, d, J = 10.3 Hz), 3.78 (2H, t, J = 5.2 Hz), 4.21 (2H, t, J = 4.9 Hz), 7.33 (1H, d, J = 8.8 Hz), 7.50 (1H, d, J = 1.9 Hz), 7.58 (1H, d, J = 2.0 Hz), 8.08 (1H, dd, J = 2.0 Hz, J = 8.8 Hz), 8.24 (1H, d, J = 2.0 Hz), 10.73 (1H, brs), 12.62 (1H, s). |
| 105 | 0.90 (3H, t, J = 7.3 Hz), 1.72-1.82 (2H, m), 3.11-3.33 (8H, m), 3.55-3.61 (6H, m), 7.22 (1H, brs), 7.49 (1H, d, J = 1.5 Hz), 7.57 (1H, d, J = 1.5 Hz), 8.28 (1H, d, J = 1.9 Hz), 8.74 (1H, d, J = 2.0 Hz), 10.88 (1H, brs), 12.48 (1H, s). |
| 125 | 1.07-1.20 (1H, m), 1.22-1.36 (2H, m), 1.42-1.55 (2H, m), 1.60-1.68 (1H, m), 1.81-1.91 (2H, m), 2.16-2.26 (2H, m), 3.20-3.29 (7H, m), 3.56-3.65 (2H.m), 3.78 (2H, t, J = 4.9 Hz), 4.21 (2H, t, J = 4.9 Hz), 7.12 (1H, d, J = 3.9 Hz), 7.33 (1H, d, J = 8.8 Hz), 7.47 (1H, d, J = 3.9 Hz), 8.08 (1H, dd, J = 8.8, 2.0 Hz), 8.23 (1H, d, J = 2.0 Hz), 10.93 (1H, brs), 12.63 (1H, brs). |
| 204 | 1.07-1.20 (1H, m), 1.22-1.36 (2H, m), 1.41-1.55 (2H, m), 1.59-1.68 (1H, m), 1.82-1.92 (2H, m), 2.14-2.24 (2H, m), 3.27-3.35 (7H, m), 3.55-3.65 (2H, m), 7.24 (1H, d, J = 8.3 Hz), 7.50 (1H, d, J = 1.5 Hz), 7.57 (1H, d, J = 1.5 Hz), 7.97 (1H, dd, J = 1.5, 8.3 Hz), 8.06 (1H, s), 10.74 (1H, brs), 12.13 (1H, s), 12.63 (1H, brs). |
| 208 | 1.03-1.20 (1H, m), 1.21-1.36 (2H, m), 1.38-1.55 (2H, m), 1.60-1.68 (1H, m), 1.82-1.91 (2H, m), 2.18-2.25 (2H, m), 3.22-3.40 (7H, m), 3.55-3.65 (2H, m), 7.52 (1H, s), 7.58 (1H, s), 7.76 (1H, dd, J = 4.2, 8.3 Hz), 8.21 (1H, d, J = 8.8 Hz), 8.40 (1H, dd, J = 1.5, 8.8 Hz), 8.67 (1H, d, J = 8.3 Hz), 8.89 (1H, d, J = 1.5 Hz), 9.11 (1H, d, J = 4.2 Hz), 11.05 (1H, brs), 12.96 (1H, brs). |
| 214 | 1.03-1.20 (1H, m), 1.21-1.36 (2H, m), 1.40-1.55 (2H, m), 1.60-1.68 (1H, m), 1.82-1.91 (2H, m), 2.18-2.28 (2H, m), 3.20-3.43 (7H, m), 3.52-3.65 (2H, m), 7.52 (1H, s), 7.59 (1H, s), 8.33-8.40 (2H, m), 8.50 (1H, d, J = 8.8 Hz), 8.73 (1H, d, J = 5.8 Hz), 8.90 (1H, s), 9.78 (1H, s), 11.20 (1H, brs), 13.12 (1H, brs). |
| 222 | 1.07-1.20 (1H, m), 1.21-1.36 (2H, m), 1.41-1.54 (2H, m), 1.58-1.68 (1H, m), 1.80-1.92 (2H, m), 2.14-2.25 (2H, m), 3.25-3.37 (7H, m), 3.56-3.64 (2H, m), 3.73 (2H, t, J = 4.9 Hz), 4.24 (2H, t, J = 4.9 Hz), 7.50 (1H, d, J = 1.0 Hz), 7.58 (1H, d, J = 1.0 Hz), 8.01 (1H, dd, J = 2.0, 11.7 Hz), 8.11 (1H, brs), 10.77 (1H, brs), 12.77 (1H, brs). |
| 226 | 1.06-1.20 (1H, m), 1.21-1.36 (2H, m), 1.42-1.56 (2H, m), 1.59-1.68 (1H, m), 1.81-1.91 (2H, m), 2.16-2.26 (2H, m), 3.20-3.45 (7H, m), 3.54-3.63 (2H, m), 7.17 (1H, d, J = 8.8 Hz), 7.49 (1H, d, J = 1.4 Hz), 7.56 (1H, d, J = 1.4 Hz), 7.94 (1H, dd, J = 2.4, 8.8 Hz), 8.19 (1H, d, J = 2.4 Hz), 11.26 (1H, brs), 12.51 (1H, brs). |
| 229 | 1.06-1.20 (1H, m), 1.22-1.36 (2H, m), 1.44-1.56 (2H, m), 1.58-1.68 (1H, m), 1.80-1.92 (2H, m), 2.15-2.26 (2H, m), 3.17-3.47 (7H, m), 3.35 (3H, s), 3.56-3.63 (2H, m), 3.73 (2H, t, J = 3.9 Hz), 4.31 (2H, t, J = 3.9 Hz), 7.33 (1H, d, J = 8.8 Hz), 7.49 (1H, d, J = 0.9 Hz), 7.56 (1H, d, J = 0.9 Hz), 8.08 (1H, dd, J = 1.9, 8.8 Hz), 8.24 (1H, d, J = 1.9 Hz), 11.31 (1H, brs), 12.61 (1H, brs). |
| 234 | 1.08-1.20 (1H, m), 1.22-1.36 (2H, m), 1.41-1.55 (2H, m), 1.58-1.68 (1H, m), 1.82-1.90 (2H, m), 1.92 (2H, t, J = 6.3 Hz), 2.19-2.22 (2H, m), 3.21-3.37 (7H, m), 3.55-3.63 (4H, m), 4.25 (2H, t, J = 6.3 Hz), 7.32 (1H, d, J = 8.8 Hz), 7.50 (1H, s), 7.57 (1H, s), 8.09 (1H, dd, J = 2.0, 8.8 Hz), 8.24 (1H, d, J = 2.0 Hz), 10.83 (1H, brs), 12.62 (1H, brs). |
| 238 | 1.07-1.20 (1H, m), 1.22-1.36 (2H, m), 1.44-1.56 (2H, m), 1.60-1.68 (1H, m), 1.83-1.91 (2H, m), 2.17-2.26 (2H, m), 3.20-3.42 (7H, m), 3.56-3.63 (2H, m), 3.78 (2H, t, J = 4.9 Hz), 4.13 (2H, t, J = 4.9 Hz), 7.49 (1H, s), 7.57 (1H, s), 8.21 (2H, s), 11.18 (1H, brs), 12.79 (1H, brs). |

TABLE 22-continued

| Ex | NMR |
|---|---|
| 240 | 1.07-1.20 (1H, m), 1.22-1.36 (2H, m), 1.42-1.56 (2H, m), 1.60-1.67 (1H, m), 1.81-1.90 (2H, m), 2.18-2.25 (2H, m), 3.17-3.43 (7H, m), 3.55-3.65 (2H, m), 3.78 (2H, t, J = 4.9 Hz), 4.20 (2H, t, J = 4.9 Hz), 7.29 (1H, d, J = 8.8 Hz), 7.49 (1H, d, J = 1.5 Hz), 7.56 (1H, d, J = 1.5 Hz), 8.12 (1H, dd, J = 2.4, 8.8 Hz), 8.39 (1H, d, J = 2.4 Hz), 11.19 (1H, brs), 12.61 (1H, brs). |
| 245 | 1.08-1.20 (1H, m), 1.21-1.34 (2H, m), 1.40-1.53 (2H, m), 1.60-1.68 (1H, m), 1.82-1.89 (2H, m), 2.14-2.24 (2H, m), 3.22-3.45 (7H, m), 3.55-3.65 (2H, m), 3.95 (3H, s), 7.44 (1H, s), 7.50 (1H, s), 7.54 (1H, d, J = 4.9 Hz), 7.56 (1H, s), 8.37 (1H, d, J = 4.9 Hz), 10.61 (1H, brs), 12.95 (1H, brs). |
| 250 | 1.06-1.20 (1H, m), 1.22-1.36 (2H, m), 1.41-1.54 (2H, m), 1.60-1.68 (1H, m), 1.82-1.95 (2H, m), 1.92 (2H, t, J = 6.4 Hz), 2.15-2.24 (2H, m), 3.22-3.36 (7H, m), 3.55-3.63 (2H, m), 3.58 (2H, t, J = 6.4 Hz), 4.51 (2H, t, J = 6.4 Hz), 7.49 (1H, d, J = 1.5 Hz), 7.57 (1H, d, J = 1.5 Hz), 8.53 (1H, d, J = 2.0 Hz), 8.82 (1H, d, J = 2.0 Hz), 10.83 (1H, brs), 12.78 (1H, s). |
| 253 | 1.05-1.20 (1H, m), 1.22-1.36 (2H, m), 1.42-1.54 (2H, m), 1.60-1.68 (1H, m), 1.70-1.77 (1H, m), 1.82-1.92 (2H, m), 2.15-2.25 (2H, m), 3.20-3.40 (7H, m), 3.45-3.65 (4H, m), 3.49 (2H, t, J = 6.3 Hz), 7.39 (1H, brs), 7.48 (1H, d, J = 1.5 Hz), 7.56 (1H, d, J = 1.5 Hz), 8.27 (1H, d, J = 2.0 Hz), 8.74 (1H, d, J = 2.0 Hz), 10.98 (1H, brs), 12.45 (1H, s). |
| 264 | 1.06-1.20 (1H, m), 1.22-1.36 (2H, m), 1.40-1.54 (2H, m), 1.59-1.68 (1H, m), 1.80-1.91 (2H, m), 2.13-2.24 (2H, m), 3.24-3.33 (9H, m), 3.55-3.45 (2H, m), 3.54-3.65 (2H, m), 3.68-3.75 (1H, m), 7.01-7.07 (1H, m), 7.49 (1H, d, J = 1.5 Hz), 7.56 (1H, d, J = 1.5 Hz), 8.29 (1H, d, J = 1.9 Hz), 8.74 (1H, d, J = 1.9 Hz), 10.68 (1H, brs), 12.48 (1H, s). |
| 267 | 1.07-1.20 (1H, m), 1.22-1.36 (2H, m), 1.39-1.54 (2H, m), 1.60-1.75 (2H, m), 1.82-1.92 (2H, m), 1.98-2.08 (1H, m), 2.13-2.24 (2H, m), 2.68-2.78 (1H, m), 3.22-3.37 (4H, m), 3.41-3.51 (4H, m), 3.54-3.71 (3H, m), 3.76-3.82 (2H, m), 4.32-4.45 (2H, m), 7.50 (1H, d, J = 1.5 Hz), 7.58 (1H, d, J = 1.5 Hz), 8.55 (1H, d, J = 2.0 Hz), 8.82 (1H, d, J = 2.0 Hz), 10.60 (1H, brs), 12.80 (1H, s). |
| 270 | 0.93 (3H, t, J = 7.3 Hz), 1.42-1.81 (4H, m), 1.90-2.00 (2H, m), 2.40-2.48 (1H, m), 2.72-2.86 (2H, m), 2.80-3.70 (12H, m), 7.24 (1H, d, J = 8.8 Hz), 7.48 (1H, brs), 7.55 (1H, brs), 8.03 (1H, dd, J = 1.9, 8.8 Hz), 8.18 (1H, d, J = 1.9 Hz), 10.68 (1H, brs), 12.25 (1H, brs), 12.58 (1H, s). |
| 272 | 0.95 (3H, t, J = 7.8 Hz), 1.68-1.88 (6H, m), 2.23-2.34 (1H, m), 2.70-2.79 (1H, m), 3.10-3.19 (2H, m), 3.20-3.35 (5H, m), 3.40-3.53 (3H, m), 3.56-3.64 (2H, m), 6.80 (1H, brs), 7.24 (1H, d, J = 8.3 Hz), 7.33 (1H, brs)7.50 (1H, d, J = 1.5 Hz), 7.58 (1H, d, J = 1.5 Hz), 8.03 (1H, dd, J = 2.0, 8.3 Hz), 8.18 (1H, d, J = 2.0 Hz), 10.86 (1H, brs), 12.61 (1H, s). |
| 274 | 0.94 (3H, t, J = 7.3 Hz), 1.51-1.63 (2H, m), 1.71-1.82 (2H, m), 1.83-1.92 (2H, m), 2.81-2.90 (2H, m), 3.10-3.17 (2H, m), 3.17-3.37 (8H, m), 3.55-3.63 (2H, m), 3.63-3.72 (1H, m), 7.24 (1H, d, J = 8.3 Hz), 7.50 (1H, d, J = 1.5 Hz), 7.58 (1H, d, J = 1.5 Hz), 8.03 (1H, dd, J = 1.9, 8.3 Hz), 8.18 (1H, d, J = 1.9 Hz), 10.92 (1H, brs), 12.61 (1H, s). |
| 276 | 1.05-1.20 (1H, m), 1.22-1.37 (2H, m), 1.40-1.52 (2H, m), 1.60-1.75 (3H, m), 1.80-1.97 (4H, m), 2.15-2.24 (2H, m), 2.50-2.52 (1H, m), 3.04 (2H, t, J = 10.8 Hz), 3.17-3.38 (7H, m), 3.47-3.60 (2H, m), 3.98 (2H, d, J = 13.2 Hz), 7.27 (2H, t, J = 8.8 Hz), 8.15 (2H, dd, J = 5.8, 8.8 Hz), 8.40 (1H, d, J = 2.0 Hz), 8.84 (1H, d, J = 2.0 Hz), 10.85 (1H, brs), 12.28 (1H, brs), 12.59 (1H, brs). |
| 278 | 1.08-1.20 (1H, m), 1.22-1.36 (2H,m), 1.38-1.52 (2H, m), 1.58-1.75 (3H, m), 1.81-1.99 (4H, m), 2.11-2.22 (2H, m), 2.50-2.52 (1H, m), 2.98-3.08 (2H, m), 3.19-3.35 (7H, m), 3.48-3.64 (2H, m), 3.92-4.22 (2H, m), 7.34-7.41 (1H, m), 7.49 (1H, d, J = 7.8 Hz), 8.09-8.11 (1H, m), 8.12-8.17 (1H, m), 8.41 (1H, d, J = 2.0 Hz), 8.84 (1H, d, J = 2.0 Hz), 10.55 (1H, brs), 12.28 (1H, brs), 12.59 (1H, brs). |
| 280 | 1.08-1.20 (1H, m), 1.21-1.38 (2H, m), 1.39-1.51 (2H, m), 1.60-1.73 (3H, m), 1.80-2.00 (4H, m), 2.10-2.22 (2H, m), 2.50-2.52 (1H, m), 2.99-3.10 (2H, m), 3.22-3.40 (7H, m), 3.52-3.62 (2H, m), 3.94-4.03 (2H, m), 7.67-7.74 (2H, m), 8.40 (2H, d, J = 2.0 Hz), 8.48-8.50 (1H, m), 8.85 (1H, d, J = 2.0 Hz), 10.49 (1H, brs), 12.28 (1H, brs), 12.63 (1H, brs). |
| 282 | 0.90 (3H, t, J = 7.3 Hz), 1.51 (2H, brs), 1.64-1.73 (2H, m), 1.91-1.99 (2H, m), 2.33-3.38 (13H, m), 3.97 (2H, d, J = 13.2 Hz), 7.45 (1H, d, J = 1.5 Hz), 7.53 (1H, d, J = 1.0 Hz), 8.40 (1H, d, J = 1.9 Hz), 8.83 (1H, d, J = 2.0 Hz), 12.00-12.50 (1H, br), 12.58 (1H, brs). |
| 284 | 0.95 (3H, t, J = 7.3 Hz), 1.63-1.83 (6H, m), 2.33-2.41 (1H, m), 2.95 (2H, t, J = 11.5 Hz), 3.13-3.42 (8H, m), 3.60 (2H, d, J = 10.8 Hz), 4.07 (2H, d, J = 13.2 Hz), 6.80 (1H, s)7.32 (1H, d, J = 1.5 Hz), 7.58 (1H, d, J = 1.5 Hz), 8.40 (1H, d, J = 1.9 Hz), 8.84 (1H, d, J = 1.9 Hz), 10.65 (1H, brs), 12.68 (1H, s). |
| 285 | 0.95 (3H, t, J = 7.3 Hz), 1.47-1.55 (2H, m), 1.72-1.91 (4H, m), 3.12-3.34 (10H, m), 3.59-3.86 (5H, m), 7.50 (1H, d, J = 1.5 Hz), 7.58 (1H, d, J = 1.5 Hz), 8.39 (1H, d, J = 1.9 Hz), 8.82 (1H, d, J = 1.9 Hz), 10.80 (1H, brs), 12.66 (1H, s). |
| 289 | 1.10-1.20 (1H, m), 1.22-1.36 (2H, m)1.40-1.55 (2H, m), 1.59-1.68 (1H, m), 1.81-1.94 (4H, m), 2.00-2.09 (2H, m), 2.15-2.24 (2H, m), 2.98-3.07 (2H, m), 3.07-3.16 (4H, m), 3.18-3.35 (4H, m), 3.55-3.74 (7H, m), 7.28 (1H, d, J = 8.3 Hz), 7.49 (1H, d, J = 1.5 Hz), 7.57 (1H, d, J = 1.5 Hz), 8.04 (1H, dd, J = 1.9, 8.3 Hz), 8.18 (1H, d, J = 1.9 Hz), 10.82 (1H, brs), 12.63 (1H, s). |
| 290 | 1.06-1.20 (1H, m), 1.22-1.50 (4H, m), 1.56-2.30 (9H, m), 2.39-2.48 (1H, m), 2.75-2.86 (1H, m), 2.80-3.80 (11H, m), 7.23 (1H, d, J = 8.3 Hz), 7.48 (1H, brs), 7.56 (1H, brs), 8.03 (1H, dd, J = 1.9, 8.3 Hz), 8.18 (1H, d, J = 1.9 Hz), 10.50 (1H, brs), 12.28 (1H, brs), 12.68 (1H, s). |
| 292 | 1.08-1.20 (1H, m), 1.21-1.35 (2H, m), 1.38-1.55 (2H, m), 1.58-1.90 (7H, m), 2.10-2.25 (2H, m), 2.22-2.36 (1H, m), 2.68-2.79 (2H, m), 3.20-3.37 (7H, m), 3.42-3.49 (2H, m), |

TABLE 22-continued

| Ex | NMR |
|---|---|
| | 3.50-3.70 (2H, m), 6.82 (1H, brs), 7.25 (1H, d, J = 8.8 Hz), 7.33 (1H, brs), 7.49 (1H, brs), 7.56 (1H, brs), 8.03 (1H, dd, J = 1.9, 8.8 Hz), 8.18 (1H, d, J = 1.9 Hz), 10.62 (1H, brs), 12.61 (1H, s). |
| 293 | 1.08-1.20 (1H, m), 1.20-1.36 (2H, m)1.36-1.53 (2H, m), 1.53-1.68 (3H, m), 1.80-1.93 (4H, m), 2.15-2.25 (2H, m), 2.80-2.91 (2H, m), 3.20-3.40 (9H, m), 3.55-3.63 (2H, m), 3.63-3.71 (1H, m), 7.24 (1H, d, J = 8.3 Hz), 7.49 (1H, d, J = 1.5 Hz), 7.57 (1H, d, J = 1.5 Hz), 8.02 (1H, dd, J = 1.9, 8.3 Hz), 8.18 (1H, d, J = 1.9 Hz), 10.98 (1H, brs), 12.60 (1H, s). |
| 295 | 1.11-1.20 (1H, m), 1.22-1.36 (2H, m), 1.38-1.50 (2H, m), 1.64 (1H, d, J = 12.2 Hz), 1.69-1.80 (2H, m), 1.87 (2H, d, J = 12.2 Hz), 1.91-2.00 (2H, m), 2.17 (2H, d, J = 10.3 Hz), 2.42-3.42 (12H, m), 3.62 (2H, d, J = 9.7 Hz), 7.24 (1H, d, J = 8.3 Hz), 7.50 (1H, d, J = 1.9 Hz), 7.58 (1H, d, J = 1.4 Hz), 8.08 (1H, dd, J = 1.9, 8.3 Hz), 8.36 (1H, d, J = 1.9 Hz), 9.99 (1H, brs), 12.27 (1H, brs), 12.65 (1H, s). |
| 297 | 1.06-1.19 (1H, m), 1.29 (2H, q, J = 13.2 Hz), 1.48 (2H, q, J = 11.2 Hz), 1.64 (1H, d, J = 12.7 Hz), 1.71-1.91 (6H, m), 2.19-2.33 (3H, m), 2.67-2.83 (2H, m), 3.22-3.46 (9H, m), 3.60 (2H, d, J = 7.4 Hz), 6.81 (1H, s), 7.25 (1H, d, J = 8.3 Hz), 7.34 (1H, s), 7.50 (1H, d, J = 1.5 Hz), 7.57 (1H, d, J = 1.5 Hz), 8.08 (1H, dd, J = 2.2, 8.6 Hz), 8.36 (1H, d, J = 1.9 Hz), 10.86 (1H, brs), 12.64 (1H, s). |
| 298 | 1.14-1.19 (1H, m), 1.29 (2H, q, J = 11.7 Hz), 1.48 (2H, q, J = 11.2 Hz), 1.64 (1H, d, J = 12.7 Hz), 1.78-1.91 (4H, m), 1.96-2.01 (2H, m), 2.20 (2H, d, J = 10.2 Hz), 3.09-3.35 (12H, m), 3.60 (2H, d, J = 8.8 Hz), 7.49 (1H, d, J = 1.5 Hz), 7.57 (1H, d, J = 1.5 Hz), 7.80-7.86 (2H, m), 10.96 (1H, brs), 12.68 (1H, s). |
| 299 | 1.07-1.18 (1H, m), 1.29 (2H, q, J = 12.8 Hz), 1.47 (2H, q, J = 11.2 Hz), 1.59-1.72 (3H, m), 1.82-1.94 (4H, m), 2.19 (2H, d, J = 10.2 Hz), 2.42-2.46 (1H, m), 3.13 (2H, d, J = 11.3 Hz), 3.26-3.41 (9H, m), 3.60 (2H, brs), 7.49 (1H, d, J = 1.5 Hz), 7.57 (1H, d, J = 1.5 Hz), 7.77-7.86 (2H, m), 10.72 (1H, brs), 12.27 (1H, brs), 12.65 (1H, s). |
| 301 | 1.07.-1.19 (1H, m), 1.29 (2H, q, J = 12.9 Hz), 1.47 (2H, q, J = 11.0 Hz), 1.57-1.72 (3H, m), 1.72-1.81 (2H, m), 1.86 (2H, d, J = 13.1 Hz), 2.18-2.33 (3H, m), 3.09 (2H, t, J = 11.7 Hz), 3.22-3.44 (9H, m), 3.59 (2H, brs), 6.81 (1H, s), 7.31 (1H, s), 7.50 (1H, d, J = 1.5 Hz), 7.57 (1H, d, J = 1.4 Hz), 7.77-7.86 (2H, m), 10.70 (1H, brs), 12.66 (1H, s). |
| 302 | 1.08-1.20 (1H, m), 1.21-1.36 (2H, m), 1.40-1.55 (2H, m), 1.59-1.68 (1H, m), 1.78-1.91 (4H, m), 1.95-2.05 (2H, m), 2.14-2.25 (2H, m), 3.09-3.21 (3H, m), 3.21-3.45 (9H, m), 3.55-3.65 (2H, m), 7.50 (1H, d, J = 1.5 Hz), 7.57 (1H, d, J = 1.5 Hz), 7.93 (1H, dd, J = 2.0, 12.7 Hz), 8.07 (1H, brs), 10.81 (1H, brs), 12.73 (1H, s). |
| 303 | 1.08-1.20 (1H, m), 1.22-1.37 (2H, m), 1.42-1.55 (2H, m), 1.59-1.76 (3H, m), 1.81-1.95 (4H, m), 2.16-2.25 (2H, m), 2.40-2.48 (1H, m), 3.08-3.17 (2H, m), 3.24-3.36 (7H, m), 3.46-3.65 (4H, m), 7.49 (1H, d, J = 1.4 Hz), 7.57 (1H, d, J = 1.4 Hz), 7.89 (1H, dd, J = 2.0, 13.2 Hz), 8.06 (1H, d, J = 2.0 Hz), 10.90 (1H, brs), 12.25 (1H, brs), 12.72 (1H, s). |
| 305 | 1.08-1.20 (1H, m), 1.20-1.35 (2H, m), 1.38-1.52 (2H, m), 1.58-1.67 (1H, m), 2.10-2.24 (2H, m), 2.25-2.36 (1H, m), 3.03-3.14 (2H, m), 3.15-3.35 (9H, m), 3.50-3.70 (2H, m), 6.80 (1H, brs), 7.30 (1H, brs), 7.48 (1H, brs), 7.56 (1H, brs), 7.90 (1H, dd, J = 2.0, 13.8 Hz), 8.06 (1H, brs), 10.80 (1H, brs), 12.69 (1H, s). |
| 309 | 1.07-1.20 (1H, m), 1.21-1.35 (2H, m), 1.38-1.53 (2H, m), 1.58-1.67 (1H, m), 1.80-1.92 (2H, m), 2.08-2.24 (2H, m), 2.75-2.88 (4H, m), 3.16-3.92 (15H, m), 7.49 (1H, d, J = 1.4 Hz), 7.53 (1H, d, J = 1.4 Hz), 7.92 (1H, dd, J = 2.0, 13.2 Hz), 8.06 (1H, s), 12.7 (1H, s). |
| 311 | 1.08-1.18 (1H, m), 1.22-1.35 (2H, m), 1.42-1.56 (2H, m), 1.58-1.68 (2H, m), 1.82-1.92 (2H, m), 2.18-2.26 (2H, m), 3.24-3.50 (9H, m), 3.51-3.68 (8H, m), 4.04 (2H, s), 7.50 (1H, d, J = 1.5 Hz), 7.58 (1H, d, J = 1.5 Hz), 7.72 (1H, s), 7.95 (1H, dd, J = 1.9, 12.7 Hz), 8.05 (1H, s), 8.10 (1H, s), 8.32 (1H, s), 10.33 (1H, brs), 11.10 (1H, brs), 12.8 (1H, s). |
| 313 | 1.05-1.08 (1H, m), 1.24-1.35 (2H, m)1.43-1.52 (2H, m), 1.60-1.69 (1H, m), 1.82-1.92 (2H, m), 2.12-2.22 (2H, m), 3.13-3.24 (4H, m), 3.31 (3H, s), 3.26-3.35 (3H, m), 3.46-3.64 (10H, m), 4.14 (2H, s), 7.50 (1H, d, J = 1.4 Hz), 7.58 (1H, d, J = 1.4 Hz), 7.94 (1H, dd, J = 2.2, 12.9 Hz), 8.09 (1H, s), 1011 (1H, brs), 12.76 (1H, brs). |
| 316 | 1.01-1.20 (1H, m), 1.21-1.37 (2H, m), 1.41-1.57 (2H, m), 1.58-1.67 (1H, m), 1.75-1.92 (2H, m), 2.14-2.28 (2H, m), 3.03-3.15 (4H, m), 3.21-3.44 (11H, m), 3.55-3.64 (2H, m), 6.88 (2H, m), 7.49 (1H, d, J = 1.4 Hz), 7.57 (1H, d, J = 1.4 Hz), 7.95 (1H, dd, J = 2.0, 12.7 Hz), 8.08 (1H, brs), 11.2 (1H, brs), 12.7 (1H, brs). |
| 322 | 1.06-1.20 (1H, m), 1.22-1.36 (2H, m), 1.40-1.54 (2H, m), 1.58-1.68 (1H, m), 1.81-2.00 (4H, m), 2.14-2.24 (2H, m), 3.20-3.38 (7H, m), 3.54-3.64 (3H, m), 3.73-3.81 (1H, m), 3.82-3.91 (2H, m), 4.33-4.39 (1H, m), 7.49 (1H, d, J = 1.5 Hz), 7.56 (1H, d, J = 1.5 Hz), 8.29 (1H, d, J = 2.0 Hz), 8.74 (1H, d, J = 2.0 Hz), 10.70 (1H, brs), 12.51 (1H, s). |
| 328 | 1.05-1.20 (1H, m), 1.22-1.36 (4H, m), 1.41-1.55 (2H, m), 1.58-1.70 (2H, m), 1.73-1.81 (2H, m), 1.82-1.91 (2H, m), 2.17-2.26 (2H, m), 2.90 (2H, t, J = 11.2 Hz), 3.23-3.36 (9H, m), 3.60 (2H, d, J = 9.8 Hz), 4.08 (2H, d, J = 12.7 Hz), 7.49 (1H, d, J = 1.4 Hz), 7.56 (1H, d, J = 1.4 Hz), 8.38 (1H, d, J = 2.0 Hz), 8.82 (1H, d, J = 2.0 Hz), 11.03 (1H, brs), 12.65 (1H, brs). |
| 331 | 1.05-1.20 (1H, m), 1.22-1.36 (2H, m), 1.41-1.54 (2H, m), 1.58-1.74 (3H, m), 1.77-1.92 (4H, m), 2.16-2.24 (2H, m), 2.34-2.42 (1H, m), 2.95 (2H, t, J = 12.2 Hz), 3.25-3.36 (7H, m), 3.52-3.64 (2H, m), 4.07 (2H, d, J = 12.2 Hz), 6.80 (1H, s), 7.32 (1H, s), 7.49 (1H, d, J = 1.5 Hz), 7.57 (1H, d, J = 1.5 Hz), 8.40 (1H, d, J = 2.4 Hz), 8.83 (1H, d, J = 2.4 Hz), 10.73 (1H, brs), 12.67 (1H, s). |
| 332 | 1.08-1.19 (1H, m), 1.29 (2H, q, J = 13.0 Hz), 1.47 (2H, q, J = 11.2 Hz), 1.60-1.82 (5H, m), 1.87 (2H, d, J = 13.2 Hz), 2.19 (2H, d, J = 10.7 Hz), 2.32-2.41 (1H, m), 2.58 (3H, d, J = 4.4 Hz), 2.94 (2H, t, J = 11.5 Hz), |

TABLE 22-continued

| Ex | NMR |
|---|---|
| | 3.24-3.66 (9H, m), 4.08 (2H, d, J = 12.7 Hz), 7.49 (1H, d, J = 1.5 Hz), 7.57 (1H, d, J = 1.5 Hz), 7.79 (1H, q, J = 4.6 Hz), 8.40 (1H, d, J = 1.9 Hz), 8.83 (1H, d, J = 1.9 Hz), 10.68 (1H, brs), 12.67 (1H, s). |
| 333 | 0.84 (3H, t, J = 7.3 Hz), 1.08-1.21 (1H, m), 1.22-1.34 (2H, m), 1.35-1.54 (4H, m), 1.59-1.82 (5H, m), 1.83-1.92 (2H, m), 2.14-2.23 (2H, m), 2.34-2.43 (1H, m), 2.90-2.99 (2H, m), 3.01 (2H, q, J = 6.9 Hz), 3.20-3.60 (7H, m), 3.55-3.65 (2H, m), 4.04-4.12 (2H, m), 7.50 (1H, d, J = 1.5 Hz), 7.58 (1H, d, J = 1.5 Hz), 7.83 (1H, t, J = 5.8 Hz), 8.40 (1H, d, J = 2.4 Hz), 8.83 (1H, d, J = 2.4 Hz), 10.53 (1H, brs), 12.68 (1H, brs). |
| 338 | 1.13-1.20 (1H, m), 1.21-1.35 (2H, m), 1.42-1.55 (2H, m), 1.58-1.74 (7H, m), 2.16-2.23 (2H, m), 2.38-2.46 (1H, m)2.88-3.00 (2H, m), 3.18-3.36 (7H, m), 3.25 (3H, s), 3.48-3.68 (6H, m), 4.08-4.13 (2H, m), 7.49 (1H, d, J = 1.4 Hz), 7.56 (1H, d, J = 1.4 Hz), 7.94 (1H, t, J = 5.8 Hz), 8.39 (1H, d, J = 2.0 Hz), 8.83 (1H, d, J = 2.0 Hz), 10.81 (1H, brs), 12.66 (1H, brs). |
| 339 | 1.11 (3H, t, J = 6.9 Hz), 1.07-1.21 (1H, m), 1.23-1.36 (2H, m), 1.42-1.52 (2H, m), 1.60-1.91 (7H, m), 2.14-2.27 (2H, m)2.35-2.48 (1H, m), 2.87-3.00 (2H, m), 3.20 (2H, q, J = 5.8 Hz), 3.20-3.42 (9H, m), 3.43 (2H, q, J = 6.9 Hz), 3.54-3.66 (2H, m), 4.00-4.14 (2H, m), 7.49 (1H, d, J = 1.4 Hz), 7.58 (1H, d, J = 1.4 Hz), 7.92 (1H, t, J = 5.8 Hz), 8.40 (1H, d, J = 1.9 Hz), 8.82 (1H, d, J = 1.9 Hz), 11.00 (1H, brs), 12.67 (1H, brs). |
| 340 | 1.04-1.20 (1H, m), 1.23-1.36 (2H, m), 1.46-1.56 (2H, m), 1.57-1.92 (7H, m), 1.63 (2H, t, J = 6.9 Hz), 2.16-2.28 (2H, m)2.32-2.42 (1H, m), 2.85-2.98 (2H, m), 3.06-3.13 (2H, m), 3.22 (3H, s), 3.21-3.45 (9H, m), 3.54-3.67 (2H, m), 4.02-4.20 (2H, m), 7.49 (1H, d, J = 1.5 Hz), 7.56 (1H, d, J = 1.5 Hz), 7.88 (1H, t, J = 5.5 Hz), 8.39 (1H, d, J = 2.0 Hz), 8.82 (1H, d, J = 2.0 Hz), 11.27 (1H, brs), 12.65 (1H, brs). |
| 344 | 1.07-1.19 (1H, m), 1.29 (2H, q, J = 12.1 Hz), 1.48 (2H, q, J = 11.2 Hz), 1.60-1.78 (5H, m), 1.86 (2H, d, J = 12.7 Hz), 2.20 (2H, d, J = 10.2 Hz), 2.83 (3H, s), 2.89-3.06 (3H, m), 3.07 (3H, s), 3.22-3.38 (7H, m), 3.60 (2H, d, J = 7.8 Hz), 4.09 (2H, d, J = 13.2 Hz), 7.49 (1H, d, J = 1.4 Hz), 7.57 (1H, d, J = 1.4 Hz), 8.39 (1H, d, J = 2.5 Hz), 8.83 (1H, d, J = 2.4 Hz), 10.88 (1H, brs), 12.66 (1H, s). |
| 350 | 1.07-1.20 (1H, m), 1.22-1.36 (2H, m), 1.41-1.56 (4H, m), 1.60-1.67 (1H, m), 1.80-1.92 (4H, m), 2.15-2.24 (2H, m), 3.13-3.37 (9H, m), 3.55-3.63 (2H, m), 3.68-3.76 (1H, m), 3.79-3.87 (2H, m), 7.49 (1H, d, J = 1.4 Hz), 7.57 (1H, d, J = 1.4 Hz), 8.38 (1H, d, J = 2.4 Hz), 8.82 (1H, d, J = 2.4 Hz), 10.92 (1H, brs), 12.66 (1H, s). |
| 353 | 1.06-1.20 (1H, m), 1.22-1.37 (2H, m), 1.42-1.57 (4H, m), 1.59-1.68 (1H, m), 1.81 (3H, s), 1.82-1.90 (4H, m), 2.16-226 (2H, m), 3.07 (2H, t, J = 11.2 Hz), 3.21-3.41 (7H, m), 3.54-3.64 (2H, m), 3.82-4.08 (3H, m), 7.49 (1H, d, J = 1.4 Hz), 7.57 (1H, d, J = 1.4 Hz), 7.90 (1H, d, J = 7.8 Hz), 8.40 (1H, d, J = 1.9 Hz), 8.84 (1H, d, J = 1.9 Hz), 11.06 (1H, brs), 12.67 (1H, s). |
| 358 | 1.05-1.20 (1H, m), 1.21-1.36 (2H, m), 1.42-1.55 (2H, m), 1.57-1.67 (1H, m), 1.81-1.92 (2H, m), 2.18-2.24 (2H, m), 2.94-3.03 (4H, m), 3.18-3.80 (15H, m), 7.49 (1H, d, J = 1.4 Hz), 7.57 (1H, d, J = 1.4 Hz), 8.42 (1H, d, J = 2.2 Hz), 8.88 (1H, d, J = 2.2 Hz), 11.16 (1H, brs), 12.71 (1H, brs). |
| 362 | 1.06-1.20 (1H, m), 1.22-1.36 (2H, m), 1.40-1.54 (2H, m), 1.58-1.69 (1H, m), 1.81-1.92 (2H, m), 2.13-2.24 (2H, m), 3.23-3.38 (9H, m), 3.57-3.63 (2H, m), 3.77 (2H, t, J = 5.4 Hz), 4.05 (2H, brs), 7.49 (1H, d, J = 1.5 Hz), 7.57 (1H, d, J = 1.5 Hz), 8.05 (1H, brs), 8.45 (1H, d, J = 1.9 Hz), 8.86 (1H, d, J = 1.9 Hz), 10.62 (1H, brs), 12.73 (1H, s). |
| 372 | 1.07-1.21 (1H, m), 1.20-1.37 (2H, m), 1.37-1.52 (2H, m), 1.60-1.77 (1H, m), 1.83-1.92 (2H, m), 2.10-2.23 (2H, m), 2.53-2.54 (2H, m), 3.15-3.37 (9H, m), 3.57-3.68 (6H, m), 7.50 (1H, s), 7.57 (1H, s), 7.63-7.70 (1H, m), 8.43 (1H, s)8.82 (1H, s), 10.26 (1H, brs), 12.68 (1H, brs). |

The structures of the compounds of the invention are shown in the following Tables 23-33. These compounds can be easily prepared by the above production methods, methods described in Examples, or methods that are self-evident to an ordinarily skilled person, or its variations.

In the Tables, No indicates the number of compound, and $R^J$, $R^K$, $R^L$, $R^M$, $R^N$, $R^O$, $R^P$, $R^Q$, $R^R$, $R^S$, $R^T$, $R^{AA}$, $R^{BB}$, $R^{CC}$, $R^{DD}$, $R^{EE}$, $R^{FF}$, $R^{GG}$ indicate substituent groups in the general Formula. Thus, for examples, in Table 23, "(No: $R^J$)= (A0001:HO—$CH_2$—O)" indicates that "the compound of A0001 has a hydroxymethoxy group as a substituent group $R^J$ in the general Formula".

TABLE 23

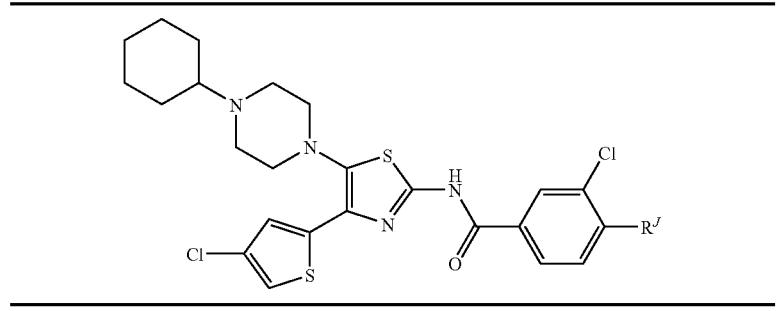

(No: $R^J$) =
(A0001: HO—$CH_2$—O), (A0002: MeO—$CH_2$—O), (A0003: $EtO_2C$—$CH_2$—O), (A0004: $HO_2C$—$CH_2$—O), (A0005: $H_2NOC$—$CH_2$—O), (A0006: cyano-$CH_2$—O), (A0007: MeHNOC—$CH_2$—O), (A0008: $Me_2NOC$—$CH_2$—O), (A0009: $F_3C$—$CH_2$—O), (A0010: HO—$(CH_2)_2$—O), (A0011: MeO—$(CH_2)_2$—O), (A0012: $EtO_2C$—$(CH_2)_2$—O), (A0013: $HO_2C$—$(CH_2)_2$—O), (A0014: $H_2NOC$—$(CH_2)_2$—O), (A0015: cyano-$(CH_2)_2$—O), (A0016: MeHNOC—$(CH_2)_2$—O), (A0017: $Me_2NOC$—$(CH_2)_2$—O), (A0018: $F_3C$—$(CH_2)_2$—O), (A0019: HO—$(CH_2)_3$—O), (A0020: MeO—$(CH_2)_3$—O), (A0021: $EtO_2C$—$(CH_2)_3$—O), (A0022: $HO_2C$—$(CH_2)_3$—O), (A0023: $H_2NOC$—$(CH_2)_3$—O), (A0024: cyano-$(CH_2)_3$—O), (A0025: MeHNOC—$(CH_2)_3$—O), (A0026: $Me_2NOC$—$(CH_2)_3$—O), (A0027: $F_3C$—$(CH_2)_3$—O), (A0028: 1-HO-cHex-O), (A0029: 1-MeO-cHex-O), (A0030: 1-$EtO_2C$-cHex-O), (A0031: 1-$HO_2C$-cHex-O), (A0032: 1-$H_2NOC$-cHex-O), (A0033: 1-cyano-cHex-O), (A0034: 1-MeHNOC-cHex-O), (A0035: 1-$Me_2NOC$-cHex-O), (A0036: 1-$F_3C$-cHex-O), (A0037: 2-HO-cHex-O), (A0038: 2-MeO-cHex-O), (A0039: 2-$EtO_2C$-cHex-O), (A0040: 2-$HO_2C$-cHex-O), (A0041: 2-$H_2NOC$-cHex-O), (A0042: 2-cyano-cHex-O), (A0043: 2-MeHNOC-cHex-O), (A0044: 2-$Me_2NOC$-cHex-O), (A0045: 2-$F_3C$-cHex-O), (A0046: 3-HO-cHex-O), (A0047: 3-MeO-cHex-O), (A0048: 3-$EtO_2C$-cHex-O), (A0049: 3-$HO_2C$-cHex-O), (A0050: 3-$H_2NOC$-cHex-O), (A0051: 3-cyano-cHex-O), (A0052: 3-MeHNOC-cHex-O), (A0053: 3-$Me_2NOC$-cHex-O), (A0054: 3-$F_3C$-cHex-O), (A0055: 4-HO-cHex-O), (A0056: 4-MeO-cHex-O), (A0057: 4-$EtO_2C$-cHex-O), (A0058: 4-$HO_2C$-cHex-O), (A0059: 4-$H_2NOC$-cHex-O), (A0060: 4-cyano-cHex-O), (A0061: 4-MeHNOC-cHex-O), (A0062: 4-$Me_2NOC$-cHex-O), (A0063: 4-$F_3C$-cHex-O), (A0064: 3-HO-cPen-O), (A0065: 3-MeO-cPen-O), (A0066: 3-$EtO_2C$-cPen-O), (A0067: 3-$HO_2C$-cPen-O), (A0068: 3-$H_2NOC$-cPen-O), (A0069: 3-cyano-cPen-O), (A0070: 3-MeHNOC-cPen-O), (A0071: 3-$Me_2NOC$-cPen-O), (A0072: 3-$F_3C$-cPen-O), (A0073: 3-HO-cBu-O), (A0074: 3-MeO-cBu-O), (A0075: 3-$EtO_2C$-cBu-O), (A0076: 3-$HO_2C$-cBu-O), (A0077: 3-$H_2NOC$-cBu-O), (A0078: 3-cyano-cBu-O), (A0079: 3-MeHNOC-cBu-O), (A0080: 3-$Me_2NOC$-cBu-O), (A0081: 3-$F_3C$-cBu-O), (A0082: 2-HO-cPr-O), (A0083: 2-MeO-cPr-O), (A0084: 2-$EtO_2C$-cPr-O), (A0085: 2-$HO_2C$-cPr-O), (A0086: 2-$H_2NOC$-cPr-O), (A0087: 2-cyano-cPr-O), (A0088: 2-MeHNOC-cPr-O), (A0089: 2-$Me_2NOC$-cPr-O), (A0090: 2-$F_3C$-cPr-O), (A0091: HO—$CH_2$—HN), (A0092: MeO—$CH_2$—HN), (A0093: $EtO_2C$—$CH_2$—HN), (A0094: $HO_2C$—$CH_2$—HN), (A0095: $H_2NOC$—$CH_2$—HN), (A0096: cyano-$CH_2$—HN), (A0097: MeHNOC—$CH_2$—HN), (A0098: $Me_2NOC$—$CH_2$—HN), (A0099: $F_3C$—$CH_2$—HN), (A0100: HO—$(CH_2)_2$—HN), (A0101: MeO—$(CH_2)_2$—HN), (A0102: $EtO_2C$—$(CH_2)_2$—HN), (A0103: $HO_2C$—$(CH_2)_2$—HN), (A0104: $H_2NOC$—$(CH_2)_2$—HN), (A0105: cyano-$(CH_2)_2$—HN), (A0106: MeHNOC—$(CH_2)_2$—HN), (A0107: Me2NOC—$(CH_2)_2$—HN), (A0108: $F_3C$—$(CH_2)_2$—HN), (A0109: HO—$(CH_2)_3$—HN), (A0110: MeO—$(CH_2)_3$—HN), (A0111: EtO2C—$(CH_2)_3$—HN), (A0112: $HO_2C$—$(CH_2)_3$—HN), (A0113: $H_2NOC$—$(CH_2)_3$—HN), (A0114: cyano-$(CH_2)_3$—HN), (A0115: MeHNOC—$(CH_2)_3$—HN), (A0116: $Me_2NOC$—$(CH_2)_3$—HN), (A0117: $F_3C$—$(CH_2)_3$—HN), (A0118: 1-HO-cHex-HN), (A0119: 1-MeO-cHex-HN), (A0120: 1-$EtO_2C$-cHex-HN), (A0121: 1-$HO_2C$-cHex-HN), (A0122: 1-$H_2NOC$-cHex-HN), (A0123: 1-cyano-cHex-HN), (A0124: 1-MeHNOC-cHex-HN), (A0125: 1-$Me_2NOC$-cHex-HN), (A0126: 1-$F_3C$-cHex-HN), (A0127: 2-HO-cHex-HN), (A0128: 2-MeO-cHex-HN), (A0129: 2-$EtO_2C$-cHex-HN), (A0130: 2-$HO_2C$-cHex-HN), (A0131: 2-$H_2NOC$-cHex-HN), (A0132: 2-cyano-cHex-HN), (A0133: 2-MeHNOC-cHex-HN), (A0134: 2-$Me_2NOC$-cHex-HN), (A0135: 2-$F_3C$-cHex-HN), (A0136: 3-HO-cHex-HN), (A0137: 3-MeO-cHex-HN), (A0138: 3-$EtO_2C$-cHex-HN), (A0139: 3-$HO_2C$-cHex-HN), (A0140: 3-$H_2NOC$-cHex-HN), (A0141: 3-cyano-cHex-HN), (A0142: 3-MeHNOC-cHex-HN), (A0143: 3-$Me_2NOC$-cHex-HN), (A0144: 3-$F_3C$-cHex-HN), (A0145: 4-HO-cHex-HN), (A0146: 4-MeO-cHex-HN), (A0147: 4-$EtO_2C$-cHex-HN), (A0148: 4-$HO_2C$-cHex-HN), (A0149: 4-$H_2NOC$-cHex-HN), (A0150: 4-cyano-cHex-HN), (A0151: 4-MeHNOC-cHex-HN), (A0152: 4-$Me_2NOC$-cHex-HN), (A0153: 4-$F_3C$-cHex-HN), (A0154: 3-HO-cPen-HN), (A0155: 3-MeO-cPen-HN), (A0156: 3-$EtO_2C$-cPen-HN), (A0157: 3-$HO_2C$-cPen-HN), (A0158: 3-$H_2NOC$-cPen-HN), (A0159: 3-cyano-cPen-HN), (A0160: 3-MeHNOC-cPen-HN), (A0161: 3-$Me_2NOC$-cPen-HN), (A0162: 3-$F_3C$-cPen- TABLE 23-continued

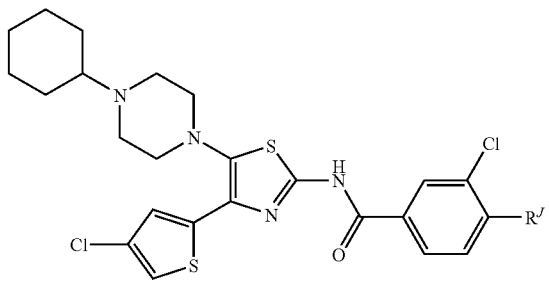

HN), (A0163: 3-HO-cBu-HN), (A0164: 3-MeO-cBu-HN), (A0165: 3-EtO$_2$C-cBu-HN), (A0166: 3-HO$_2$C-cBu-HN), (A0167: 3-H$_2$NOC-cBu-HN), (A0168: 3-cyano-cBu-HN), (A0169: 3-MeHNOC-cBu-HN), (A0170: 3-Me$_2$NOC-cBu-HN), (A0171: 3-F$_3$C-cBu-HN), (A0172: 2-HO-cPr-HN), (A0173: 2-MeO-cPr-HN), (A0174: 2-EtO$_2$C-cPr-HN), (A0175: 2-HO$_2$C-cPr-HN), (A0176: 2-H$_2$NOC-cPr-HN), (A0177: 2-cyano-cPr-HN), (A0178: 2-MeHNOC-cPr-HN), (A0179: 2-Me$_2$NOC-cPr-HN), (A0180: 2-F$_3$C-cPr-HN), (A0181: HO—CH$_2$-MeN), (A0182: MeO—CH$_2$-MeN), (A0183: EtO$_2$C—CH$_2$-MeN), (A0184: HO$_2$C—CH$_2$-MeN), (A0185: H$_2$NOC—CH$_2$-MeN), (A0186: cyano-CH$_2$-MeN), (A0187: MeHNOC—CH$_2$-MeN), (A0188: Me$_2$NOC—CH$_2$-MeN), (A0189: F$_3$C—CH$_2$-MeN), (A0190: HO—(CH$_2$)$_2$-MeN), (A0191: MeO—(CH$_2$)$_2$-MeN), (A0192: EtO$_2$C—(CH$_2$)$_2$-MeN), (A0193: HO$_2$C—(CH$_2$)$_2$-MeN), (A0194: H$_2$NOC—(CH$_2$)$_2$-MeN), (A0195: cyano-(CH$_2$)$_2$-MeN), (A0196: MeHNOC—(CH$_2$)$_2$-MeN), (A0197: Me$_2$NOC—(CH$_2$)$_2$-MeN), (A0198: F$_3$C—(CH$_2$)$_2$-MeN), (A0199: HO—(CH$_2$)$_3$-MeN), (A0200: MeO—(CH$_2$)$_3$-MeN), (A0201: EtO$_2$C—(CH$_2$)$_3$-MeN), (A0202: HO$_2$C—(CH$_2$)$_3$-MeN), (A0203: H$_2$NOC—(CH$_2$)$_3$-MeN), (A0204: cyano-(CH$_2$)$_3$-MeN), (A0205: MeHNOC—(CH$_2$)$_3$-MeN), (A0206: Me$_2$NOC—(CH$_2$)$_3$-MeN), (A0207: F$_3$C—(CH$_2$)$_3$-MeN), (A0208: 1-HO-cHex-MeN), (A0209: 1-MeO-cHex-MeN), (A0210: 1-EtO$_2$C-cHex-MeN), (A0211: 1-HO$_2$C-cHex-MeN), (A0212: 1-H$_2$NOC-cHex-MeN), (A0213: 1-cyano-cHex-MeN), (A0214: 1-MeHNOC-cHex-MeN), (A0215: 1-Me$_2$NOC-cHex-MeN), (A0216: 1-F$_3$C-cHex-MeN), (A0217: 2-HO-cHex-MeN), (A0218: 2-MeO-cHex-MeN), (A0219: 2-EtO$_2$C-cHex-MeN), (A0220: 2-HO$_2$C-cHex-MeN), (A0221: 2-H$_2$NOC-cHex-MeN), (A0222: 2-cyano-cHex-MeN), (A0223: 2-MeHNOC-cHex-MeN), (A0224: 2-Me$_2$NOC-cHex-MeN), (A0225: 2-F$_3$C-cHex-MeN), (A0226: 3-HO-cHex-MeN), (A0227: 3-MeO-cHex-MeN), (A0228: 3-EtO$_2$C-cHex-MeN), (A0229: 3-HO$_2$C-cHex-MeN), (A0230: 3-H$_2$NOC-cHex-MeN), (A0231: 3-cyano-cHex-MeN), (A0232: 3-MeHNOC-cHex-MeN), (A0233: 3-Me$_2$NOC-cHex-MeN), (A0234: 3-F$_3$C-cHex-MeN), (A0235: 4-HO-cHex-MeN), (A0236: 4-MeO-cHex-MeN), (A0237: 4-EtO$_2$C-cHex-MeN), (A0238: 4-HO$_2$C-cHex-MeN), (A0239: 4-H$_2$NOC-cHex-MeN), (A0240: 4-cyano-cHex-MeN), (A0241: 4-MeHNOC-cHex-MeN), (A0242: 4-Me$_2$NOC-cHex-MeN), (A0243: 4-F$_3$C-cHex-MeN), (A0244: 3-HO-cPen-MeN), (A0245: 3-MeO-cPen-MeN), (A0246: 3-EtO$_2$C-cPen-MeN), (A0247: 3-HO$_2$C-cPen-MeN), (A0248: 3-H$_2$NOC-cPen-MeN), (A0249: 3-cyano-cPen-MeN), (A0250: 3-MeHNOC-cPen-MeN), (A0251: 3-Me$_2$NOC-cPen-MeN), (A0252: 3-F$_3$C-cPen-MeN), (A0253: 3-HO-cBu-MeN), (A0254: 3-MeO-cBu-MeN), (A0255: 3-EtO$_2$C-cBu-MeN), (A0256: 3-HO$_2$C-cBu-MeN), (A0257: 3-H$_2$NOC-cBu-MeN), (A0258: 3-cyano-cBu-MeN), (A0259: 3-MeHNOC-cBu-MeN), (A0260: 3-Me$_2$NOC-cBu-MeN), (A0261: 3-F$_3$C-cBu-MeN), (A0262: 2-HO-cPr-MeN), (A0263: 2-MeO-cPr-MeN), (A0264: 2-EtO$_2$C-cPr-MeN), (A0265: 2-HO$_2$C-cPr-MeN), (A0266: 2-H$_2$NOC-cPr-MeN), (A0267: 2-cyano-cPr-MeN), (A0268: 2-MeHNOC-cPr-MeN), (A0269: 2-Me$_2$NOC-cPr-MeN), (A0270: 2-F$_3$C-cPr-MeN), (A0271: (oxetan-3-yl)-O), (A0272: (tetrahydrofuran-3-yl)-O), (A0273: (tetrahydro-2H-pyran-3-yl)-O), (A0274: (tetrahydro-2H-pyran-4-yl)-O), (A0275: (oxetan-2-yl)-CH$_2$—O), (A0276: (oxetan-3-yl)-CH$_2$—O), (A0277: (tetrahydrofuran-2-yl)-CH$_2$—O), (A0278: (tetrahydrofuran-3-yl)-CH$_2$—O), (A0279: (tetrahydro-2H-pyran-2-yl)-CH$_2$—O), (A0280: (tetrahydro-2H-pyran-3-yl)-CH$_2$—O), (A0281: (tetrahydro-2H-pyran-4-yl)-CH$_2$—O), (A0282: (morpholin-2-yl)-CH$_2$—O), (A0283: (morpholin-3-yl)-CH$_2$—O), (A0284: mor-CH$_2$—O), (A0285: (1,4-dioxan-2-yl)-CH$_2$—O), (A0286: (oxetan-2-yl)-(CH$_2$)$_2$—O), (A0287: (oxetan-3-yl)-HN), (A0288: (tetrahydrofuran-3-yl)-HN), (A0289: (tetrahydro-2H-pyran-3-yl)-HN), (A0290: (tetrahydro-2H-pyran-4-yl)-HN), (A0291: (oxetan-2-yl)-CH$_2$—HN), (A0292: (oxetan-3-yl)-CH$_2$—HN), (A0293: (tetrahydrofuran-2-yl)-CH$_2$—HN), (A0294: (tetrahydrofuran-3-yl)-CH$_2$—HN), (A0295: (tetrahydro-2H-pyran-2-yl)-CH$_2$—HN), (A0296: (tetrahydro-2H-pyran-3-yl)-CH$_2$—HN), (A0297: (tetrahydro-2H-pyran-4-yl)-CH$_2$—HN), (A0298: (morpholin-2-yl)-CH$_2$—HN), (A0299: (morpholin-3-yl)-CH$_2$—HN), (A0300: mor-CH$_2$—HN), (A0301: (1,4-dioxan-2-yl)-CH$_2$—HN), (A0302: (oxetan-3-yl)-MeN), (A0303: (tetrahydrofuran-3-yl)-MeN), (A0304: (tetrahydro-2H-pyran-3-yl)-MeN), (A0305: (tetrahydro-2H-pyran-4-yl)-MeN), (A0306: (oxetan-2-yl)-CH$_2$-MeN), (A0307: (oxetan-3-yl)-CH$_2$-MeN), (A0308: (tetrahydrofuran-2-yl)-CH$_2$-MeN), (A0309: (tetrahydrofuran-3-yl)-CH$_2$-MeN), (A0310: (tetrahydro-2H-pyran-2-yl)-CH$_2$-MeN), (A0311: (tetrahydro-2H-pyran-3-yl)-CH$_2$-MeN), (A0312: (tetrahydro-2H-pyran-4-yl)-CH$_2$-MeN), (A0313: (morpholin-2-yl)-CH$_2$-MeN), (A0314: (morpholin-3-yl)-CH$_2$-MeN), (A0315: mor-CH$_2$-MeN), (A0316: (1,4-dioxan-2-yl)-CH$_2$-MeN), (A0317: HO$_2$C—CH$_2$CH(OH)—O), (A0318: H$_2$NOC—CH$_2$CH(OH)—O), (A0319: cyano-CH$_2$CH(OH)—O), (A0320: HO$_2$C—CH$_2$CH(OMe)-O), (A0321: H$_2$NOC—CH$_2$CH(OMe)-O), (A0322: cyano-CH$_2$CH(OMe)-O), (A0323: HO—CH$_2$CH(OH)CH$_2$—O), (A0324: MeO—CH$_2$CH(OH)CH$_2$—O), (A0325: HO$_2$C—CH$_2$CH(OH)CH$_2$—O), (A0326: H$_2$NOC—CH$_2$CH(OH)CH$_2$—

TABLE 23-continued

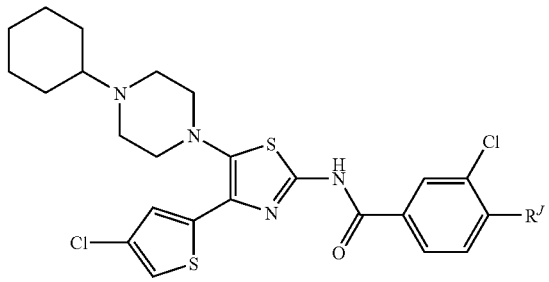

O), (A0327: cyano-CH$_2$CH(OH)CH$_2$—O), (A0328: HO—CH$_2$CH(OMe)CH$_2$—
O), (A0329: MeO—OH$_2$CH(OMe)CH$_2$—O), (A0330: HO$_2$C—CH$_2$CH(OMe)CH$_2$—
O), (A0331: H$_2$NOC—CH$_2$CH(OMe)CH$_2$—O), (A0332: cyano-CH$_2$CH(OMe)CH$_2$—
O), (A0333: HO$_2$C—CH$_2$CH(OH)—HN), (A0334: H$_2$NOC—CH$_2$CH(OH)—
HN), (A0335: cyano-CH$_2$CH(OH)—HN), (A0336: HO$_2$C—CH$_2$CH(OMe)-
HN), (A0337: H$_2$NOC—CH$_2$CH(OMe)-HN), (A0338: cyano-CH$_2$CH(OMe)-
HN), (A0339: HO—CH$_2$CH(OH)CH$_2$—HN), (A0340: MeO—CH$_2$CH(OH)CH$_2$—
HN), (A0341: HO$_2$C—CH$_2$CH(OH)CH$_2$—HN), (A0342: H$_2$NOC—CH$_2$CH(OH)CH$_2$—
HN), (A0343: cyano-CH$_2$CH(OH)CH$_2$—HN), (A0344: HO—CH$_2$CH(OMe)CH$_2$—
HN), (A0345: MeO—CH$_2$CH(OMe)CH$_2$—HN), (A0346: HO$_2$C—CH$_2$CH(OMe)CH$_2$—
HN), (A0347: H$_2$NOC—CH$_2$CH(OMe)CH$_2$—HN), (A0348: cyano-CH$_2$CH(OMe)CH$_2$—
HN), (A0349: HO$_2$C—CH$_2$CH(OH)-MeN), (A0350: H$_2$NOC—CH$_2$CH(OH)-
MeN), (A0351: cyano-CH$_2$CH(OH)-MeN), (A0352: HO$_2$C—CH$_2$CH(OMe)-MeN),
(A0353: H$_2$NOC—CH$_2$CH(OMe)-MeN), (A0354: cyano-CH$_2$CH(OMe)-
MeN), (A0355: HO—CH$_2$CH(OH)CH$_2$-MeN), (A0356: MeO—CH$_2$CH(OH)CH$_2$-
MeN), (A0357: HO$_2$C—CH$_2$CH(OH)CH$_2$-MeN), (A0358: H$_2$NOC—CH$_2$CH(OH)CH$_2$-
MeN), (A0359: cyano-CH$_2$CH(OH)CH$_2$-MeN), (A0360: HO—CH$_2$CH(OMe)CH$_2$-
MeN), (A0361: MeO—CH$_2$CH(OMe)CH$_2$-MeN), (A0362: HO$_2$C—CH$_2$CH(OMe)CH$_2$-
MeN), (A0363: H$_2$NOC—CH$_2$CH(OMe)CH$_2$-MeN), (A0364: cyano-CH$_2$CH(OMe)CH$_2$-
MeN), (A0365: HO—(CH$_2$)$_2$—(HO(CH$_2$)$_2$)N), (A0366: MeO—(CH$_2$)$_2$—
(HO(CH$_2$)$_2$)N), (A0367: HO$_2$C—(CH$_2$)$_2$—(HO(CH$_2$)$_2$)N),
(A0368: H$_2$NOC—(CH$_2$)$_2$—(HO(CH$_2$)$_2$)N), (A0369: cyano-(CH$_2$)$_2$—
(HO(CH$_2$)$_2$)N), (A0370: HO—(CH$_2$)$_3$—(HO(CH$_2$)$_2$)N), (A0371: MeO—(CH$_2$)$_3$—
(HO(CH$_2$)$_2$)N), (A0372: HO$_2$C—(CH$_2$)$_3$—(HO(CH$_2$)$_2$)N), (A0373: H$_2$NOC—(CH$_2$)$_3$—
(HO(CH$_2$)$_2$)N), (A0374: cyano-(CH$_2$)$_3$—(HO(CH$_2$)$_2$)N), (A0375: HO—(CH$_2$)$_2$-
(MeO(CH$_2$)$_2$)N), (A0376: MeO—(CH$_2$)$_2$-(MeO(CH$_2$)$_2$)N), (A0377: HO$_2$C—(CH$_2$)$_2$-
(MeO(CH$_2$)$_2$)N), (A0378: H$_2$NOC—(CH$_2$)$_2$-(MeO(CH$_2$)$_2$)N), (A0379: cyano-(CH$_2$)$_2$-
(MeO(CH$_2$)$_2$)N), (A0380: HO—(CH$_2$)$_3$-(MeO(CH$_2$)$_2$)N), (A0381: MeO—(CH$_2$)$_3$-
(MeO(CH$_2$)$_2$)N), (A0382: HO$_2$C—(CH$_2$)$_3$-(MeO(CH$_2$)$_2$)N), (A0383: H$_2$NOC—(CH$_2$)$_3$-
(MeO(CH$_2$)$_2$)N), (A0384: cyano-(CH$_2$)$_3$-(MeO(CH$_2$)$_2$)N).

TABLE 24

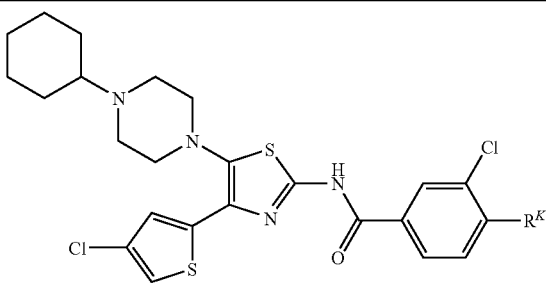

(No: R$^K$) =
(A0385: 3-HO-pyrr), (A0386: 3-MeO-pyrr), (A0387: 3-HO$_2$C-pyrr), (A0388: 3-H$_2$NOC-
pyrr), (A0389: 3-cyano-pyrr), (A0390: 3-MeHNOC-pyrr), (A0391: 3-Me$_2$NOC-
pyrr), (A0392: 3-F$_3$C-pyrr), (A0393: 3-F-pyrr), (A0394: 3-oxo-pyrr), (A0395: 3-H$_2$NO2S-
pyrr), (A0396: 3-HO$_3$S-pyrr), (A0397: 3-ttrz-pyrr), (A0398: 3-HOCH$_2$-pyrr), (A0399: 3-
MeOCH$_2$-pyrr), (A0400: 3-HO$_2$CCH$_2$-pyrr), (A0401: 3-H$_2$NOCCH$_2$-pyrr), (A0402: 3-
(cyano-CH$_2$)-pyrr), (A0403: 3-HO$_2$CCH$_2$O-pyrr), (A0404: 3-H$_2$NOCCH$_2$O-
pyrr), (A0405: 3-HO-pipe), (A0406: 3-MeO-pipe), (A0407: 3-HO$_2$C-pipe), (A0408: 3-
H$_2$NOC-pipe), (A0409: 3-cyano-pipe), (A0410: 3-MeHNOC-pipe), (A0411: 3-Me$_2$NOC-
pipe), (A0412: 3-F$_3$C-pipe), (A0413: 3-F-pipe), (A0414: 3-oxo-pipe), (A0415: 3-H$_2$NO$_2$S-
pipe), (A0416: 3-HO$_3$S-pipe), (A0417: 3-ttrz-pipe), (A0418: 3-HOCH$_2$-pipe), (A0419: 3-
MeOCH$_2$-pipe), (A0420: 3-HO$_2$CCH$_2$-pipe), (A0421: 3-H$_2$NOCCH$_2$-pipe), (A0422: 3-
(cyano-CH$_2$)-pipe), (A0423: 3-HO$_2$CCH$_2$O-pipe), (A0424: 3-H$_2$NOCCH$_2$O-
pipe), (A0425: 4-HO-pipe), (A0426: 4-MeO-pipe), (A0427: 4-HO$_2$C-pipe), (A0428: 4-
H$_2$NOC-pipe), (A0429: 4-cyano-pipe), (A0430: 4-MeHNOC-pipe), (A0431: 4-Me$_2$NOC-
pipe), (A0432: 4-F$_3$C-pipe), (A0433: 4-F-pipe), (A0434: 4-oxo-pipe), (A0435: 4-H$_2$NO$_2$S-

TABLE 24-continued

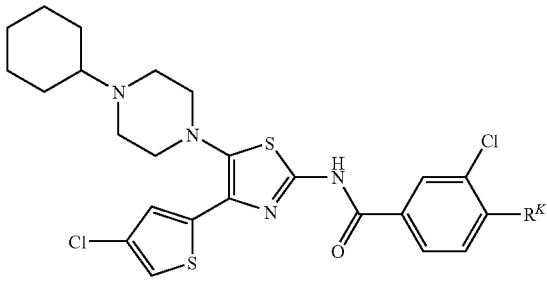

pipe), (A0436: 4-HO$_3$S-pipe), (A0437: 4-ttrz-pipe), (A0438: 4-HOCH$_2$-pipe), (A0439: 4-MeOCH$_2$-pipe), (A0440: 4-HO$_2$CCH$_2$-pipe), (A0441: 4-H$_2$NOCCH$_2$-pipe), (A0442: 4-(cyano-CH$_2$)-pipe), (A0443: 4-HO$_2$CCH$_2$O-pipe), (A0444: 4-H$_2$NOCCH$_2$O-pipe).

TABLE 25

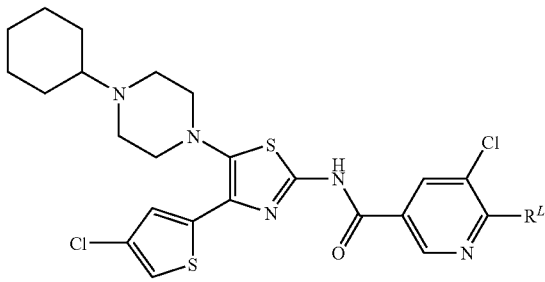

(NO: R$^L$) =
(A0445: HO—CH$_2$—O), (A0446: MeO—CH$_2$—O), (A0447: EtO$_2$C—CH$_2$—O), (A0448: HO$_2$C—CH$_2$—O), (A0449: H$_2$NOC—CH$_2$—O), (A0450: cyano-CH$_2$—O), (A0451: HO—(CH$_2$)$_2$—O), (A0452: MeO—(CH$_2$)$_2$—O), (A0453: EtO$_2$C—(CH$_2$)$_2$—O), (A0454: HO$_2$C—(CH$_2$)$_2$—O), (A0455: H$_2$NOC—(CH$_2$)$_2$—O), (A0456: cyano-(CH$_2$)$_2$—O), (A0457: HO—(CH$_2$)$_3$—O), (A0458: MeO—(CH$_2$)$_3$—O), (A0459: EtO$_2$C—(CH$_2$)$_3$—O), (A0460: HO$_2$C—(CH$_2$)$_3$—O), (A0461: H$_2$NOC—(CH$_2$)$_3$—O), (A0462: cyano-(CH$_2$)$_3$—O), (A0463: HO—CH$_2$—HN), (A0464: MeO—CH$_2$—HN), (A0465: EtO$_2$C—CH2—HN), (A0466: HO$_2$C—CH$_2$—HN), (A0467: H$_2$NOC—CH$_2$—HN), (A0468: cyano-CH$_2$—HN), (A0469: HO—(CH$_2$)$_2$—HN), (A0470: MeO—(CH$_2$)$_2$—HN), (A0471: EtO$_2$C—(CH$_2$)$_2$—HN), (A0472: HO$_2$C—(CH$_2$)$_2$—HN), (A0473: H$_2$NOC—(CH$_2$)$_2$—HN), (A0474: cyano-(CH$_2$)$_2$—HN), (A0475: HO—(CH$_2$)$_3$—HN), (A0476: MeO—(CH$_2$)$_3$—HN), (A0477: EtO$_2$C—(CH$_2$)$_3$—HN), (A0478: HO$_2$C—(CH$_2$)$_3$—HN), (A0479: H$_2$NOC—(CH$_2$)$_3$—HN), (A0480: cyano-(CH$_2$)$_3$—HN), (A0481: HO—CH$_2$-MeN), (A0482: MeO—CH$_2$-MeN), (A0483: EtO$_2$C—CH$_2$-MeN), (A0484: HO$_2$C—CH$_2$-MeN), (A0485: H$_2$NOC—CH$_2$-MeN), (A0486: cyano-CH$_2$-MeN), (A0487: HO—(CH$_2$)$_2$-MeN), (A0488: MeO—(CH$_2$)$_2$-MeN), (A0489: EtO$_2$C—(CH$_2$)$_2$-MeN), (A0490: HO$_2$C—(CH$_2$)$_2$-MeN), (A0491: H$_2$NOC—(CH$_2$)$_2$-MeN), (A0492: cyano-(CH$_2$)$_2$-MeN), (A0493: HO—(CH$_2$)$_3$-MeN), (A0494: MeO—(CH$_2$)$_3$-MeN), (A0495: EtO$_2$C—(CH$_2$)$_3$-MeN), (A0496: HO$_2$C—(CH$_2$)$_3$-MeN), (A0497: H$_2$NOC—(CH$_2$)$_3$-MeN), (A0498: cyano-(CH$_2$)$_3$-MeN).

TABLE 26

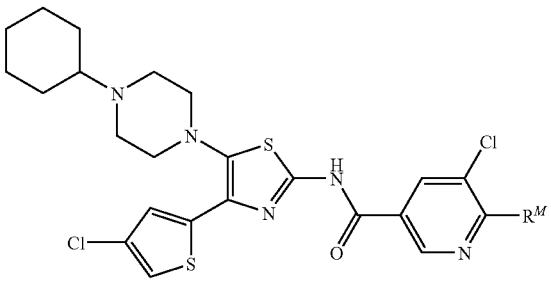

(No: R$^M$) =
(A0499: 2-HO$_2$C-azet), (A0500: 2-H$_2$NOC-azet), (A0501: 2-cyano-azet), (A0502: 2-MeHNOC-azet), (A0503: 2-Me$_2$NOC-azet), (A0504: 2-(MeO(CH$_2$)$_2$—(HNOC))-azet), (A0505: 2-(MeO(CH$_2$)$_3$—(HNOC))-azet), (A0506: 2-(mor-OC)-azet), (A0507: 2-

TABLE 26-continued

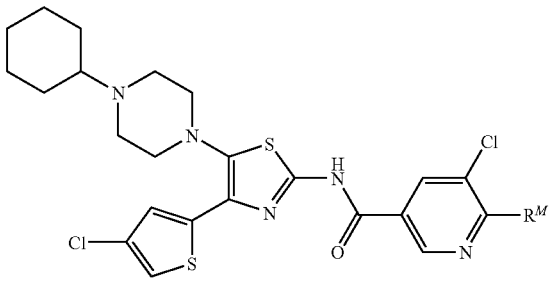

F$_3$C-azet), (A0508: 2-oxo-azet), (A0509: 2-H$_2$NO$_2$S-azet), (A0510: 2-HO$_3$S-azet), (A0511: 2-ttrz-azet), (A0512: 2-HOCH$_2$-azet), (A0513: 2-MeOCH$_2$-azet), (A0514: 2-HO$_2$CCH$_2$-azet), (A0515: 2-H$_2$NOCCH$_2$-azet), (A0516: 2-(cyano-CH$_2$)-azet), (A0517: 2-HO(CH$_2$)$_2$-azet), (A0518: 2-MeO(CH$_2$)$_2$-azet), (A0519: 2-HO$_2$C(CH$_2$)$_2$-azet), (A0520: 2-H$_2$NOC(CH$_2$)$_2$-azet), (A0521: 2-(cyano-(CH$_2$)$_2$)-azet), (A0522: 3-HO-azet), (A0523: 3-MeO-azet), (A0524: 3-HO2C-azet), (A0525: 3-H$_2$NOC-azet), (A0526: 3-cyano-azet), (A0527: 3-MeHNOC-azet), (A0528: 3-Me$_2$NOC-azet), (A0529: 3-(MeO(CH$_2$)$_2$—(HNOC))-azet), (A0530: 3-(MeO(CH$_2$)$_3$—(HNOC))-azet), (A0531: 3-(mor-OC)-azet), (A0532: 3-F$_3$C-azet), (A0533: 3-F-azet), (A0534: 3-oxo-azet), (A0535: 3-H$_2$NO$_2$S-azet), (A0536: 3-HO$_3$S-azet), (A0537: 3-ttrz-azet), (A0538: 3-HOCH$_2$-azet), (A0539: 3-MeOCH$_2$-azet), (A0540: 3-HO$_2$CCH$_2$-azet), (A0541: 3-H$_2$NOCCH$_2$-azet), (A0542: 3-(cyano-CH$_2$)-azet), (A0543: 3-HO(CH$_2$)$_2$-azet), (A0544: 3-MeO(CH$_2$)$_2$-azet), (A0545: 3-HO$_2$C(CH$_2$)$_2$-azet), (A0546: 3-H$_2$NOC(CH$_2$)$_2$-azet), (A0547: 3-(cyano-(CH$_2$)$_2$)-azet), (A0548: 3-HO$_2$CCH$_2$O-azet), (A0549: 3-H$_2$NOCCH$_2$O-azet), (A0550: 2-HO$_2$C-pyrr), (A0551: 2-H$_2$NOC-pyrr), (A0552: 2-cyano-pyrr), (A0553: 2-MeHNOC-pyrr), (A0554: 2-Me$_2$NOC-pyrr), (A0555: 2-(MeO(CH$_2$)$_2$—(HNOC))-pyrr), (A0556: 2-(MeO(CH$_2$)$_3$—(HNOC))-pyrr), (A0557: 2-(mor-OC)-pyrr), (A0558: 2-F$_3$C-pyrr), (A0559: 2-oxo-pyrr), (A0560: 2-H$_2$NO$_2$S-pyrr), (A0561: 2-HO$_3$S-pyrr), (A0562: 2-ttrz-pyrr), (A0563: 2-HOCH$_2$-pyrr), (A0564: 2-MeOCH$_2$-pyrr), (A0565: 2-HO$_2$CCH$_2$-pyrr), (A0566: 2-H$_2$NOCCH$_2$-pyrr), (A0567: 2-(cyano-CH$_2$)-pyrr), (A0568: 3-HO-pyrr), (A0569: 3-MeO-pyrr), (A0570: 3-HO$_2$C-pyrr), (A0571: 3-H$_2$NOC-pyrr), (A0572: 3-cyano-pyrr), (A0573: 3-MeHNOC-pyrr), (A0574: 3-Me$_2$NOC-pyrr), (A0575: 3-(MeO(CH$_2$)$_2$—(HNOC))-pyrr), (A0576: 3-(MeO(CH$_2$)$_3$—(HNOC))-pyrr), (A0577: 3-(mor-OC)-pyrr), (A0578: 3-F$_3$C-pyrr), (A0579: 3-F-pyrr), (A0580: 3-oxo-pyrr), (A0581: 3-H$_2$NO$_2$S-pyrr), (A0582: 3-HO$_3$S-pyrr), (A0583: 3-ttrz-pyrr), (A0584: 3-HOCH$_2$-pyrr), (A0585: 3-MeOCH$_2$-pyrr), (A0586: 3-HO$_2$CCH$_2$-pyrr), (A0587: 3-H$_2$NOCCH$_2$-pyrr), (A0588: 3-(cyano-CH$_2$)-pyrr), (A0589: 3-HO$_2$CCH$_2$O-pyrr), (A0590: 3-H$_2$NOCCH$_2$O-pyrr), (A0591: 2-HO$_2$C-pipe), (A0592: 2-H$_2$NOC-pipe), (A0593: 2-cyano-pipe), (A0594: 2-MeHNOC-pipe), (A0595: 2-Me$_2$NOC-pipe), (A0596: 2-(MeO(CH$_2$)$_2$—(HNOC))-pipe), (A0597: 2-(MeO(CH$_2$)$_3$—(HNOC))-pipe), (A0598: 2-(mor-OC)-pipe), (A0599: 2-F$_3$C-pipe), (A0600: 2-oxo-pipe), (A0601: 2-H$_2$NO$_2$S-pipe), (A0602: 2-HO$_3$S-pipe), (A0603: 2-ttrz-pipe), (A0604: 2-HOCH$_2$-pipe), (A0605: 2-MeOCH$_2$-pipe), (A0606: 2-HO$_2$CCH$_2$-pipe), (A0607: 2-H$_2$NOCCH$_2$-pipe), (A0608: 2-(cyano-CH$_2$)-pipe), (A0609: 2-HO(CH$_2$)$_2$-pipe), (A0610: 3-HO-pipe), (A0611: 3-MeO-pipe), (A0612: 3-HO$_2$C-pipe), (A0613: 3-H$_2$NOC-pipe), (A0614: 3-cyano-pipe), (A0615: 3-MeHNOC-pipe), (A0616: 3-Me$_2$NOC-pipe), (A0617: 3-(MeO(CH$_2$)$_2$—(HNOC))-pipe), (A0618: 3-(MeO(CH$_2$)$_3$—(HNOC))-pipe), (A0619: 3-(mor-OC)-pipe), (A0620: 3-F$_3$C-pipe), (A0621: 3-F-pipe), (A0622: 3-oxo-pipe), (A0623: 3-H$_2$NO$_2$S-pipe), (A0624: 3-HO$_3$S-pipe), (A0625: 3-ttrz-pipe), (A0626: 3-HOCH$_2$-pipe), (A0627: 3-MeOCH$_2$-pipe), (A0628: 3-HO$_2$CCH$_2$-pipe), (A0629: 3-H$_2$NOCCH$_2$-pipe), (A0630: 3-(cyano-CH$_2$)-pipe), (A0631: 3-HO$_2$CCH$_2$O-pipe), (A0632: 3-H$_2$NOCCH$_2$O-pipe), (A0633: 4-HO-pipe), (A0634: 4-MeO-pipe), (A0635: 4-HO$_2$C-pipe), (A0636: 4-H$_2$NOC-pipe), (A0637: 4-cyano-pipe), (A0638: 4-MeHNOC-pipe), (A0639: 4-Me$_2$NOC-pipe), (A0640: 4-(MeO(CH$_2$)$_2$—(HNOC))-pipe), (A0641: 4-(MeO(CH$_2$)$_3$—(HNOC))-pipe), (A0642: 4-(mor-OC)-pipe), (A0643: 4-F$_3$C-pipe), (A0644: 4-F-pipe), (A0645: 4-oxo-pipe), (A0646: 4-H$_2$NO$_2$S-pipe), (A0647: 4-HO$_3$S-pipe), (A0648: 4-ttrz-pipe), (A0649: 4-HOCH$_2$-pipe), (A0650: 4-MeOCH$_2$-pipe), (A0651: 4-HO$_2$CCH$_2$-pipe), (A0652: 4-H$_2$NOCCH$_2$-pipe), (A0653: 4-(cyano-CH$_2$)-pipe), (A0654: 4-HO$_2$CCH$_2$O-pipe), (A0655: 4-H$_2$NOCCH$_2$O-pipe), (A0656: 2-HO$_2$C-pipa), (A0657: 2-H$_2$NOC-pipa), (A0658: 2-cyano-pipa), (A0659: 2-MeHNOC-pipa), (A0660: 2-Me$_2$NOC-pipa), (A0661: 2-(MeO(CH$_2$)$_2$—(HNOC))-pipa), (A0662: 2-(MeO(CH$_2$)$_3$—(HNOC))-pipa), (A0663: 2-(mor-OC)-pipa), (A0664: 2-F$_3$C-pipa), (A0665: 2-oxo-pipa), (A0666: 2-H$_2$NO$_2$S-pipa), (A0667: 2-HO$_3$S-pipa), (A0668: 2-ttrz-pipa), (A0669: 2-HOCH$_2$-pipa), (A0670: 2-MeOCH$_2$-pipa), (A0671: 2-HO$_2$CCH$_2$-pipa), (A0672: 2-H$_2$NOCCH$_2$-pipa), (A0673: 2-(cyano-CH$_2$)-pipa), (A0674: 3-HO$_2$C-pipa), (A0675: 3-H$_2$NOC-pipa), (A0676: 3-cyano-pipa), (A0677: 3-MeHNOC-pipa), (A0678: 3-Me$_2$NOC-pipa), (A0679: 3-(MeO(CH$_2$)$_2$—(HNOC))-pipa), (A0680: 3-(MeO(CH$_2$)$_3$—(HNOC))-pipa), (A0681: 3-(mor-OC)-pipa), (A0682: 3-F$_3$C-pipa), (A0683: 3-oxo-pipa), (A0684: 3-H$_2$NO$_2$S-pipa), (A0685: 3-HO$_3$S-pipa), (A0686: 3-ttrz-pipa), (A0687: 3-HOCH$_2$-pipa), (A0688: 3-MeOCH$_2$-pipa), (A0689: 3-HO$_2$CCH$_2$-pipa), (A0690: 3-H$_2$NOCCH$_2$-pipa), (A0691: 3-(cyano-CH$_2$)-pipa), (A0692: 4-H$_2$NOC-pipa), (A0693: 4-MeHNOC-pipa), (A0694: 4-Me$_2$NOC-pipa), (A0695: 4-(MeO(CH$_2$)$_2$—(HNOC))-pipa), (A0696: 4-(MeO(CH$_2$)$_3$—(HNOC))-pipa), (A0697: 4-(mor-OC)-pipa), (A0698: 4-F$_3$C-pipa), (A0699: 4-H$_2$NO$_2$S-pipa), (A0700: 4-EtO$_2$C-pipa), (A0701: 4-HO$_2$CCH$_2$-pipa), (A0702: 4-H$_2$NOCCH$_2$-pipa), (A0703: 4-(cyano-CH$_2$)-pipa), (A0704: 2-HO$_2$C-

TABLE 26-continued

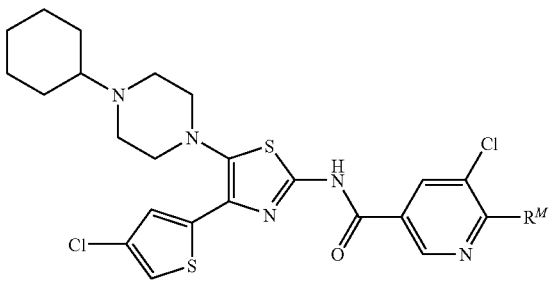

mor), (A0705: 2-H₂NOC-mor), (A0706: 2-cyano-mor), (A0707: 2-MeHNOC-mor), (A0708: 2-Me₂NOC-mor), (A0709: 2-(MeO(CH₂)₂—(HNOC))-mor), (A0710: 2-(MeO(CH₂)₃—(HNOC))-mor), (A0711: 2-(mor-OC)-mor), (A0712: 2-F₃C-mor), (A0713: 2-oxo-mor), (A0714: 2-H₂NO₂S-mor), (A0715: 2-HO₃S-mor), (A0716: 2-ttrz-mor), (A0717: 2-HOCH₂-mor), (A0718: 2-MeOCH₂-mor), (A0719: 2-HO₂CCH₂-mor), (A0720: 2-H₂NOCCH₂-mor), (A0721: 2-(cyano-CH₂)-mor), (A0722: 3-HO₂C-mor), (A0723: 3-H₂NOC-mor), (A0724: 3-cyano-mor), (A0725: 3-MeHNOC-mor), (A0726: 3-Me₂NOC-mor), (A0727: 3-(MeO(CH₂)₂—(HNOC))-mor), (A0728: 3-(MeO(CH₂)₃—(HNOC))-mor), (A0729: 3-(mor-OC)-mor), (A0730: 3-F₃C-mor), (A0731: 3-oxo-mor), (A0732: 3-H₂NO₂S-mor), (A0733: 3-HO₃S-mor), (A0734: 3-ttrz-mor), (A0735: 3-HOCH₂-mor), (A0736: 3-MeOCH₂-mor), (A0737: 3-HO₂CCH₂-mor), (A0738: 3-H₂NOCCH₂-mor), (A0739: 3-(cyano-CH₂)-mor), (A0740: 2-HO₂C-tmor), (A0741: 2-H₂NOC-tmor), (A0742: 2-cyano-tmor), (A0743: 2-MeHNOC-tmor), (A0744: 2-Me₂NOC-tmor), (A0745: 2-(MeO(CH₂)₂—(HNOC))-tmor), (A0746: 2-(MeO(CH₂)₃—(HNOC))-tmor), (A0747: 2-(mor-OC)-tmor), (A0748: 2-F₃C-tmor), (A0749: 2-oxo-tmor), (A0750: 2-H₂NO₂S-tmor), (A0751: 2-HO₃S-tmor), (A0752: 2-ttrz-tmor), (A0753: 2-HOCH₂-tmor), (A0754: 2-MeOCH₂-tmor), (A0755: 2-HO₂CCH₂-tmor), (A0756: 2-H₂NOCCH₂-tmor), (A0757: 2-(cyano-CH₂)-tmor), (A0758: 3-HO₂C-tmor), (A0759: 3-H₂NOC-tmor), (A0760: 3-cyano-tmor), (A0761: 3-MeHNOC-tmor), (A0762: 3-Me₂NOC-tmor), (A0763: 3-(MeO(CH₂)₂—(HNOC))-tmor), (A0764: 3-(MeO(CH₂)₃—(HNOC))-tmor), (A0765: 3-(mor-OC)-tmor), (A0766: 3-F₃C-tmor), (A0767: 3-oxo-tmor), (A0768: 3-H₂NO₂S-tmor), (A0769: 3-HO₃S-tmor), (A0770: 3-ttrz-tmor), (A0771: 3-HOCH₂-tmor), (A0772: 3-MeOCH₂-tmor), (A0773: 3-HO₂CCH₂-tmor), (A0774: 3-H₂NOCCH₂-tmor), (A0775 3-(cyano-CH₂)-tmor), (A0776: 1-oxido-tmor), (A0777: 1,1-dioxido-tmor), (A0778: 4-HO-cHex), (A0779: 4-MeO-cHex), (A0780: 4-HO₂C-cHex), (A0781: 4-H₂NOC-cHex), (A0782: 4-cyano-cHex), (A0783: 4-MeHNOC-cHex), (A0784: 4-Me₂NOC-cHex), (A0785: 4-(MeO(CH₂)₂—(HNOC))-cHex), (A0786: 4-(MeO(CH₂)₃—(HNOC))-cHex), (A0787: 4-(mor-OC)-cHex), (A0788: 4-F₃C-cHex), (A0789: 4-F-cHex), (A0790: 4-oxo-cHex), (A0791: 4-H₂NO₂S-cHex), (A0792: 4-HO₃S-cHex), (A0793: 4-ttrz-cHex), (A0794: 4-HOCH₂-cHex), (A0795: 4-MeOCH₂-cHex), (A0796: 4-HO₂CCH₂-cHex), (A0797: 4-H₂NOCCH₂-cHex), (A0798: 4-(cyano-CH₂)-cHex), (A0799: 4-HO₂CCH₂O-cHex), (A0800: 4-H₂NOCCH₂O-cHex), (A0801: 1-H₂NOC-piperidin-4-yl), (A0802: 1-MeHNOC-piperidin-4-yl), (A0803: 1-Me₂NOC-piperidin-4-yl), (A0804: 1-(MeO(CH₂)₂—(HNOC))-piperidin-4-yl), (A0805: 1-(MeO(CH₂)₃—(HNOC))-piperidin-4-yl), (A0806: 1-(mor-OC)-piperidin-4-yl), (A0807: 1-F₃C-piperidin-4-yl), (A0808: 1-H₂NO₂S-piperidin-4-yl), (A0809: 1-EtO₂C-piperidin-4-yl), (A0810: 1-HO₂CCH₂-piperidin-4-yl), (A0811: 1-H₂NOCCH₂-piperidin-4-yl), (A0812: 1-(cyano-CH₂)-piperidin-4-yl), (A0813: 2-HO₂C-4-HO-pipe), (A0814: 2-H₂NOC-4-HO-pipe), (A0815: 2-cyano-4-HO-pipe), (A0816: 2-HOCH₂-4-HO-pipe), (A0817: 3-HO-4-HO-pipe), (A0818: 3-MeO-4-HO-pipe), (A0819: 3-HO₂C-4-HO-pipe), (A0820: 3-H₂NOC-4-HO-pipe), (A0821: 3-cyano-4-HO-pipe), (A0822: 3-HOCH₂-4-HO-pipe), (A0823: 4-HO-4-HO-pipe), (A0824: 4-MeO-4-HO-pipe), (A0825: 4-HO₂C-4-HO-pipe), (A0826: 4-H₂NOC-4-HO-pipe), (A0827: 4-cyano-4-HO-pipe), (A0828: 2-HO₂C-4-MeO-pipe), (A0829: 2-H₂NOC-4-MeO-pipe), (A0830: 2-cyano-4-MeO-pipe), (A0831: 2-HOCH₂-4-MeO-pipe), (A0832: 3-HO-4-MeO-pipe), (A0833: 3-MeO-4-MeO-pipe), (A0834: 3-HO₂C-4-MeO-pipe), (A0835: 3-H₂NOC-4-MeO-pipe), (A0836: 3-cyano-4-MeO-pipe), (A0837: 3-HOCH₂-4-MeO-pipe), (A0838: 4-HO-4-MeO-pipe), (A0839: 4-MeO-4-MeO-pipe), (A0840: 4-HO₂C-4-MeO-pipe), (A0841: 4-H₂NOC-4-MeO-pipe), (A0842: 4-cyano-4-MeO-pipe), (A0843: 2-HO₂C-4-HO₂C-pipe), (A0844: 2-H₂NOC-4-HO₂C-pipe), (A0845: 2-cyano-4-HO₂C-pipe), (A0846: 2-HOCH₂-4-HO₂C-pipe), (A0847: 3-HO-4-HO₂C-pipe), (A0848: 3-MeO-4-HO₂C-pipe), (A0849: 3-HO₂C-4-HO₂C-pipe), (A0850: 3-H₂NOC-4-HO₂C-pipe), (A0851: 3-cyano-4-HO₂C-pipe), (A0852: 3-HOCH₂-4-HO₂C-pipe), (A0853: 4-HO-4-HO₂C-pipe), (A0854: 4-MeO-4-HO₂C-pipe), (A0855: 4-HO₂C-4-HO₂C-pipe), (A0856: 4-H₂NOC-4-HO₂C-pipe), (A0857: 4-cyano-4-HO₂C-pipe), (A0858: 2-HO₂C-4-H₂NOC-pipe), (A0859: 2-H₂NOC-4-H₂NOC-pipe), (A0860: 2-cyano-4-H₂NOC-pipe), (A0861: 2-HOCH₂-4-H₂NOC-pipe), (A0862: 3-HO-4-H₂NOC-pipe), (A0863: 3-MeO-4-H₂NOC-pipe), (A0864: 3-HO₂C-4-H₂NOC-pipe), (A0865: 3-H₂NOC-4-H₂NOC-pipe), (A0866: 3-cyano-4-H₂NOC-pipe), (A0867: 3-HOCH₂-4-H₂NOC-pipe), (A0868: 4-HO-4-H₂NOC-pipe), (A0869: 4-MeO-4-H₂NOC-pipe), (A0870: 4-HO₂C-4-H₂NOC-pipe), (A0871: 4-H₂NOC-4-H₂NOC-pipe), (A0872: 4-cyano-4-H₂NOC-pipe), (A0873: 2-HO₂C-4-cyano-pipe), (A0874: 2-H₂NOC-4-cyano-pipe), (A0875: 2-cyano-4-cyano-pipe), (A0876: 2-HOCH₂-4-cyano-pipe), (A0877: 3-HO-4-cyano-pipe), (A0878: 3-MeO-4-cyano-pipe), (A0879: 3-HO₂C-4-cyano-pipe), (A0880: 3-H₂NOC-4-cyano-pipe), (A0881: 3-cyano-4-cyano-pipe), (A0882: 3-HOCH₂-4-cyano-pipe), (A0883: 4-HO-4-cyano- TABLE 26-continued

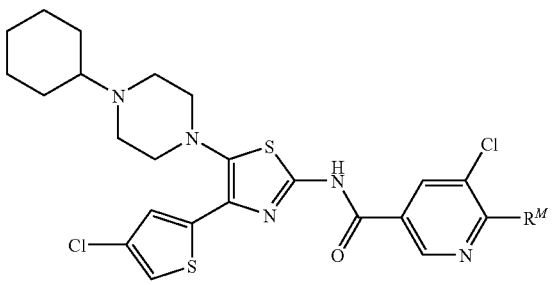

pipe), (A0884: 4-MeO-4-cyano-pipe), (A0885: 4-HO₂C-4-cyano-pipe), (A0886: 4-H₂NOC-4-cyano-pipe), (A0887: 4-cyano-4-cyano-pipe), (A0888: 2-HO₂C-4-(HOCH₂)-pipe), (A0889: 2-H₂NOC-4-(HOCH₂)-pipe), (A0890: 2-cyano-4-(HOCH₂)-pipe), (A0891: 2-HOCH₂-4-(HOCH₂)-pipe), (A0892: 3-HO-4-(HOCH₂)-pipe), (A0893: 3-MeO-4-(HOCH₂)-pipe), (A0894: 3-HO₂C-4-(HOCH₂)-pipe), (A0895: 3-H₂NOC-4-(HOCH₂)-pipe), (A0896: 3-cyano-4-(HOCH₂)-pipe), (A0897: 3-HOCH₂-4-(HOCH₂)-pipe), (A0898: 4-HO-4-(HOCH₂)-pipe), (A0899: 4-MeO-4-(HOCH₂)-pipe), (A0900: 4-HO₂C-4-(HOCH₂)-pipe), (A0901: 4-H₂NOC-4-(HOCH₂)-pipe), (A0902: 4-cyano-4-(HOCH₂)-pipe), (A0903: 2-HO₂C-4-HO-pyrr), (A0904: 2-H₂NOC-4-HO-pyrr), (A0905: 2-cyano-4-HO-pyrr), (A0906: 2-HOCH₂-4-HO-pyrr), (A0907: 3-HO-4-HO-pyrr), (A0908: 3-MeO-4-HO-pyrr), (A0909: 3-HO₂C-4-HO-pyrr), (A0910: 3-H₂NOC-4-HO-pyrr), (A0911: 3-cyano-4-HO-pyrr), (A0912: 3-HOCH₂-4-HO-pyrr), (A0913: 2-HO₂C-4-MeO-pyrr), (A0914: 2-H₂NOC-4-MeO-pyrr),
(A0915: 2-cyano-4-MeO-pyrr), (A0916: 2-HOCH₂-4-MeO-pyrr), (A0917: 3-HO-4-MeO-pyrr), (A0918: 3-MeO-4-MeO-pyrr), (A0919: 3-HO₂C-4-MeO-pyrr), (A0920: 3-H₂NOC-4-MeO-pyrr), (A0921: 3-cyano-4-MeO-pyrr), (A0922: 3-HOCH₂-4-MeO-pyrr), (A0923: 2-HO₂C-4-HO₂C-pyrr), (A0924: 2-H₂NOC-4-HO₂C-pyrr), (A0925: 2-cyano-4-HO₂C-pyrr), (A0926: 2-HOCH₂-4-HO₂C-pyrr), (A0927: 3-HO-4-HO₂C-pyrr), (A0928: 3-MeO-4-HO₂C-pyrr), (A0929: 3-HO₂C-4-HO₂C-pyrr), (A0930: 3-H₂NOC-4-HO₂C-pyrr), (A0931: 3-cyano-4-HO₂C-pyrr), (A0932: 3-HOCH₂-4-HO2C-pyrr), (A0933: 2-HO₂C-4-H₂NOC-pyrr), (A0934: 2-H₂NOC-4-H₂NOC-pyrr), (A0935: 2-cyano-4-H₂NOC-pyrr), (A0936: 2-HOCH₂-4-H₂NOC-pyrr), (A0937: 3-HO-4-H₂NOC-pyrr), (A0938: 3-MeO-4-H₂NOC-pyrr), (A0939: 3-HO₂C-4-H₂NOC-pyrr), (A0940: 3-H₂NOC-4-H₂NOC-pyrr), (A0941: 3-cyano-4-H₂NOC-pyrr), (A0942: 3-HOCH₂-4-H₂NOC-pyrr), (A0943: 2-HO₂C-4-cyano-pyrr), (A0944: 2-H₂NOC-4-cyano-pyrr), (A0945: 2-cyano-4-cyano-pyrr), (A0946: 2-HOCH₂-4-cyano-pyrr), (A0947: 3-HO-4-cyano-pyrr), (A0948: 3-MeO-4-cyano-pyrr), (A0949: 3-HO₂C-4-cyano-pyrr), (A0950: 3-H₂NOC-4-cyano-pyrr), (A0951: 3-cyano-4-cyano-pyrr), (A0952: 3-HOCH₂-4-cyano-pyrr), (A0953: 2-HO₂C-4-(HOCH₂)-pyrr), (A0954: 2-H₂NOC-4-(HOCH₂)-pyrr), (A0955: 2-cyano-4-(HOCH₂)-pyrr), (A0956: 2-HOCH₂-4-(HOCH₂)-pyrr), (A0957: 3-HO-4-(HOCH₂)-pyrr), (A0958: 3-MeO-4-(HOCH₂)-pyrr), (A0959: 3-HO₂C-4-(HOCH₂)-pyrr), (A0960: 3-H₂NOC-4-(HOCH₂)-pyrr), (A0961: 3-cyano-4-(HOCH₂)-pyrr), (A0962: 3-HOCH₂-4-(HOCH₂)-pyrr), (A0963: 2-HO₂C-3-HO-pyrr), (A0964: 2-H₂NOC-3-HO-pyrr), (A0965: 2-cyano-3-HO-pyrr), (A0966: 2-HOCH₂-3-HO-pyrr), (A0967: 3-HO-3-HO-pyrr), (A0968: 3-MeO-3-HO-pyrr), (A0969: 3-HO₂C-3-HO-pyrr), (A0970: 3-H₂NOC-3-HO-pyrr), (A0971: 3-cyano-3-HO-pyrr), (A0972: 2-HO₂C-3-MeO-pyrr), (A0973: 2-H₂NOC-3-MeO-pyrr), (A0974: 2-cyano-3-MeO-pyrr), (A0975: 2-HOCH₂-3-MeO-pyrr), (A0976: 3-HO-3-MeO-pyrr), (A0977: 3-MeO-3-MeO-pyrr), (A0978: 3-HO₂C-3-MeO-pyrr), (A0979: 3-H₂NOC-3-MeO-pyrr), (A0980: 3-cyano-3-MeO-pyrr), (A0981: 2-HO₂C-3-HO₂C-pyrr), (A0982: 2-H₂NOC-3-HO₂C-pyrr), (A0983: 2-cyano-3-HO₂C-pyrr), (A0984: 2-HOCH₂-3-HO₂C-pyrr), (A0985: 3-HO-3-HO₂C-pyrr), (A0986: 3-MeO-3-HO₂C-pyrr), (A0987: 3-HO₂C-3-HO₂C-pyrr), (A0988: 3-H₂NOC-3-HO₂C-pyrr), (A0989: 3-cyano-3-HO₂C-pyrr), (A0990: 2-HO₂C-3-H₂NOC-pyrr), (A0991: 2-H₂NOC-3-H₂NOC-pyrr), (A0992: 2-cyano-3-H₂NOC-pyrr), (A0993: 2-HOCH₂-3-H₂NOC-pyrr), (A0994: 3-HO-3-H₂NOC-pyrr), (A0995: 3-MeO-3-H₂NOC-pyrr), (A0996: 3-HO₂C-3-H₂NOC-pyrr), (A0997: 3-H₂NOC-3-H₂NOC-pyrr), (A0998: 3-cyano-3-H₂NOC-pyrr), (A0999: 2-HO₂C-3-cyano-pyrr), (A1000: 2-H₂NOC-3-cyano-pyrr), (A1001: 2-cyano-3-cyano-pyrr), (A1002: 2-HOCH₂-3-cyano-pyrr), (A1003: 3-HO-3-cyano-pyrr), (A1004: 3-MeO-3-cyano-pyrr), (A1005: 3-HO₂C-3-cyano-pyrr), (A1006: 3-H₂NOC-3-cyano-pyrr), (A1007: 3-cyano-3-cyano-pyrr),
(A1008: 2-HO₂C-3-(HOCH₂)-pyrr), (A1009: 2-H₂NOC-3-(HOCH₂)-pyrr), (A1010: 2-cyano-3-(HOCH₂)-pyrr), (A1011: 2-HOCH₂-3-(HOCH₂)-pyrr),
(A1012: 3-HO-3-(HOCH₂)-pyrr), (A1013: 3-MeO-3-(HOCH₂)-pyrr), (A1014: 3-HO₂C-3-(HOCH₂)-pyrr), (A1015: 3-H₂NOC-3-(HOCH₂)-pyrr), (A1016: 3-cyano-3-(HOCH₂)-pyrr), (A1017: 8-azaspiro[4.5]dec-8-yl), (A1018: 1-oxa-8-azaspiro[4.5]dec-8-yl), (A1019: 2'-oxo-(piperidine-4-spiro-3'-pyrrolidine)-1-yl), (A1020: 1'-methyl-2'-oxo-(piperidine-4-spiro-3'-pyrrolidine)-1-yl), (A1021: 1-phenyl-4-oxo-1,3,8-triazaspiro-[4.5]dec-8-yl), (A1022: (piperidine-4-spiro-5'-hydantoin)-1-yl), (A1023: (1,3-dihydroisobenzofuran-1-spiro-4'-piperidin)-1'-yl), (A1024: 3-oxo-(1,3-dihydroisobenzofuran-1-spiro-4'-piperidin)-1'-yl).

TABLE 27

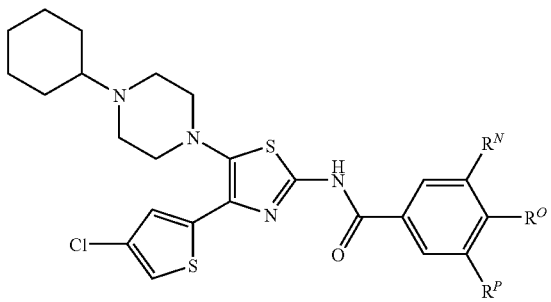

(No: $R^N$, $R^O$, $R^P$) =
(A1025: H, HO, H), (A1026: H, HO—(CH$_2$)$_2$—O, H), (A1027: H, HO—(CH$_2$)$_3$—
O, H), (A1028: H, 4-HO-pipe, H), (A1029: H, 3-HO-pyrr, H), (A1030: H, 4-HO$_2$C-
pipe, H), (A1031: H, 4-(cyano)-pipe, H), (A1032: H, 4-Ac-pipa, H), (A1033: H, 3-oxo-
pipa, H), (A1034: F, HO, H), (A1035: F, HO—(CH$_2$)$_2$—O, H), (A1036: F, HO—(CH$_2$)$_3$—
O, H), (A1037: F, 4-HO-pipe, H), (A1038: F, 3-HO-pyrr, H), (A1039: F, 4-HO$_2$C-
pipe, H), (A1040: F, 4-(cyano)-pipe, H), (A1041: F, 4-Ac-pipa, H), (A1042: F, 3-oxo-
pipa, H), (A1043: F, HO, F), (A1044: F, HO—(CH$_2$)$_2$—O, F), (A1045: F, HO—(CH$_2$)$_3$—
O, F), (A1046: F, 4-HO-pipe, F), (A1047: F, 3-HO-pyrr, F), (A1048: F, 4-HO$_2$C-
pipe, F), (A1049: F, 4-(cyano)-pipe, F), (A1050: F, 4-Ac-pipa, F), (A1051: F, 3-oxo-
pipa, F), (A1052: F, HO, Cl), (A1053: F, HO—(CH$_2$)$_2$—O, Cl), (A1054: F, HO—(CH$_2$)$_3$—
O, Cl), (A1055: F, 4-HO-pipe, Cl), (A1056: F, 3-HO-pyrr, Cl), (A1057: F, 4-HO$_2$C-
pipe, Cl), (A1058: F, 4-(cyano)-pipe, Cl), (A1059: F, 4-Ac-pipa, Cl), (A1060: F, 3-oxo-
pipa, Cl), (A1061: F, HO, Br), (A1062: F, HO—(CH$_2$)$_2$—O, Br), (A1063: F, HO—(CH$_2$)$_3$—
O, Br), (A1064: F, 4-HO-pipe, Br), (A1065: F, 3-HO-pyrr, Br), (A1066: F, 4-HO$_2$C-
pipe, Br), (A1067: F, 4-(cyano)-pipe, Br), (A1068: F, 4-Ac-pipa, Br), (A1069: F, 3-oxo-
pipa, Br), (A1070: F, HO, Me), (A1071: F, HO—(CH$_2$)$_2$—O, Me), (A1072: F, HO—(CH$_2$)$_3$—
O, Me), (A1073: F, 4-HO-pipe, Me), (A1074: F, 3-HO-pyrr, Me), (A1075: F, 4-HO$_2$C-
pipe, Me), (A1076: F, 4-(cyano)-pipe, Me), (A1077: F, 4-Ac-pipa, Me), (A1078: F, 3-oxo-
pipa, Me), (A1079: F, HO, HO), (A1080: F, HO—(CH$_2$)$_2$—O, HO), (A1081: F, HO—(CH$_2$)$_3$—
O, HO), (A1082: F, 4-HO-pipe, HO), (A1083: F, 3-HO-pyrr, HO),
(A1084: F, 4-HO$_2$C-pipe, HO), (A1085: F, 4-(cyano)-pipe, HO), (A1086: F, 4-Ac-
pipa, HO), (A1087: F, 3-oxo-pipa, HO), (A1088: F, HO, MeO), (A1089: F, HO—(CH$_2$)$_2$—
O, MeO), (A1090: F, HO—(CH$_2$)$_3$—O, MeO), (A1091: F, 4-HO-pipe, MeO), (A1092: F, 3-HO-
pyrr, MeO), (A1093: F, 4-HO$_2$C-pipe, MeO), (A1094: F, 4-(cyano)-
pipe, MeO), (A1095: F, 4-Ac-pipa, MeO), (A1096: F, 3-oxo-
pipa, MeO), (A1097: Cl, HO, Cl), (A1098: Cl, HO—(CH$_2$)$_2$—O, Cl), (A1099: Cl, HO—(CH$_2$)$_3$—
O, Cl), (A1100: Cl, 4-HO-pipe, Cl), (A1101: Cl, 3-HO-pyrr-Cl), (A1102: Cl, 4-HO$_2$C-
pipe, Cl), (A1103: Cl, 4-(cyano)-pipe, Cl), (A1104: Cl, 4-Ac-pipa, Cl), (A1105: Cl, 3-oxo-
pipa, Cl), (A1106: Cl, HO, Br), (A1107: Cl, HO—(CH$_2$)$_2$—O, Br), (A1108: Cl, HO—(CH$_2$)$_3$—
O, Br), (A1109: Cl, 4-HO-pipe, Br), (A1110: Cl, 3-HO-pyrr, Br), (A1111: Cl, 4-HO$_2$C-
pipe, Br), (A1112: Cl, 4-(cyano)-pipe, Br), (A1113: Cl, 4-Ac-pipa, Br), (A1114: Cl, 3-oxo-
pipa, Br), (A1115: Cl, HO, Me), (A1116: Cl, HO—(CH$_2$)$_2$—O, Me), (A1117: Cl, HO—(CH$_2$)$_3$—
O, Me), (A1118: Cl, 4-HO-pipe, Me), (A1119: Cl, 3-HO-pyrr, Me), (A1120: Cl, 4-HO$_2$C-
pipe, Me), (A1121: Cl, 4-(cyano)-pipe, Me), (A1122: Cl, 4-Ac-pipa, Me), (A1123: Cl, 3-oxo-
pipa, Me), (A1124: Cl, HO, HO), (A1125: Cl, HO—(CH$_2$)$_2$—O, HO), (A1126: Cl, HO—(CH$_2$)$_3$—
O, HO), (A1127: Cl, 4-HO-pipe, HO), (A1128: Cl, 3-HO-pyrr, HO), (A1129: Cl, 4-HO$_2$C-
pipe, HO), (A1130: Cl, 4-(cyano)-pipe, HO), (A1131: Cl, 4-Ac-pipa, HO), (A1132: Cl, 3-oxo-
pipa, HO), (A1133: Cl, HO, MeO), (A1134: Cl, HO—(CH$_2$)$_2$—O, MeO), (A1135: Cl, HO—(CH$_2$)$_3$—
O, MeO), (A1136: Cl, 4-HO-pipe, MeO), (A1137: Cl, 3-HO-pyrr, MeO), (A1138: Cl, 4-
HO$_2$C-pipe, MeO), (A1139: Cl, 4-(cyano)-pipe, MeO), (A1140: Cl, 4-Ac-
pipa, MeO), (A1141: Cl, 3-oxo-pipa, MeO), (A1142: Br, HO, H), (A1143: Br, HO—(CH$_2$)$_2$—
O, H), (A1144: Br, HO—(CH$_2$)$_3$—O, H), (A1145: Br, 4-HO-pipe, H), (A1146: Br, 3-HO-
pyrr, H), (A1147: Br, 4-HO$_2$C-pipe, H), (A1148: Br, 4-(cyano)-pipe, H), (A1149: Br, 4-Ac-
pipa, H), (A1150: Br, 3-oxo-pipa, H), (A1151: Me, HO, H), (A1152: Me, HO—(CH$_2$)$_2$—
O, H), (A1153: Me, HO—(CH$_2$)$_3$—O, H), (A1154: Me, 4-HO-pipe, H), (A1155: Me, 3-HO-
pyrr, H), (A1156: Me, 4-HO$_2$C-pipe, H), (A1157: Me, 4-(cyano)-pipe, H), (A1158: Me, 4-Ac-
pipa, H), (A1159: Me, 3-oxo-pipa, H), (A1160: HO, HO, H), (A1161: HO, HO—(CH$_2$)$_2$—
O, H), (A1162: HO, HO—(CH$_2$)$_3$—O, H), (A1163: HO, 4-HO-pipe, H), (A1164: HO, 3-HO-
pyrr, H), (A1165: HO, 4-HO$_2$C-pipe, H), (A1166: HO, 4-(cyano)-pipe, H), (A1167: HO, 4-
Ac-pipa, H), (A1168: HO, 3-oxo-pipa, H), (A1169: MeO, HO, H), (A1170: MeO, HO—(CH$_2$)$_2$—
O, H), (A1171: MeO, HO—(CH$_2$)$_3$—O, H), (A1172: MeO, 4-HO-pipe, H), (A1173: MeO, 3-HO-
pyrr, H), (A1174: MeO, 4-HO$_2$C-pipe, H), (A1175: MeO, 4-(cyano)-
pipe, H), (A1176: MeO, 4-Ac-pipa, H), (A1177: MeO, 3-oxo-
pipa, H), (A1178: H, H, HO), (A1179: H, H, HO—(CH$_2$)$_2$—O), (A1180: H, H, HO—(CH$_2$)$_3$—
O), (A1181: H, H, 4-HO-pipe), (A1182: H, H, 3-HO-pyrr), (A1183: H, H, 4-HO$_2$C-
pipe), (A1184: H, H, 4-(cyano)-pipe), (A1185: H, H, 4-Ac-pipa), (A1186: H, H, 3-oxo-
pipa), (A1187: F, H, HO), (A1188: F, H, HO—(CH$_2$)$_2$—O), (A1189: F, H, HO—(CH$_2$)$_3$—
O), (A1190: F, H, 4-HO-pipe), (A1191: F, H, 3-HO-pyrr), (A1192: F, H, 4-HO$_2$C-
pipe), (A1193: F, H, 4-(cyano)-pipe), (A1194: F, H, 4-Ac-pipa),
(A1195: F, H, 3-oxo-pipa), (A1196: Cl, H, HO), (A1197: Cl, H, HO—(CH$_2$)$_2$—
O), (A1198: Cl, H, HO—(CH$_2$)$_3$—O), (A1199: Cl, H, 4-HO-pipe), (A1200: Cl, H, 3-HO-
pyrr), (A1201: Cl, H, 4-HO$_2$C-pipe), (A1202: Cl, H, 4-(cyano)-pipe), (A1203: Cl, H, 4-Ac-
pipa), (A1204: Cl, H, 3-oxo-pipa), (A1205: Br, H, HO), (A1206: Br, H, HO—(CH$_2$)$_2$—
O), (A1207: Br, H, HO—(CH$_2$)$_3$—O), (A1208: Br, H, 4-HO-pipe), (A1209: Br, H, 3-HO- TABLE 27-continued

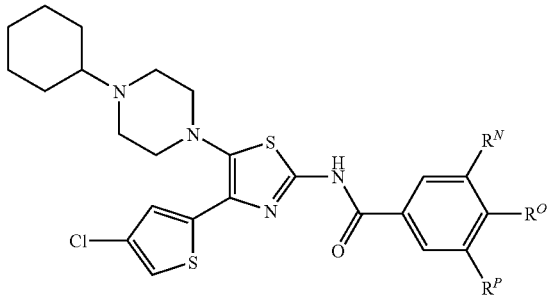

pyrr), (A1210: Br, H, 4-HO$_2$C-pipe), (A1211: Br, H, 4-(cyano)-pipe), (A1212: Br, H, 4-Ac-pipa), (A1213: Br, H, 3-oxo-pipa), (A1214: Me, H, HO), (A1215: Me, H, HO—(CH$_2$)$_2$—O), (A1216: Me, H, HO—(CH$_2$)$_3$—O), (A1217: Me, H, 4-HO-pipe), (A1218: Me, H, 3-HO-pyrr), (A1219: Me, H, 4-HO$_2$C-pipe), (A1220: Me, H, 4-(cyano)-pipe), (A1221: Me, H, 4-Ac-pipa), (A1222: Me, H, 3-oxo-pipa), (A1223: HO, H, HO), (A1224: HO, H, HO—(CH$_2$)$_2$—O), (A1225: HO, H, HO—(CH$_2$)$_3$—O), (A1226: HO, H, 4-HO-pipe), (A1227: HO, H, 3-HO-pyrr), (A1228: HO, H, 4-HO$_2$C-pipe), (A1229: HO, H, 4-(cyano)-pipe), (A1230: HO, H, 4-Ac-pipa), (A1231: HO, H, 3-oxo-pipa), (A1232: MeO, H, HO), (A1233: MeO, H, HO—(CH$_2$)$_2$—O), (A1234: MeO, H, HO—(CH$_2$)$_3$—O), (A1235: MeO, H, 4-HO-pipe), (A1236: MeO, H, 3-HO-pyrr), (A1237: MeO, H, 4-HO$_2$C-pipe), (A1238: MeO, H, 4-(cyano)-pipe), (A1239: MeO, H, 4-Ac-pipa), (A1240: MeO, H, 3-oxo-pipa).

TABLE 28

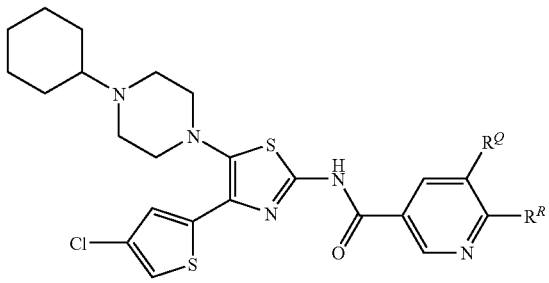

(No: R$^Q$, R$^R$) =
(A1241: H, HO), (A1242: H, HO—(CH$_2$)$_2$—O), (A1243: H, HO—(CH$_2$)$_3$—O), (A1244: H, 4-HO-pipe), (A1245: H, 3-HO-pyrr), (A1246: H, 4-HO$_2$C-pipe), (A1247: H, 4-(cyano)-pipe), (A1248: H, 4-Ac-pipa), (A1249: H, 3-oxo-pipa), (A1250: F, HO), (A1251: F, HO—(CH$_2$)$_2$—O), (A1252: F, HO—(CH$_2$)$_3$—O), (A1253: F, 4-HO-pipe), (A1254: F, 3-HO-pyrr), (A1255: F, 4-HO$_2$C-pipe), (A1256: F, 4-(cyano)-pipe), (A1257: F, 4-Ac-pipa), (A1258: F, 3-oxo-pipa), (A1259: Br, HO), (A1260: Br, HO—(CH$_2$)$_2$—O), (A1261: Br, HO—(CH$_2$)$_3$—O), (A1262: Br, 4-HO-pipe), (A1263: Br, 3-HO-pyrr), (A1264: Br, 4-HO$_2$C-pipe), (A1265: Br, 4-(cyano)-pipe), (A1266: Br, 4-Ac-pipa), (A1267: Br, 3-oxo-pipa), (A1268: Me, HO), (A1269: Me, HO—(CH$_2$)$_2$—O), (A1270: Me, HO—(CH$_2$)$_3$—O), (A1271: Me, 4-HO-pipe), (A1272: Me, 3-HO-pyrr), (A1273: Me, 4-HO$_2$C-pipe), (A1274: Me, 4-(cyano)-pipe), (A1275: Me, 4-Ac-pipa), (A1276: Me, 3-oxo-pipa), (A1277: HO, HO), (A1278: HO, HO—(CH$_2$)$_2$—O), (A1279: HO, HO—(CH$_2$)$_3$—O), (A1280: HO, 4-HO-pipe), (A1281: HO, 3-HO-pyrr),
(A1282: HO, 4-HO$_2$C-pipe), (A1283: HO, 4-(cyano)-pipe), (A1284: HO, 4-Ac-pipa), (A1285: HO, 3-oxo-pipa), (A1286: MeO, HO), (A1287: MeO, HO—(CH$_2$)$_2$—O), (A1288: MeO, HO—(CH$_2$)$_3$—O), (A1289: MeO, 4-HO-pipe), (A1290: MeO, 3-HO-pyrr), (A1291: MeO, 4-HO$_2$C-pipe), (A1292: MeO, 4-(cyano)-pipe), (A1293: MeO, 4-Ac-pipa), (A1294: MeO, 3-oxo-pipa), (A1295: HO, H), (A1296: HO—(CH$_2$)$_2$—O, H), (A1297: HO—(CH$_2$)$_3$—O, H), (A1298: 4-HO-pipe, H), (A1299: 3-HO-pyrr, H), (A1300: 4-HO$_2$C-pipe, H), (A1301: 4-(cyano)-pipe, H), (A1302: 4-Ac-pipe, H), (A1303: 3-oxo-pipa, H).

TABLE 29

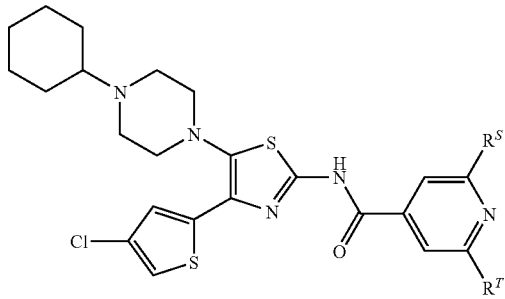

(No: $R^S$, $R^T$) =
(A1304: H, H), (A1305: H, HO—(CH$_2$)$_2$—O), (A1306: H, HO—(CH$_2$)$_3$—O), (A1307: H, 4-HO-pipe), (A1308: H, 3-HO-pyrr), (A1309: H, 4-HO$_2$C-pipe), (A1310: H, 4-(cyano)-pipe), (A1311: H, 4-Ac-pipa), (A1312: H, 3-oxo-pipa), (A1313: Cl, HO—(CH$_2$)$_2$—O), (A1314: Cl, HO—(CH$_2$)$_3$—O), (A1315: Cl, 4-HO-pipe), (A1316: Cl, 3-HO-pyrr), (A1317: Cl, 4-HO$_2$C-pipe), (A1318: Cl, 4-(cyano)-pipe), (A1319: Cl, 4-Ac-pipa), (A1320: Cl, 3-oxo-pipa), (A1321: Me, HO—(CH$_2$)$_2$—O), (A1322: Me, HO—(CH$_2$)$_3$—O), (A1323: Me, 4-HO-pipe), (A1324: Me, 3-HO-pyrr), (A1325: Me, 4-HO$_2$C-pipe), (A1326: Me, 4-(cyano)-pipe), (A1327: Me, 4-Ac-pipa), (A1328: Me, 3-oxo-pipa), (A1329: MeO, HO—(CH$_2$)$_2$—O), (A1330: MeO, HO—(CH$_2$)$_3$—O), (A1331: MeO, 4-HO-pipe), (A1332: MeO, 3-HO-pyrr), (A1333: MeO, 4-HO$_2$C-pipe), (A1334: MeO, 4-(cyano)-pipe), (A1335: MeO, 4-Ac-pipa), (A1336: MeO, 3-oxo-pipa).

TABLE 30

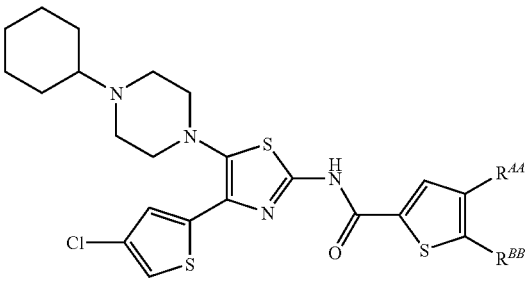

(No: $R^{AA}$, $R^{BB}$) =
(A1337: H, HO), (A1338: H, HO—(CH$_2$)$_2$—O), (A1339: H, HO—(CH$_2$)$_3$—O), (A1340: H, 4-HO-pipe), (A1341: H, 3-HO-pyrr), (A1342: H, 4-HO$_2$C-pipe), (A1343: H, 4-(cyano)-pipe), (A1344: H, 4-Ac-pipa), (A1345: H, 3-oxo-pipa), (A1346: F, HO), (A1347: F, HO—(CH$_2$)$_2$—O), (A1348: F, HO—(CH$_2$)$_3$—O), (A1349: F, 4-HO-pipe), (A1350: F, 3-HO-pyrr), (A1351: F, 4-HO$_2$C-pipe), (A1352: F, 4-(cyano)-pipe), (A1353: F, 4-Ac-pipa), (A1354: F, 3-oxo-pipa), (A1355: Cl, HO), (A1356: Cl, HO—(CH$_2$)$_2$—O), (A1357: Cl, HO—(CH$_2$)$_3$—O), (A1358: Cl, 4-HO-pipe), (A1359: Cl, 3-HO-pyrr), (A1360: Cl, 4-HO$_2$C-pipe), (A1361: Cl, 4-(cyano)-pipe), (A1362: Cl, 4-Ac-pipa), (A1363: Cl, 3-oxo-pipa), (A1364: Br, HO), (A1365: Br, HO—(CH$_2$)$_2$—O), (A1366: Br, HO—(CH$_2$)$_3$—O), (A1367: Br, 4-HO-pipe), (A1368: Br, 3-HO-pyrr), (A1369: Br, 4-HO$_2$C-pipe), (A1370: Br, 4-(cyano)-pipe), (A1371: Br, 4-Ac-pipa), (A1372: Br, 3-oxo-pipa), (A1373: Me, HO), (A1374: Me, HO—(CH$_2$)$_2$—O), (A1375: Me, HO—(CH$_2$)$_3$—O), (A1376: Me, 4-HO-pipe), (A1377: Me, 3-HO-pyrr), (A1378: Me, 4-HO$_2$C-pipe), (A1379: Me, 4-(cyano)-pipe), (A1380: Me, 4-Ac-pipa), (A1381: Me, 3-oxo-pipa), (A1382: HO, HO), (A1383: HO, HO—(CH$_2$)$_2$—O), (A1384: HO, HO—(CH$_2$)$_3$—O), (A1385: HO, 4-HO-pipe), (A1386: HO, 3-HO-pyrr), (A1387: HO, 4-HO$_2$C-pipe), (A1388: HO, 4-(cyano)-pipe), (A1389: HO, 4-Ac-pipa), (A1390: HO, 3-oxo-pipa), (A1391: MeO, HO), (A1392: MeO, HO—(CH$_2$)$_2$—O), (A1393: MeO, HO—(CH$_2$)$_3$—O), (A1394: MeO, 4-HO-pipe), (A1395: MeO, 3-HO-pyrr), (A1396: MeO, 4-HO$_2$C-pipe), (A1397: MeO, 4-(cyano)-pipe), (A1398: MeO, 4-Ac-pipa), (A1399: MeO, 3-oxo-pipa).

TABLE 31

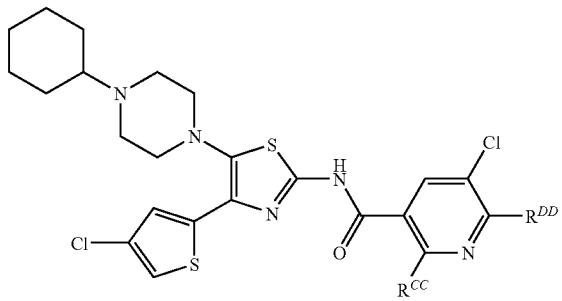

(No: R^CC, R^DD) =

(A1400: H₂N, HO), (A1401: H₂N, HO—(CH₂)₂—O), (A1402: H₂N, HO—(CH₂)₃—O), (A1403: H₂N, 4-HO-pipe), (A1404: H₂N, 3-HO-pyrr), (A1405: H₂N, 4-HO2C-pipe), (A1406: H₂N, 4-(cyano)-pipe), (A1407: H₂N-Ac-pipa), (A1408: H₂N, 3-oxo-pipa), (A1409: MeHN, HO), (A1410: MeHN, HO—(CH₂)₂—O), (A1411: MeHN, HO—(CH₂)₃—O), (A1412: MeHN, 4-HO-pipe), (A1413: MeHN, 3-HO-pyrr), (A1414: MeHN, 4-HO₂C-pipe), (A1415: MeHN, 4-(cyano)-pipe), (A1416: MeHN, 4-Ac-pipa), (A1417: MeHN, 3-oxo-pipa), (A1418: HO, HO), (A1419: HO, HO—(CH₂)₂—O), (A1420: HO, HO—(CH₂)₃—O), (A1421: HO, 4-HO-pipe), (A1422: HO, 3-HO-pyrr), (A1423: HO, 4-HO₂C-pipe), (A1424: HO, 4-(cyano)-pipe), (A1425: HO, 4-Ac-pipa), (A1426: HO, 3-oxo-pipa), (A1427: MeO, HO), (A1428: MeO, HO—(CH₂)₂—O), (A1429: MeO, HO—(CH₂)₃—O), (A1430: MeO, 4-HO-pipe), (A1431: MeO, 3-HO-pyrr), (A1432: MeO, 4-HO₂C-pipe), (A1433: MeO, 4-(cyano)-pipe), (A1434: MeO, 4-Ac-pipa), (A1435: MeO, 3-oxo-pipa), (A1436: Cl, HO), (A1437: Cl, HO—(CH₂)₂—O), (A1438: Cl, HO—(CH₂)₃—O), (A1439: Cl, 4-HO-pipe), (A1440: Cl, 3-HO-pyrr), (A1441: Cl, 4-HO₂C-pipe), (A1442: Cl, 4-(cyano)-pipe), (A1443: Cl, 4-Ac-pipa), (A1444: Cl, 3-oxo-pipa).

TABLE 32

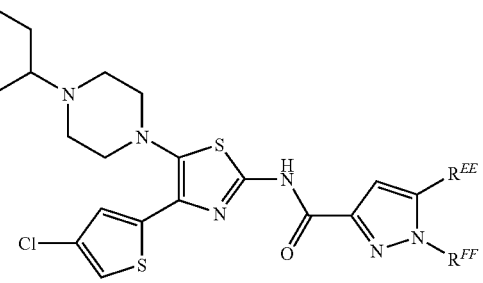

(No: R^EE, R^FF) =

(A1445: H, HO—(CH₂)₂), (A1446: H, HO—(CH₂)₃), (A1447: F, HO—(CH₂)₂), (A1448: F, HO—(CH₂)₃), (A1449: Cl, HO—(CH₂)₂), (A1450: Cl, HO—(CH₂)₃), (A1451: Me, HO—(CH₂)₂), (A1452: Me, HO—(CH₂)₃), (A1453: HO, HO—(CH₂)₂), (A1454: HO, HO—(CH₂)₃), (A1455: MeO, HO—(CH₂)₂), (A1456: MeO, HO—(CH₂)₃).

TABLE 33

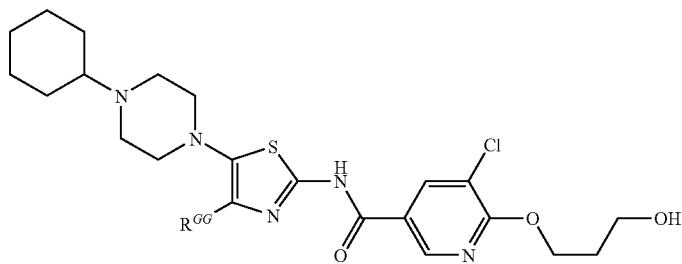

(No: $R^{GG}$) =
(A1457: 5-F-2-The), (A1458: 5-Cl-2-The), (A1459: 5-Br-2-The), (A1460: 5-Me-2-The), (A1461: 5-F$_3$C-2-The), (A1462: 4-F-2-The), (A1463: 4-Cl-2-The), (A1464: 4-Br-2-The), (A1465: 4-Me-2-The), (A1466: 4-F$_3$C-2-The), (A1467: 4-F-5-Cl-2-The), (A1468: 4,5-diCl-2-The), (A1469: 4-Br-5-Cl-2-The), (A1470: 4-Me-5-Cl-2-The), (A1471: 4-F$_3$C-5-Cl-2-The), (A1472: 4-F-Ph), (A1473: 4-Cl-Ph), (A1474: 4-Br-Ph), (A1475: 4-Me-Ph), (A1476: 4-F$_3$C-Ph), (A1477: 3-F-Ph), (A1478: 3-Cl-Ph), (A1479: 3-Br-Ph), (A1480: 3-Me-Ph), (A1481: 3-F$_3$C-Ph), (A1482: 2-F-Ph), (A1483: 2-Cl-Ph), (A1484: 2-Br-Ph), (A1485: 2-Me-Ph), (A1486: 2-F$_3$C-Ph), (A1487: 3,4-diF-Ph), (A1488: 3-Cl-4-F-Ph), (A1489: 3-Br-4-F-Ph), (A1490: 3-Me-4-F-Ph), (A1491: 3-F$_3$C-4-F-Ph), (A1492: 5-Me-2-Py), (A1493:6-Me-3-Py), (A1494: 4-Py), (A1495: 2-pyrimidinyl), (A1496: 2-Me-4-pyrimidinyl), (A1497: 2-Me-5-pyrimidinyl), (A1498: 4-pyridazinyl), (A1499:6-Me-3-pyridazinyl), (A1500: 5-Me-2-pyrazinyl), (A1501: 4-Me-2-Fur), (A1502: 1-Me-3-pyrrolyl), (A1503: 4-Me-2-thiazolyl), (A1504: 4-Cl-2-thiazolyl), (A1505: 4-F$_3$C-2-thiazolyl), (A1506: 5-Me-2-thiazolyl), (A1507: 2-Me-5-thiazolyl), (A1508: 5-Me-2-oxazolyl), (A1509: 2-Me-5-oxazolyl), (A1510: 4-Me-2-imidazolyl), (A1511: 2-Me-4-imidazolyl), (A1512: 1-Me-4-imidazolyl), (A1513: 5-Me-3-isothiazolyl), (A1514: 3-Me-5-isothiazolyl), (A1515: 5-Me-3-isoxazolyl), (A1516: 3-Me-5-isoxazolyl), (A1517: 5-Me-3-pyrazolyl), (A1518: 1-Me-4-pyrazolyl), (A1519: 1-Me-3-pyrazolyl), (A1520: 5-Me-1,3,4-thiadiazol-2-yl), (A1521: 5-Me-1,3,4-oxadiazol-2-yl), (A1522: 5-Me-1,2,4-triazol-3-yl), (A1523: 1-Me-1,2,4-triazol-3-yl), (A1524: 5-Me-1,2,4-thiadiazol-3-yl), (A1525: 3-Me-1,2,4-thiadiazol-5-yl), (A1526: 5-Me-1,2,4-oxadiazol-3-yl), (A1527: 3-Me-1,2,4-oxadiazol-5-yl), (A1528: 1-Me-1,2,3-triazol-4-yl).

The invention claimed is:

1. A method for the treatment of idiopathic thrombocytopenia purpura in a subject in need thereof, the method comprising:

administering to a subject in need thereof therapeutically effective amount of a compound selected from the group consisting of:

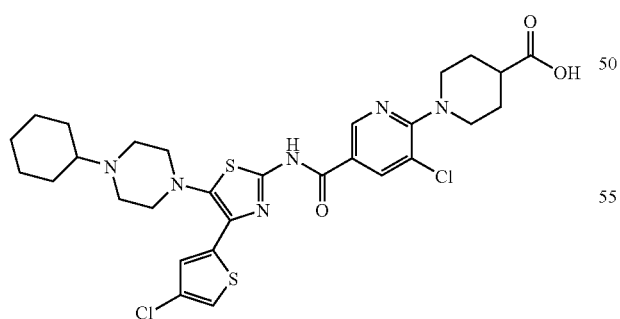

and pharmaceutically acceptable salts thereof, wherein idiopathic thrombocytopenia purpura in the subject is treated.

2. The method according to claim 1, wherein the compound is:

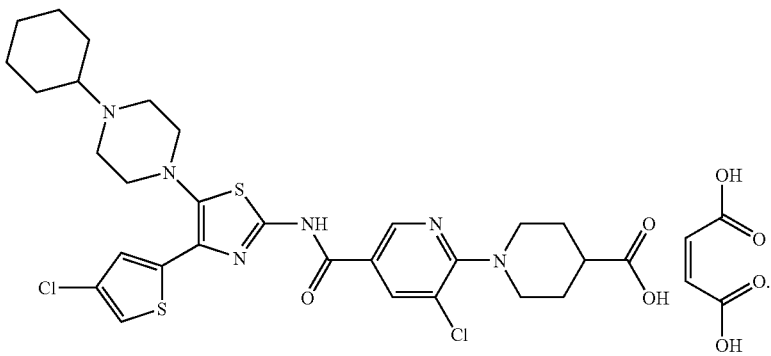

3. The method according to claim 1 or 2, wherein the method comprises: administering the compound in a pharmaceutical composition comprising the compound and a pharmaceutically acceptable carrier.

4. The method according to claim 3, wherein the pharmaceutical composition is formulated for oral administration.

5. The method according to claim 4, wherein the effective amount of the compound is a daily dosage of between about 0.01 and about 1 mg/kg.

6. The method according to claim 5, wherein the method comprises:
administering the effective amount of the compound in the form of one or more tablets once daily.

7. The method according to claim 3, wherein the method comprises:
administering the therapeutically effective amount of the compound to the subject having a depressed platelet level, wherein the platelet level in the subject is increased or recovered.

8. The method according to claim 1 or 2, wherein the method comprises: administering the therapeutically effective amount of the compound to the subject such that administration results in cell proliferation and production of mature megakaryocytes and platelets.

* * * * *